US012746198B2

(12) United States Patent
Weiler et al.

(10) Patent No.: US 12,746,198 B2
(45) Date of Patent: Sep. 29, 2026

(54) AQUEOUS PHARMACEUTICAL COMPOSITIONS COMPRISING SGLT-2 INHIBITORS

(71) Applicant: Boehringer Ingelheim Vetmedica GmbH, Ingelheim am Rhein (DE)

(72) Inventors: Claudius Weiler, Ingelheim am Rhein (DE); Thomas Adam Duch, Gau-Algesheim (DE)

( * ) Notice: Subject to any disclaimer, the term of this patent is extended or adjusted under 35 U.S.C. 154(b) by 599 days.

(21) Appl. No.: 18/321,117

(22) Filed: May 22, 2023

(65) Prior Publication Data

US 2023/0381101 A1 Nov. 30, 2023

(30) Foreign Application Priority Data

May 25, 2022 (EP) .................................... 22175413

(51) Int. Cl.

*A61K 9/08* (2006.01)
*A61K 31/7004* (2006.01)
*A61K 31/7034* (2006.01)
*A61K 31/7042* (2006.01)
*A61K 31/7048* (2006.01)
*A61K 31/7056* (2006.01)
*A61K 47/02* (2006.01)
*A61K 47/10* (2017.01)
*A61K 47/12* (2006.01)
*A61K 47/20* (2006.01)
*A61K 47/26* (2006.01)
*A61K 47/32* (2006.01)
*A61K 47/46* (2006.01)

(52) U.S. Cl.

CPC ............ *A61K 9/08* (2013.01); *A61K 31/7004* (2013.01); *A61K 31/7034* (2013.01); *A61K 31/7042* (2013.01); *A61K 31/7048* (2013.01); *A61K 31/7056* (2013.01); *A61K 47/02* (2013.01); *A61K 47/10* (2013.01); *A61K 47/12* (2013.01); *A61K 47/20* (2013.01); *A61K 47/26* (2013.01); *A61K 47/32* (2013.01); *A61K 47/46* (2013.01)

(58) Field of Classification Search

CPC ............ A61K 31/7034; A61K 31/7042; A61K 31/7048; A61K 31/7056; A61K 9/08

See application file for complete search history.

(56) References Cited

U.S. PATENT DOCUMENTS 2,749,339 A 6/1956 Barry et al.
3,174,901 A 3/1965 Sterne
3,732,231 A 5/1973 Semonsky et al.
3,884,906 A 5/1975 Van Der Meer et al.
3,901,894 A 8/1975 Kornfeld et al.
3,920,664 A 11/1975 Clemens et al.
3,959,288 A 5/1976 Bach et al.
4,166,182 A 8/1979 Kornfeld et al.
4,246,265 A 1/1981 Kornfeld et al.
4,355,040 A 10/1982 Furukawa et al.
4,379,785 A 4/1983 Weyer et al.
4,412,993 A 11/1983 Sokolowski
4,448,778 A 5/1984 Lynch
4,602,023 A 7/1986 Kiely et al.
4,639,436 A 1/1987 Junge et al.
4,782,152 A 11/1988 Misner
4,786,023 A 11/1988 Harris et al.
4,786,755 A 11/1988 Kiely et al.
4,880,804 A 11/1989 Carini et al.
5,512,054 A 4/1996 Morningstar
5,591,762 A 1/1997 Hauel et al.
5,846,962 A 12/1998 Suzuki et al.
6,028,091 A 2/2000 Hill
6,204,281 B1 3/2001 Webb et al.
6,358,986 B1 3/2002 Schneider
6,391,849 B1 5/2002 Shamay et al.
6,410,742 B1 6/2002 Schneider
6,414,126 B1 7/2002 Ellsworth et al.
6,515,117 B2 2/2003 Ellsworth et al.
6,589,547 B1 7/2003 Igari et al.
6,613,806 B1 9/2003 Aven et al.
6,627,611 B2 9/2003 Tomiyama et al.
6,737,432 B2 5/2004 Donsbach et al.
6,774,112 B2 8/2004 Gougoutas
6,794,480 B2 9/2004 Goto et al.
6,936,590 B2 8/2005 Washburn et al.
6,972,283 B2 12/2005 Fujikura et al.
7,101,856 B2 9/2006 Glombik et al.
7,169,761 B2 1/2007 Tomiyama et al.
7,202,350 B2 4/2007 Imamura et al.
7,371,732 B2 5/2008 Eickelmann et al.
7,375,087 B2 5/2008 Teranishi et al.

(Continued)

FOREIGN PATENT DOCUMENTS

CA 2352436 A1 7/2000
CA 2382480 A1 3/2001

(Continued)

OTHER PUBLICATIONS

Wallenius, Lipid Res Mar. 2022; 63(3);100176. (Year: 2022).*
Laine, International Journal of Pharmaceutics 576 (2020) 119019. (Year: 2020).*
Vadlamudi, 2107 IOP Conf. Ser: Mater. Sci. Eng. 263 022023. (Year: 2017).*
Abdollahpour, J. Iran. Chem. Soc. vol. 7, No. 2, Jun. 2010, pp. 516-520. (Year: 2010).*
Haznedaroglu, Oral Surgery, Oral Medicine, Oral Pathology, Oral Radiology, and Endodontology vol. 96, Issue 3, Sep. 2003, pp. 340-344. (Year: 2003).*
CN112239440a, machine translation, Jan. 2021. (Year: 2021).*
Mahmood, Iftekhar, "Application of Allometric Principles for the Prediction for the Prediction of Pharmacokinetics in Human and Veterinary Drug Development", Advanced Drug Delivery Reviews, vol. 59, 2007, pp. 1177-1192.

(Continued)

*Primary Examiner* — Layla D Berry
(74) *Attorney, Agent, or Firm* — Katrina Bergbauer

(57) ABSTRACT

The invention relates to novel aqueous pharmaceutical compositions comprising at least one SGLT-2 inhibitor and one or more solubilizing agents as well as corresponding processes of manufacturing such aqueous pharmaceutical compositions and their medical uses.

28 Claims, No Drawings

(56) References Cited

U.S. PATENT DOCUMENTS

| | | | |
|---|---|---|---|
| 7,375,090 | B2 | 5/2008 | Himmelsbach et al. |
| 7,375,213 | B2 | 5/2008 | Deshpande et al. |
| 7,393,836 | B2 | 7/2008 | Eckhardt et al. |
| 7,417,032 | B2 | 8/2008 | Eckhardt et al. |
| 7,419,959 | B2 | 9/2008 | Eckhardt et al. |
| 7,524,822 | B2 | 4/2009 | Kraemer et al. |
| 7,541,341 | B2 | 6/2009 | Fushimi et al. |
| 7,579,449 | B2 | 8/2009 | Eckhardt et al. |
| 7,589,193 | B2 | 9/2009 | Washburn et al. |
| 7,662,790 | B2 | 2/2010 | Himmelsbach et al. |
| 7,683,160 | B2 | 3/2010 | Eckhardt et al. |
| 7,687,469 | B2 | 3/2010 | Eckhardt et al. |
| 7,713,938 | B2 | 5/2010 | Himmelsbach et al. |
| 7,723,309 | B2 | 5/2010 | Himmelsbach et al. |
| 7,745,414 | B2 | 6/2010 | Eckhardt et al. |
| 7,772,191 | B2 | 8/2010 | Eckhardt et al. |
| 7,772,192 | B2 | 8/2010 | Esko |
| 7,772,378 | B2 | 8/2010 | Himmelsbach et al. |
| 7,772,407 | B2 | 8/2010 | Imamura et al. |
| 7,776,830 | B2 | 8/2010 | Eckhardt et al. |
| 7,847,074 | B2 | 12/2010 | Eckhardt et al. |
| 7,851,502 | B2 | 12/2010 | Bindra et al. |
| 7,851,602 | B2 | 12/2010 | Himmelsbach et al. |
| 7,858,587 | B2 | 12/2010 | Eckhardt et al. |
| 7,867,469 | B2 | 1/2011 | Afzali-Ardakani et al. |
| 7,879,806 | B2 | 2/2011 | Himmelsbach et al. |
| 7,879,807 | B2 | 2/2011 | Himmelsbach et al. |
| 8,039,441 | B2 | 10/2011 | Himmelsbach et al. |
| 8,080,580 | B2 | 12/2011 | Mascitti et al. |
| 8,088,743 | B2 | 1/2012 | Washburn et al. |
| 8,097,592 | B2 | 1/2012 | Imamura et al. |
| 8,133,916 | B1 | 3/2012 | Horseman et al. |
| 8,232,281 | B2 | 7/2012 | Dugi et al. |
| 8,283,326 | B2 | 10/2012 | Eckhardt et al. |
| 8,283,454 | B2 | 10/2012 | Liou et al. |
| 8,316,972 | B2 | 11/2012 | Hutcheson et al. |
| 8,361,972 | B2 | 1/2013 | Bindra et al. |
| 8,507,450 | B2 | 8/2013 | Eckhardt et al. |
| 8,551,957 | B2 | 10/2013 | Dugi et al. |
| 8,557,782 | B2 | 10/2013 | Eckhardt et al. |
| 8,772,278 | B2 | 7/2014 | Stark et al. |
| 8,871,795 | B2 | 10/2014 | Mohr et al. |
| 8,987,323 | B2 | 3/2015 | Cai et al. |
| 9,145,434 | B2 | 9/2015 | Eckhardt et al. |
| 9,192,617 | B2 | 11/2015 | Mayoux et al. |
| 9,308,197 | B2 | 4/2016 | Stark et al. |
| 9,487,557 | B2 | 11/2016 | Iscovich et al. |
| 9,505,734 | B2 | 11/2016 | Zhao et al. |
| 9,566,388 | B1 | 2/2017 | Jones |
| 9,585,873 | B2 | 3/2017 | Stark et al. |
| 9,744,158 | B2 | 8/2017 | Lagarde et al. |
| 9,949,954 | B2 | 4/2018 | Stark et al. |
| 9,949,998 | B2 | 4/2018 | Broedl et al. |
| 10,220,017 | B2 | 3/2019 | Weiler et al. |
| 10,258,637 | B2 | 4/2019 | Broedl et al. |
| 10,294,259 | B2 | 5/2019 | Zhao et al. |
| 10,357,479 | B2 | 7/2019 | Stark et al. |
| 10,406,172 | B2 | 9/2019 | Eickelmann et al. |
| 10,537,570 | B2 | 1/2020 | Schummer et al. |
| 10,555,958 | B2 | 2/2020 | Reiche et al. |
| 10,603,300 | B2 | 3/2020 | Kley et al. |
| 10,617,666 | B2 | 4/2020 | Reiche et al. |
| 10,688,116 | B2 | 6/2020 | Reiche et al. |
| 10,709,683 | B2 | 7/2020 | Weiler et al. |
| 10,864,225 | B2 | 12/2020 | Reiche et al. |
| 11,007,172 | B2 | 5/2021 | Minamino |
| 11,090,323 | B2 | 8/2021 | Broedl et al. |
| 11,225,500 | B2 | 1/2022 | Eckhardt et al. |
| 11,433,045 | B2 | 9/2022 | Kley et al. |
| 11,443,045 | B2 | 9/2022 | Rahnama-Moghaddam et al. |
| 11,629,161 | B2 | 4/2023 | Eckhardt et al. |
| 11,759,474 | B2 | 9/2023 | Reiche |
| 11,826,378 | B2 | 11/2023 | Kroh et al. |
| 11,833,166 | B2 | 12/2023 | Broedl et al. |
| 11,896,574 | B2 | 2/2024 | Reiche et al. |
| 2002/0094997 | A1 | 7/2002 | Schneider et al. |
| 2002/0137903 | A1 | 9/2002 | Ellsworth et al. |
| 2003/0064935 | A1 | 4/2003 | Gougoutas |
| 2003/0087843 | A1 | 5/2003 | Washburn |
| 2003/0114390 | A1 | 6/2003 | Washburn et al. |
| 2004/0033258 | A1 | 2/2004 | Koike |
| 2004/0110813 | A1 | 6/2004 | Nakatani et al. |
| 2004/0138148 | A1 | 7/2004 | Fushimi et al. |
| 2004/0138439 | A1 | 7/2004 | Deshpande et al. |
| 2004/0178525 | A1 | 9/2004 | Kagei et al. |
| 2004/0219208 | A1 | 11/2004 | Kawamura et al. |
| 2004/0258778 | A1 | 12/2004 | Farmar et al. |
| 2005/0065098 | A1 | 3/2005 | Fujikura et al. |
| 2005/0070594 | A1 | 3/2005 | Kauschke et al. |
| 2005/0085680 | A1 | 4/2005 | Auerbach et al. |
| 2005/0124555 | A1 | 6/2005 | Tomiyama et al. |
| 2005/0186274 | A1 | 8/2005 | Kohlrausch |
| 2005/0187168 | A1 | 8/2005 | Eickelmann et al. |
| 2005/0191653 | A1 | 9/2005 | Freier et al. |
| 2005/0209166 | A1 | 9/2005 | Eckhardt et al. |
| 2005/0233982 | A1 | 10/2005 | Himmelsbach et al. |
| 2005/0272649 | A1 | 12/2005 | Hruska et al. |
| 2006/0009400 | A1 | 1/2006 | Eckhardt et al. |
| 2006/0019948 | A1 | 1/2006 | Eckhardt et al. |
| 2006/0025349 | A1 | 2/2006 | Eckhardt et al. |
| 2006/0034489 | A1 | 2/2006 | McClanahan |
| 2006/0035841 | A1 | 2/2006 | Eckhardt et al. |
| 2006/0063722 | A1 | 3/2006 | Washburn et al. |
| 2006/0074031 | A1 | 4/2006 | Eckhardt et al. |
| 2006/0142210 | A1 | 6/2006 | Eckhardt et al. |
| 2006/0189548 | A1 | 8/2006 | Himmelsbach et al. |
| 2006/0234953 | A1 | 10/2006 | Himmelsbach et al. |
| 2006/0251728 | A1 | 11/2006 | Himmelsbach et al. |
| 2006/0258749 | A1 | 11/2006 | Eckhardt et al. |
| 2007/0004648 | A1 | 1/2007 | Himmelsbach et al. |
| 2007/0026026 | A1 | 2/2007 | Delmarre et al. |
| 2007/0027092 | A1 | 2/2007 | Himmelsbach et al. |
| 2007/0049537 | A1 | 3/2007 | Eckhardt et al. |
| 2007/0054867 | A1 | 3/2007 | Eckhardt et al. |
| 2007/0073046 | A1 | 3/2007 | Eckhardt et al. |
| 2007/0155679 | A1 | 7/2007 | Daemmgen et al. |
| 2007/0249544 | A1 | 10/2007 | Himmelsbach et al. |
| 2007/0259821 | A1 | 11/2007 | Eckhardt et al. |
| 2007/0281940 | A1 | 12/2007 | Dugi et al. |
| 2008/0058379 | A1 | 3/2008 | Eckhardt et al. |
| 2008/0105481 | A1 | 5/2008 | Hutcheson et al. |
| 2008/0146543 | A1 | 6/2008 | Stark et al. |
| 2008/0234367 | A1 | 9/2008 | Washburn et al. |
| 2008/0259821 | A1 | 10/2008 | Funk et al. |
| 2008/0287529 | A1 | 11/2008 | Deshpande et al. |
| 2009/0023913 | A1 | 1/2009 | Eckhardt et al. |
| 2009/0143316 | A1 | 6/2009 | Imamura et al. |
| 2009/0285916 | A1 | 11/2009 | Haritou |
| 2009/0318547 | A1 | 12/2009 | Eckhardt et al. |
| 2009/0326215 | A1 | 12/2009 | Eckhardt et al. |
| 2010/0056618 | A1 | 3/2010 | Mascitti et al. |
| 2010/0069310 | A1 | 3/2010 | Himmelsbach et al. |
| 2010/0081625 | A1 | 4/2010 | Wienrich et al. |
| 2010/0093654 | A1 | 4/2010 | Himmelsbach et al. |
| 2010/0099641 | A1 | 4/2010 | Himmelsbach et al. |
| 2010/0167988 | A1 | 7/2010 | Gant et al. |
| 2010/0167989 | A1 | 7/2010 | Gant et al. |
| 2010/0179191 | A1 | 7/2010 | Himmelsbach et al. |
| 2010/0209506 | A1 | 8/2010 | Eisenreich |
| 2010/0240879 | A1 | 9/2010 | Eckhardt et al. |
| 2010/0249392 | A1 | 9/2010 | Eckhardt et al. |
| 2010/0298243 | A1 | 11/2010 | Manuchehri et al. |
| 2010/0317847 | A1 | 12/2010 | Eckhardt et al. |
| 2011/0014284 | A1 | 1/2011 | Eisenreich et al. |
| 2011/0046076 | A1 | 2/2011 | Eickelmann et al. |
| 2011/0046087 | A1 | 2/2011 | Eickelmann et al. |
| 2011/0065731 | A1 | 3/2011 | Dugi et al. |
| 2011/0077212 | A1 | 3/2011 | Seed et al. |
| 2011/0077213 | A1 | 3/2011 | Halperin |
| 2011/0098240 | A1 | 4/2011 | Dugi et al. |
| 2011/0178033 | A1 | 7/2011 | Eckhardt et al. |
| 2011/0195917 | A1 | 8/2011 | Dugi et al. |
| 2011/0212905 | A1 | 9/2011 | Nomura et al. |
| 2011/0236477 | A1 | 9/2011 | Schneider et al. |

(56) References Cited

U.S. PATENT DOCUMENTS

| | | | | |
|---|---|---|---|---|
| 2011/0237526 | A1 | 9/2011 | Weber et al. | |
| 2011/0237532 | A1 | 9/2011 | De Vries et al. | |
| 2011/0237789 | A1 | 9/2011 | Weber et al. | |
| 2011/0245261 | A1 | 10/2011 | Lagarde et al. | |
| 2011/0275703 | A1 | 11/2011 | Sato et al. | |
| 2012/0095069 | A1 | 4/2012 | Mohr et al. | |
| 2012/0115958 | A1* | 5/2012 | Mariotti .................. | A61K 9/08 514/777 |
| 2012/0196812 | A1 | 8/2012 | Eickelmann et al. | |
| 2012/0237593 | A1 | 9/2012 | Comiskey et al. | |
| 2012/0275703 | A1 | 11/2012 | Lv et al. | |
| 2012/0277175 | A1 | 11/2012 | Neto et al. | |
| 2012/0283169 | A1 | 11/2012 | Grempler et al. | |
| 2012/0296080 | A1 | 11/2012 | Eckhardt et al. | |
| 2013/0046088 | A1 | 2/2013 | Liou et al. | |
| 2013/0064887 | A1 | 3/2013 | Ito et al. | |
| 2013/0096076 | A1 | 4/2013 | Dugi et al. | |
| 2014/0002670 | A1 | 1/2014 | Kolarov et al. | |
| 2014/0024670 | A1 | 1/2014 | Isaka et al. | |
| 2014/0031540 | A1 | 1/2014 | Eckhardt et al. | |
| 2014/0288138 | A1 | 9/2014 | Stark et al. | |
| 2014/0303096 | A1 | 10/2014 | Reiche et al. | |
| 2014/0364473 | A1 | 12/2014 | Mohr et al. | |
| 2015/0164856 | A1 | 6/2015 | Reiche et al. | |
| 2015/0272977 | A1 | 10/2015 | Reiche et al. | |
| 2015/0279297 | A1 | 10/2015 | Nakano et al. | |
| 2016/0000816 | A1 | 1/2016 | Broedl et al. | |
| 2016/0166774 | A1 | 6/2016 | Leary | |
| 2016/0361289 | A1 | 12/2016 | Kley et al. | |
| 2017/0056366 | A1 | 3/2017 | Weiler et al. | |
| 2017/0071969 | A1 | 3/2017 | Reiche et al. | |
| 2017/0145000 | A1 | 5/2017 | Sheng et al. | |
| 2017/0239281 | A1 | 8/2017 | Reiche et al. | |
| 2017/0259821 | A1 | 9/2017 | Nakadori | |
| 2017/0266152 | A1 | 9/2017 | Broedl et al. | |
| 2019/0076395 | A1 | 3/2019 | Lauring et al. | |
| 2020/0054656 | A1 | 2/2020 | Kim | |
| 2020/0179328 | A1 | 6/2020 | Kley et al. | |
| 2020/0197352 | A1 | 6/2020 | Reiche et al. | |
| 2020/0237794 | A1 | 7/2020 | Reiche et al. | |
| 2020/0368261 | A1 | 11/2020 | Broedl et al. | |
| 2021/0069222 | A1 | 3/2021 | Reiche et al. | |
| 2021/0205324 | A1 | 7/2021 | Wienrich et al. | |
| 2021/0260090 | A1 | 8/2021 | Kroh et al. | |
| 2022/0016078 | A1 | 1/2022 | Desai et al. | |
| 2022/0096505 | A1 | 3/2022 | Broedl et al. | |
| 2022/0152159 | A1 | 5/2022 | Grempler et al. | |
| 2022/0313716 | A1 | 10/2022 | Eickelmann et al. | |
| 2022/0313736 | A1 | 10/2022 | Li et al. | |
| 2022/0378737 | A1 | 12/2022 | Kley et al. | |
| 2023/0000816 | A1 | 1/2023 | Hadd et al. | |
| 2023/0006745 | A1 | 1/2023 | Wang et al. | |
| 2023/0140631 | A1 | 5/2023 | Reiche et al. | |
| 2023/0285432 | A1 | 9/2023 | Eickelmann et al. | |
| 2023/0346817 | A1 | 11/2023 | Jia et al. | |
| 2023/0381101 | A1 | 11/2023 | Weiler et al. | |
| 2024/0050456 | A1 | 2/2024 | Kroh et al. | |
| 2024/0269105 | A1 | 8/2024 | Matallo et al. | |
| 2024/0307426 | A1 | 9/2024 | Kroh et al. | |
| 2024/0307628 | A1 | 9/2024 | Weiler et al. | |
| 2024/0390317 | A1 | 11/2024 | Kroh et al. | |
| 2024/0390332 | A1 | 11/2024 | Kroh et al. | |
| 2024/0398845 | A1 | 12/2024 | Kroh et al. | |
| 2025/0268929 | A1 | 8/2025 | Reiche et al. | |

FOREIGN PATENT DOCUMENTS

| | | | |
|---|---|---|---|
| CA | 2388818 | A1 | 4/2001 |
| CA | 2437240 | A1 | 8/2002 |
| CA | 2463146 | A1 | 5/2003 |
| CA | 2494177 | A1 | 2/2004 |
| CA | 2470365 | A1 | 6/2004 |
| CA | 2508024 | A1 | 6/2004 |
| CA | 2508226 | A1 | 6/2004 |
| CA | 2526145 | A1 | 9/2004 |
| CA | 2539032 | A1 | 3/2005 |
| CA | 2548353 | A1 | 7/2005 |
| CA | 2519584 | A1 | 9/2005 |
| CA | 2557269 | A1 | 9/2005 |
| CA | 2557320 | A1 | 9/2005 |
| CA | 2557801 | A1 | 10/2005 |
| CA | 2569915 | A1 | 1/2006 |
| CA | 2572149 | A1 | 1/2006 |
| CA | 2572819 | A1 | 1/2006 |
| CA | 2573777 | A1 | 2/2006 |
| CA | 2574451 | A1 | 2/2006 |
| CA | 2577320 | A1 | 3/2006 |
| CA | 2574500 | A1 | 4/2006 |
| CA | 2651019 | A1 | 11/2007 |
| CA | 2526145 | C | 11/2009 |
| CA | 2352436 | C | 3/2010 |
| CA | 2557801 | C | 6/2013 |
| CN | 1653075 | A | 8/2005 |
| CN | 1765362 | A | 5/2006 |
| CN | 101437807 | A | 5/2009 |
| CN | 101674831 | A | 3/2010 |
| CN | 102105153 | A | 6/2011 |
| CN | 102215843 | A | 10/2011 |
| CN | 102316875 | A | 1/2012 |
| CN | 103476457 | A | 12/2013 |
| CN | 103601709 | A | 2/2014 |
| CN | 104470908 | A | 3/2015 |
| CN | 106714796 | A | 5/2017 |
| CN | 107428695 | A | 12/2017 |
| CN | 111870694 | A | 11/2020 |
| DE | 1023027 | B | 1/1958 |
| DE | 2758025 | A1 | 7/1979 |
| DE | 2951135 | A1 | 6/1981 |
| DE | 10335027 | A1 | 2/2005 |
| EP | 0003667 | A1 | 8/1979 |
| EP | 0008391 | A1 | 3/1980 |
| EP | 0026671 | A1 | 4/1981 |
| EP | 0206567 | A2 | 12/1986 |
| EP | 0213850 | A2 | 3/1987 |
| EP | 0253310 | A2 | 1/1988 |
| EP | 0323841 | A2 | 7/1989 |
| EP | 0324377 | A2 | 7/1989 |
| EP | 0420237 | A1 | 4/1991 |
| EP | 0443983 | A1 | 8/1991 |
| EP | 0459136 | A1 | 12/1991 |
| EP | 0475206 | A2 | 3/1992 |
| EP | 0502314 | A1 | 9/1992 |
| EP | 0504888 | A1 | 9/1992 |
| EP | 0514198 | A1 | 11/1992 |
| EP | 1213296 | A1 | 6/2002 |
| EP | 1224195 | A1 | 7/2002 |
| EP | 1224195 | B | 7/2002 |
| EP | 1344780 | A1 | 9/2003 |
| EP | 1354888 | A1 | 10/2003 |
| EP | 1385856 | A | 2/2004 |
| EP | 1213296 | B1 | 4/2004 |
| EP | 1489089 | A1 | 12/2004 |
| EP | 1553094 | A1 | 7/2005 |
| EP | 1564210 | A1 | 8/2005 |
| EP | 1579862 | A1 | 9/2005 |
| EP | 1609785 | A1 | 12/2005 |
| EP | 1385856 | B1 | 2/2006 |
| EP | 1791852 | A2 | 6/2007 |
| EP | 2048150 | A1 | 4/2009 |
| EP | 1354888 | B1 | 5/2009 |
| EP | 2349272 | A1 | 8/2011 |
| EP | 2368552 | A1 | 9/2011 |
| EP | 2397174 | A2 | 12/2011 |
| EP | 2420232 | A2 | 2/2012 |
| EP | 2554199 | A1 | 2/2013 |
| EP | 2675527 | A1 | 12/2013 |
| EP | 14187228.3 | A | 10/2014 |
| EP | 1609785 | B1 | 2/2016 |
| EP | 2892268 | B1 | 3/2018 |
| EP | 2675527 | B1 | 10/2018 |
| EP | 2349272 | B1 | 1/2019 |
| EP | 3508222 | A1 | 7/2019 |
| EP | 2397174 | B1 | 11/2020 |

(56) References Cited

FOREIGN PATENT DOCUMENTS

| | | | |
|---|---|---|---|
| JP | 55007256 | A | 1/1980 |
| JP | S557256 | A | 1/1980 |
| JP | 56039056 | A | 4/1981 |
| JP | 58164502 | A | 9/1983 |
| JP | 62030750 | A | 2/1987 |
| JP | S6230750 | A | 2/1987 |
| JP | 11124392 | A | 5/1999 |
| JP | H11315034 | A1 | 11/1999 |
| JP | 2001288178 | A | 10/2001 |
| JP | 2003511458 | A | 3/2003 |
| JP | 2004196788 | A | 7/2004 |
| JP | 2004359630 | A | 12/2004 |
| JP | 2005002092 | A | 1/2005 |
| JP | 2005060625 | A | 3/2005 |
| JP | 2006516257 | A | 6/2006 |
| JP | 2009507809 | A | 2/2009 |
| JP | 2009531291 | A | 9/2009 |
| JP | 2009535378 | A | 10/2009 |
| JP | 2009545525 | A | 12/2009 |
| JP | 2010522244 | A | 7/2010 |
| JP | 2012500803 | A | 1/2012 |
| JP | 2012517975 | A | 8/2012 |
| JP | 2013541576 | A | 11/2013 |
| JP | 2015522644 | A | 8/2015 |
| JP | 2016539322 | A | 12/2016 |
| JP | 2016540790 | A | 12/2016 |
| JP | 6682621 | B2 | 4/2020 |
| KR | 20080102395 | A | 11/2008 |
| KR | 20090015912 | A | 2/2009 |
| KR | 20110118668 | A | 10/2011 |
| KR | 101458372 | B1 | 11/2014 |
| KR | 101770302 | B1 | 8/2017 |
| WO | 1991014679 | A1 | 10/1991 |
| WO | 1992010182 | A1 | 6/1992 |
| WO | 1993020816 | A1 | 10/1993 |
| WO | 1995026188 | A1 | 10/1995 |
| WO | 1996031234 | A1 | 10/1996 |
| WO | 1996040139 | A1 | 12/1996 |
| WO | 1997049392 | A1 | 12/1997 |
| WO | 9831697 | A1 | 7/1998 |
| WO | 1999044590 | A1 | 9/1999 |
| WO | 2000043370 | A1 | 7/2000 |
| WO | 2001016147 | A1 | 3/2001 |
| WO | 2001027128 | A1 | 4/2001 |
| WO | 2001074834 | A1 | 10/2001 |
| WO | 2001078699 | A2 | 10/2001 |
| WO | 2002011727 | A1 | 2/2002 |
| WO | 2002064606 | A1 | 8/2002 |
| WO | 2002083066 | A2 | 10/2002 |
| WO | 2002092081 | A1 | 11/2002 |
| WO | 2003009983 | A1 | 2/2003 |
| WO | 2003020737 | A1 | 3/2003 |
| WO | 2003031458 | A1 | 4/2003 |
| WO | 2003037876 | A1 | 5/2003 |
| WO | 2003078404 | A1 | 9/2003 |
| WO | 2003099836 | A1 | 12/2003 |
| WO | 2004007517 | A1 | 1/2004 |
| WO | 2004013118 | A1 | 2/2004 |
| WO | 2004014308 | A2 | 2/2004 |
| WO | 2004028505 | A1 | 4/2004 |
| WO | 2004046115 | A1 | 6/2004 |
| WO | 2004052902 | A1 | 6/2004 |
| WO | 2004052903 | A1 | 6/2004 |
| WO | 2004063209 | A2 | 7/2004 |
| WO | 2004076470 | A2 | 9/2004 |
| WO | 2004080990 | A1 | 9/2004 |
| WO | 2004096215 | A1 | 11/2004 |
| WO | 2004113378 | A2 | 12/2004 |
| WO | 2005012318 | A2 | 2/2005 |
| WO | 2005012326 | A1 | 2/2005 |
| WO | 2005021566 | A2 | 3/2005 |
| WO | 2005063785 | A2 | 7/2005 |
| WO | 2005070463 | A2 | 8/2005 |
| WO | 2005084647 | A1 | 9/2005 |
| WO | 2005085237 | A1 | 9/2005 |
| WO | 2005085265 | A1 | 9/2005 |
| WO | 2005092343 | A1 | 10/2005 |
| WO | 2005092877 | A1 | 10/2005 |
| WO | 2005123070 | A1 | 12/2005 |
| WO | 2006002912 | A1 | 1/2006 |
| WO | 2006006496 | A1 | 1/2006 |
| WO | 2006008038 | A1 | 1/2006 |
| WO | 2006010557 | A1 | 2/2006 |
| WO | 2006011469 | A1 | 2/2006 |
| WO | 2006018150 | A1 | 2/2006 |
| WO | 20060034489 | A2 | 3/2006 |
| WO | 2006037537 | A2 | 4/2006 |
| WO | 2006048208 | A1 | 5/2006 |
| WO | 2006064033 | A2 | 6/2006 |
| WO | 2006089872 | A1 | 8/2006 |
| WO | 2006108842 | A1 | 10/2006 |
| WO | 2006117359 | A1 | 11/2006 |
| WO | 2006117360 | A1 | 11/2006 |
| WO | 2006120208 | A1 | 11/2006 |
| WO | 2007000445 | A1 | 1/2007 |
| WO | 2007014894 | A2 | 2/2007 |
| WO | 2007025943 | A2 | 3/2007 |
| WO | 2007028814 | A1 | 3/2007 |
| WO | 2007031548 | A2 | 3/2007 |
| WO | 2007077457 | A2 | 7/2007 |
| WO | 2007080170 | A1 | 7/2007 |
| WO | 2007093601 | A1 | 8/2007 |
| WO | 2007093610 | A1 | 8/2007 |
| WO | 2007102999 | A2 | 9/2007 |
| WO | 2007114475 | A1 | 10/2007 |
| WO | 2007128749 | A1 | 11/2007 |
| WO | 2007128761 | A2 | 11/2007 |
| WO | 2007129053 | A1 | 11/2007 |
| WO | 2007140191 | A2 | 12/2007 |
| WO | 2007144175 | A2 | 12/2007 |
| WO | 2008002824 | A1 | 1/2008 |
| WO | 2008005240 | A2 | 1/2008 |
| WO | 2008013280 | A1 | 1/2008 |
| WO | 2008020011 | A1 | 2/2008 |
| WO | 2008034859 | A1 | 3/2008 |
| WO | 2008040774 | A2 | 4/2008 |
| WO | 2008042688 | A2 | 4/2008 |
| WO | 2008049923 | A1 | 5/2008 |
| WO | 2008055870 | A1 | 5/2008 |
| WO | 2008055940 | A2 | 5/2008 |
| WO | 2008069327 | A1 | 6/2008 |
| WO | 2008089872 | A1 | 7/2008 |
| WO | 2008089892 | A1 | 7/2008 |
| WO | 2008090210 | A1 | 7/2008 |
| WO | 2008101938 | A1 | 8/2008 |
| WO | 2008101939 | A1 | 8/2008 |
| WO | 2008101943 | A1 | 8/2008 |
| WO | 2008108957 | A2 | 9/2008 |
| WO | 2008110599 | A1 | 9/2008 |
| WO | 2008116179 | A1 | 9/2008 |
| WO | 2008116195 | A2 | 9/2008 |
| WO | 2008144316 | A1 | 11/2008 |
| WO | 2008153945 | A2 | 12/2008 |
| WO | 2009014970 | A1 | 1/2009 |
| WO | 2009022007 | A1 | 2/2009 |
| WO | 2009022008 | A1 | 2/2009 |
| WO | 2009022010 | A1 | 2/2009 |
| WO | 2009022020 | A1 | 2/2009 |
| WO | 2009026537 | A1 | 2/2009 |
| WO | 2009035969 | A1 | 3/2009 |
| WO | 2009076550 | A1 | 6/2009 |
| WO | 2009091082 | A1 | 7/2009 |
| WO | 2009124755 | A1 | 10/2009 |
| WO | 2009143020 | A1 | 11/2009 |
| WO | 2009143021 | A1 | 11/2009 |
| WO | 2010009243 | A1 | 1/2010 |
| WO | 2010022313 | A2 | 2/2010 |
| WO | 2010023594 | A1 | 3/2010 |
| WO | 2010040765 | A1 | 4/2010 |
| WO | 2010048358 | A2 | 4/2010 |
| WO | 2010092124 | A1 | 8/2010 |
| WO | 2010092125 | A1 | 8/2010 |
| WO | 2010092126 | A1 | 8/2010 |
| WO | 2010133638 | A1 | 11/2010 |

(56) References Cited

FOREIGN PATENT DOCUMENTS

| | | | |
|---|---|---|---|
| WO | 2010138535 | A1 | 12/2010 |
| WO | 2011039107 | A1 | 4/2011 |
| WO | 2011039108 | A2 | 4/2011 |
| WO | 2011039337 | A1 | 4/2011 |
| WO | 2011060290 | A2 | 5/2011 |
| WO | 2010092123 | A8 | 6/2011 |
| WO | 2011117295 | A1 | 9/2011 |
| WO | 2011120923 | A1 | 10/2011 |
| WO | 2011153712 | A1 | 12/2011 |
| WO | 2011153953 | A1 | 12/2011 |
| WO | 2012003811 | A1 | 1/2012 |
| WO | 2012062698 | A1 | 5/2012 |
| WO | 2012107476 | A1 | 8/2012 |
| WO | 2012110537 | A1 | 8/2012 |
| WO | 2012120040 | A1 | 9/2012 |
| WO | 2012140597 | A1 | 10/2012 |
| WO | 2012160218 | A1 | 11/2012 |
| WO | 2013040164 | A1 | 3/2013 |
| WO | 2013040165 | A1 | 3/2013 |
| WO | 2013079501 | A1 | 6/2013 |
| WO | 2013163675 | A1 | 11/2013 |
| WO | 2014016381 | A1 | 1/2014 |
| WO | 2014056197 | A1 | 4/2014 |
| WO | 2014068007 | A1 | 5/2014 |
| WO | 2014094544 | A1 | 6/2014 |
| WO | 2014161836 | A1 | 10/2014 |
| WO | 2014161838 | A1 | 10/2014 |
| WO | 2014184248 | A2 | 11/2014 |
| WO | 2014195966 | A2 | 12/2014 |
| WO | 2015063563 | A1 | 5/2015 |
| WO | 2015082389 | A1 | 6/2015 |
| WO | 2015091313 | A1 | 6/2015 |
| WO | 2015110402 | A1 | 7/2015 |
| WO | 2015139386 | A1 | 9/2015 |
| WO | 2015150299 | A2 | 10/2015 |
| WO | 2015173584 | A1 | 11/2015 |
| WO | 2016046150 | A1 | 3/2016 |
| WO | 2016104643 | A1 | 6/2016 |
| WO | 2016134486 | A1 | 9/2016 |
| WO | 2016135747 | A2 | 9/2016 |
| WO | 2017032799 | A1 | 3/2017 |
| WO | 2017155841 | A1 | 9/2017 |
| WO | 2017156632 | A1 | 9/2017 |
| WO | 2017174571 | A1 | 10/2017 |
| WO | 2018043463 | A1 | 3/2018 |
| WO | 2019051540 | A1 | 3/2019 |
| WO | 2019059557 | A2 | 3/2019 |
| WO | 2019121509 | A1 | 6/2019 |
| WO | 2020219645 | A2 | 10/2020 |
| WO | 2021078964 | A1 | 4/2021 |
| WO | 2021092341 | A1 | 5/2021 |
| WO | 2021105152 | A1 | 6/2021 |
| WO | 2021165177 | A1 | 8/2021 |
| WO | 2022015743 | A1 | 1/2022 |
| WO | 2022036506 | A1 | 2/2022 |
| WO | 2023006718 | A1 | 2/2023 |
| WO | 2023006745 | A1 | 2/2023 |
| WO | 2023006747 | A1 | 2/2023 |
| WO | 2023227492 | A1 | 11/2023 |
| WO | 20240184293 | A1 | 9/2024 |
| WO | 20240223388 | A1 | 10/2024 |
| WO | 2024240632 | A1 | 11/2024 |
| WO | 2024240633 | A1 | 11/2024 |

OTHER PUBLICATIONS

Malik et al., "Permethrin Spot On Intoxication Of Cats: Literature review and survey of veterinary practitioners in Australia", Journal of Feline Medicine and Surgery, vol. 12, 2010, pp. 5-14.

Mamidi, et al., "Metabolism And Excretion Of Canagliflozin In Mice, Rats, Dogs, And Humans." Drug Metabolism and Disposition 42.5 (2014): 903-916.

Maruo, et al. "Polymorphism of UDP-glucuronosyltransferase and drug metabolism." Current drug metabolism 6.2 (2005): 91-99.

Mathur et al. "Evaluation of a Technique of Inducing Hypertensive Renal Insufficiency in Cats", AJVR, vol. 65, No. 7, Jul. 2004, pp. 1006-1013, 8 pages.

Matsuhisa et al., Diabetes, The Effect of Pioglitazone on Hepatic Glucose Uptake Measured With Indirect and Direct Methods in Alloxan-Induced Diabetic Dogs, vol. 46, Feb. 1997,p. 224-231.

Matsumura, et al., "Effect Of Sodium Glucose Cotransporter 2 Inhibitors On Cardiac Function And Cardiovascular Outcome: A Systematic Review." Cardiovascular Ultrasound 17.1 (2019): 1-6.

Maynou, et al., "Effects Of Oral Administration Of Acidogenic Boluses At Dry-Off On Performance And Behavior Of Dairy Cattle", Journal of Dairy Science, vol. 101, No. 12, 2018, pp. 1-12.

McGowan et al., "Serum Insulin Concentrations in Horses with Equine Cushing's Syndrome: Response to a Cortisol Inhibitor and Prognostic Value" Equine Veterinary Journal vol. 36 issue 3 pp. 295-298 (Year:2004).

McGowan, Catherine M., "Diagnosis And Treatment Of Equine Crushing Syndrome." The Veterinarian, Clinical Review, Jan. 26, 2005, pp. 1-5.

McGowan, et al., Clinical Endocrinology of Companion Animals, 2013, 1st ed, John Wiley & Cons, Inc. pi. 100-114.

Mchale, Mary "Grignard Reaction" Connexions module: m15245, (2007) pp. 1-18.

Mclaughlin, et al., "Suzuki-Miyaura Cross-Coupling of Benzylic Phospahates with Arylboronic Acids"; Organic Letters (2005) vol. 7 No. 22 pp. 4875-4878.

McMaster University, Chem2006 Lab Manual, 1997/98, Expt 1, Part B, Recrystallization and Melting Point Determinations, pp. 1-9.

McMurray, et al., "A Trial To Evaluate The Effect Of The Sodium-Glucose Co-Transporter 2 Inhibitor Dapagliflozin On Morbidity And Mortality In Patients With Heart Failure And Reduced Left Ventricular Ejection Fraction (DAPA-HF)." European Journal of Heart Failure 21.5 (2019): 665-675.

Meng, et al., "Discovery of Dapagliflozin: A Potent, Selective Renal Sodium-Dependent Glucose Cotransporter 2 (SGLT2) Inhibitor for the Treatment of Type 2 Diabetes" J. Med. Chem. (2008) vol. 51, pp. 1145-1149.

Merck Manual Online Edition, "Diabetes Mellitus"http://www.merckmanuals.com/home/print/hormonal_and_metabolic_disorders/diabetes . . . Sep. 13, 2011, last revision Jun. 2008 by Preeti Kishore M.D.

Merriam-Webster's Collegiate Dictionary, definition of prevent, published 1998 by Merriam-Webster Inc. p. 924.

Mew et al., "Urea Cycle Disorders Overview." Genereviews, 2003, pp. 1-24. [Accessed at: http://www.ncbi.nlm.nih.gov/books/NBK1217/?report=printable on Sep. 9, 2016].

Mishina, et al., "Non-Invasive Blood Pressure Measurements In Cats: Clinical Significance Of Hypertension Associated With Chronic Renal Failure." Journal of Veterinary Medical Science 60.7 (1998): 805-808.

Mooradian, et al., "Narrative Review: A Rational Approach to Starting Insulin Therapy" (2006) Annals of Internal Medicine, vol. 145, pp. 125-134.

Nair, et al., "Dose translation between laboratory animals and human in preclinical and clinical phases of drug development." Wiley Periodicals, Inc., Drug development research 79.8 (2018): 373-382.

Neamati, et al., "Depsides and Depsidones as Inhibition of HIV-1 Integrase: Dimvery of Novel Inhibitors Through 3D Database Searching", J. Med. Chem., 1997, vol. 40, pp. 942-951.

Nelson, R. W. "Oral medications for treating diabetes mellitus in dogs and cats." Journal of small animal practice 41.11 (2000): 486-490.

Nishinarita, et al. "Canagliflozin suppresses atrial remodeling in a canine atrial fibrillation model." Journal of the American Heart Association, 2021; 10:e017483. DOI: 10.1161/JAHA.119.017483, pp. 1-12.

Nobre, et al., "Synthesis of Diarylmethane Derivatives from Pd-Catalyzed Cross-Coupling Reactions of Benzylic Halides with Arylboronic Acids"; Tetrahedron Letters (2004) vol. 45, 8225-8228.

(56) References Cited

OTHER PUBLICATIONS

Nommsen-Rivers et al., "Feasibility and Acceptability of Metformin to Augment Low Milk Supply: A Pilot Randomized Controlled Trial", Journal of Human Lactation, vol. 35, No. 2, 2019, pp. 261-271.
Non Final Office Action dated Apr. 2, 2008 from U.S. Appl. No. 11/674,839, filed Feb. 14, 2007.
Non Final Office Action dated Apr. 2, 2008 from U.S. Appl. No. 11/742,612, filed May 1, 2007.
Non-Final Office Action dated Jun. 24, 2008 from U.S. Appl. No. 11/406,971, filed Apr. 19, 2006.
Non-Final Office Action dated Jun. 5, 2008 from U.S. Appl. No. 11/408,899, filed Apr. 21, 2006.
Non-Final Office Action dated May 8, 2008 from U.S. Appl. No. 11/359,846, filed Feb. 22, 2006.
Norikazu et al., "Comparison Of Angiotensin II Receptor Antagonists And Angiotensin Converting Enzyme Inhibitors On A Dog Suffering Mild Mitral Insufficiency". Annual Meeting of the Japanese Society of Veterinary Science, vol. 137, 2004, p. 140.
Notice of Allowance and Fee(s) Due dated Jan. 13, 2009 from U.S. Appl. No. 11/304,284, filed Dec. 15, 2005.
Notice of Allowance and Fee(s) Due dated Dec. 30, 2008 from U.S. Appl. No. 11/674,839, filed Feb. 14, 2007.
Notice of Allowance and Fee(s) Due dated Feb. 3, 2009 from U.S. Appl. No. 11/359,846, filed Feb. 22, 2006.
Notice of Allowance and Fee(s) Due dated Jan. 2, 2009 from U.S. Appl. No. 11/742,612, filed May 1, 2007.
Obermeier et al., "In Vitro Characterization and Pharmacokinetics of Dapagliflozin(BMS-512148), a Potent Sodium• Glucose Cotransporter Type II Inhibitor, in Animals and Humans" Drug Metabolism And Disposition, 2010, pp. 405-414, vol. 38, No. 3.
O'Brien et al., "Immunohistochemical Morphometry Of Pancreatic Endocrine Cells In Diabetic, Normoglycemic Glucose-Intolerant And Normal Cats", J Comp Pathol, vol. 96, 1986, pp. 357-369.
Oku, et al., "T-1095, An Inhibitor or renal Na+-Glucose Cotransporters, May Provide a Novel Approach to Treating Diabetes"; Diabetes (1999) vol. 48 pp. 1794-1800.
Ono et al., "Characteristics of the Long-Acting Sartan Telmisartan" Circulation Control, vol. 23, No. 4, 2002, pp. 462-466.
Osorio, et al., "Effect Of Phlorizin On Sglt2 Expression In Kidney Of Diabetic Rats", Journal of Nephrology vol. 23(05) pp. 541-546 (Year: 2010).
Osto, et al., "Diabetes From Humans To Cats", General and Comparative Endocrinology, vol. 182, 2013, pp. 48-53.
Osweiler, et al., "Toxicological Concepts: Factors that Influence Toxicology", General Toxicological Principles, in Small Animal Toxicology, Elsevier, Inc., St. Louis, MO, 2006, p. A17.
Palm, et al., "Oral Hypoglycemics in Cats with Diabetes Mellitus", Veterinary Clinics of North America: Small Animal Practice, vol. 43, Issue 2, 2013, https://dx.doi.org/10.1016/j.cvsm.2012.12.002, 9 pages.
Panchapakeskan et al., "Effects of SGLT2 Inhibition in Human Kidney Proximal Tubular Cells-Renoprotection in Diabetic Nephropathy?" PLOS ONE vol. 8 issue 2 e54442 pp. 1-8, doi: 10.1371/journal.pone.0054442 (Year: 2013).
Paszkiewicz, Rebecca L., et al. "Dapagliflozin Improves Insulin Sensitivity In The Obese Prediabetic Canine." Diabetes 67. Supplement_1 (2018). p. 113-LB, XP55980990A.
Payne, et al., "Cardiomyopathy Prevalence In 780 Apparently Healthy Cats In Rehoming Centres (the CatScan study)." Journal of Veterinary Cardiology 17 (2015): S244-S257.
Payne, et al., "Prognostic Indicators In Cats With Hypertrophic Cardiomyopathy." Journal of Veterinary Internal Medicine 27.6 (2013): 1427-1436.
Perner, et al., "5,6,7-Trisubstituted 4-Aminopyrido[2,3-d]pyrimidines as Novel inhibitors of Adenosine Kinase"; Journal of Medicinal Chemistry (2003) vol. 46 pp. 5249-5257.
1765 report from EP examination proceedings, p. 1-3, 2018.
Abdul-Ghani, et al. "Efficacy and Safety of SGL T2 Inhibitors in the Treatment of Type 2 Diabetes Mellitus". Curr Diab Rep vol. 12 pp. 230-238 DOI 10.1007/s11892-012-0275-6 (Year: 2012).
Abdul-Ghani, et al., "Role of sodium-glucose cotransporter 2 (SGLT 2) inhibitors in the treatment of type 2 diabetes." Endocrine reviews vol. 32, No. 4 (2011): 515-531.
Abstract in English for EP2349272A1, Aug. 3, 2011.
Abstract in English for EP2675527A1, Dec. 25, 2013.
Abstract in English for JP2004196788A, Jul. 18, 2004.
Abstract in English for JP2004359630A, Dec. 24, 2004.
Abstract in English for JP2005060625A, Mar. 10, 2005.
Abstract in English for JP56039056A, Apr. 14, 1981.
Abstract in English for JP58164502A, Sep. 29, 1983.
Abstract in English for JPH11124392A, May 11, 1999.
Abstract in English for JPH11315034A1, Nov. 16, 1999.
Abstract in English of CN1765362A, May 3, 2006.
Adachi, et al."T-1095, a renal Na+-glucose transporter inhibitor, improves hyperglycemia in streptozotocin-induced diabetic rats." Metabolism-Clinical and Experimental 49.8 (2000): 990-995.
Adamson, et al. "The fate of sulphadimethoxine in primates compared with other species." Biochemical Journal 118.1 (1970): 41-45.
Aguillon, et al. "Synthetic Strategies toward SGLT2 Inhibitors" Org. Process Res. Dev., Mar. 30, 2018, pp. 467-488, vol. 22, No. 4.
Allen, Andrew L., "The Diagnosis of Acetaminophen toxicosis in cats"., The Canadian Veterinary Journal, vol. 44, No. 6, Jun. 2003, pp. 509-510.
Anker, et al., "Empagliflozin in Heart Failure with a Preserved Ejection Fraction" The New England Journal of Medicine, 2021, vol. 383, No. 16, 1451-1461.
Arora, et al., "A Review on Pharmaceutical Suspension and Its Advancement," Annals of Clinical Case Reports, vol. 7, Article 2321, Oct. 25, 2022, 1-7 pages.
Asano, et al., "SGLT as a therapeutic target". Drugs of the Future, 2004, pp. 461-466, vol. 29, No. 5.
Asiedu-Gyekye, et al. "Does Losartan Prevent Cerebral Edema? A Preliminary Study Using A Vascular Compartment Model", www.MedSciMonit.com, Med Sci Monit, 2003; 9(3): BR127-130, Department of Pharmacology, University of Ghana Medical School, pp. BR127-BR130.
Asplin, et al.," Induction of laminitis by prolonged hyperinsulinaemia in clinically normal ponies". The Veterinary Journal vol. 174 pp. 530-535 (Year:2007).
Assessment Report Forxiga Dapagliflozin, European Medicines Agency, Science Medicines Health, 2012. pp. 1-170.
Assessment Report Jardiance Empagliflozine, European Medicines Agency, Science Medicines Health, 2014, pp. 1-99.
Assessment Report Invokana Canagliflozin, European Medicines Agency, Science Medicines Health, 2013, pp. 1-115.
Atkins, et al. "Risk factors, clinical signs, and survival in cats with a clinical diagnosis of idiopathic hypertrophic cardiomyopathy: 74 cases (1985-1989)." Journal of the American Veterinary Medical Association 201.4 (1992): 613-618.
Ault, Addison "Techniques and experiments for organic chemistry" University Science Books, 1998, pp. 59-60.
Azzalin, et al., "Inhibitors of GLUT/SLC2A Enhance the Action of BCNU and Temozolomide against High-Grade Gliomas," Neoplasia, vol. 19, No. 4, 2017, pp. 364-373.
Barreras, "Angiotensin II receptor blockers", Baylor University Medical Center Proceedings, 2003, pp. 123-126, 16:1.
Belanger-Quintana, et al., "Up to date knowledge on different treatment strategies for phenylketonuria" Molecular Genetics and Metabolism, vol. 104, No. 0, 2011, pp. S19-S25.
Benhaddou, et al "Tetra-n-Propylammonium Tetra-Oxoruthenate(VII): A Reagent of Choice for the Oxidation of Diversely Protected Glycopyranoses and Glycofuranoses to Lactones"; Carbohydrate Research (1994) vol. 260 pp. 243-250.
Berny, et al., "Animal Poisoning in Europe. Part 2: Companion Animals". The Veterinary Journal, vol. 183, 2010, pp. 255-259.
Bertulat, et al., "Effect of a single injection of cabergoline at dry off on udder characteristics in high-yielding dairy cows", Journal of Dairy Science, vol. 100, No. 4, 2017, pp. 3220-3232.

(56) References Cited

OTHER PUBLICATIONS

Bjornvad, et al., "Evaluation of a nine-point body condition scoring system in physically inactive pet cats" AJVR, 2011, vol. 72, No. 4, pp. 433-437.
Boothe, D.M., Textbook, 2000, Elsevier Health Sciences, pp. 35-36, Appendix A http://store.elsevier.com/Small-Animal-Clinical-Pharmacology-and-Therapeutics/Dawn-Boothe/isbn-9780721605555/.
Borgeat, et al. "Time spent with cats is never wasted: lessons learned from feline acromegalic cardiomyopathy, a naturally occurring animal model of the human disease." PLoS One 13.3 (2018): e0194342, pp. 1-18.
Bradford et al., "Phlorizin Administration Increases Hepatic Gluconeogenic Enzyme mRNA Abundance but Not Feed Intake in Late-Lactation Dairy Cows", J. Nutr., vol. 135, 2005, pp. 2206-2211.
Buoncompagni, et., al, "Treatment of Systemic Hypertension Associated With Kidney Disease." Vetlearn.com, Compendium: Contin Educ Vet, (2013): pp. E1-E6.
Burchell et al., "Safety and efficacy of dapagligflozin, a novel antidiabetic drug, in healthy cats", Abstract, JVM, vol. 32, 2018, p. 588.
Burnier, et al., "Angiotensin II receptor antagonists". The Lancet, vol. 355, 2000, pp. 637-645.
Byrn, Stephen et al. "Pharmaceutical Solids: A Strategic Approach to Regulatory Considerations" Pharmaceutical Research, vol. 12, No. 7, (1995) pp. 945-954.
Caldwell, et al. "Drug metabolism in exotic" animals. European Journal of Drug Metabolism and Pharmacokinetics 3 (1978): 61-66.
Caldwell, et., al., "Species differences in xenobiotic conjugation." Xenobiotic Metabolism and Disposition, eds Kato R., Estabrook RW, Cayen MN (Taylor & Francis, London, UK) (1989): 217-224.
Carrillo-Carrasco, et al., "Disorders of Intracellular Cobalamin Metabolism." GeneReviews, 2008, pp. 1-30. [Accessed at: http://www.ncbi.nlm.nih.gov/books/NBK1328/?report=printable on Sep. 9, 2016].
Champion, et al. "Analysis of the Effects of Candesartan on Responses to Angiotensin II in the Hindquarters Vascular Bed of the Cat", Journal of the American Society of Nephrology, 1999, S101-S103, 3 pages.
Chan, et al., "Comparative effects of phlorizin and phloretin on glucose transport in the cat kidney" American Journal of Physiology, 1962, pp. 975-979, vol. 203, No. 6.
Chao, et al., "Dapagliflozin: an evidence-based review of its potential in the treatment of type-2 diabetes" Core Evidence vol. 7 pp. 21-28, DOI: 10.2147/CE.S16359 (Year: 2012).
Chapter 3. Vse o zidkostah [Everything about liquids]. (Aug. 14, 2012). [Accessed at http://www.elbasio.ru/articles/Glava_3_V se_o_zhidkostjah].
Cingolani et al. "The Positive Inotropic Effect of Angiotensin II: Role of Endothelin-1 and Reactive Oxygen Species", Hypertension, Journal of the American Heart Association, 2006, [Accessed at: http://hyper.ahajournals.org/cgi/content/full/47/4/727],p. 726-734.
Ciobotaru, Emilia, "Diabetes Mellitus- Insights and Perspectives", Editor: Oluwafemi O. Oguntibeju, ISBN 978-953-51-0939-6, Jan. 2, 2013, Chapter 15, Spontaneous Diabetes Mellitus in Animals, pp. 271-296.
Communication of a Notice of Opposition and Consolidated List EPO in counterpart European Application No. 21155065.2-1109, mailed Jul. 31, 2024, p. 1-67.
Conlon, Peter D., "Nonsteroidal Drugs Used in the Treatment of Inflammation". Clinical Pharmacology, vol. 18, No. 6, 1988, pp. 1115-1131.
Coronel et al., "Hypertension Treatment in Nondiabetic Advanced Chronic Kidney Disease Patients with Irbesartan. Effect on Serum Uric Acid". Abstract, Journal of Hypertension, vol. 23, Supp_ 2, 2005, p. S65.
Court "Feline drug metabolism and disposition: pharmacokinetic evidence for species differences . . .", Vet Clin North Am Small Anim Pract, 43(5), Sep. 2013, pp. 1-20.
Court et al., "Molecular Basis for Deficient Acetaminophen Glucuronidation in Cats an Interspecies Comparison of Enzyme Kinetics in Liver Microsomes," Biochemical Pharmacology, vol. 53. pp. 1041-1047, 1997.
Court et al., "Molecular genetic basis for deficient acetaminophen glucuronidation by cats: UGT1A6 is a Jseudogene, and evidence for reduced diversity of expressed hepatic UGT1A isoforms". Pharmacogenetics, vol. 10, JOOO, pp. 355-369.
Custodio, et al. "SGLT2 inhibition and heart failure-current concepts." Heart Failure Reviews 23 (2018): p. 409-418.
De Champlain, Jacques. "Do angiotensin II antagonists provide benefits beyond blood pressure reduction?." Advances in therapy 22 (2005): 117-136.
De Laat et al., "Equine laminitis: Induced by 48 h hyperinsulinaemia in Standardbred horses". Equine Veterinary Journal, vol. 42, No. 2, 2010, pp. 129-135.
Deacon, Carolyn F. "Perspectives in Diabetes Therapeutic Strategies Based on Glucagon-Like Peptide 1" Diabetes, (2004) vol. 53 pp. 2181-2189.
Decision of Invalidation Request, Decision No. 42795, China National Intellectual Property Administration of People's Republic of China, 2020, p. 1-12.
Declaration of Matthias Eckhardt, Mar. 6, 2019, p. 1-5.
Declaration Under 37 C.F.R. § 1.132 by Dania Birte Reiche, Jul. 9, 2019,p. 1-7.
Declaration Under 37 C.F.R. §1.132 by Tobias Warnken, dated Feb. 27, 2025, p. 1-11.
Definition of prevent, Oxford English Dictionary Online, [Accessed at: http://dictionary.oed.com/, especially definition 9a. at p. 2.] (Year:2010).
Dekkers, et al., "Sodium-glucose cotransporter 2 inhibitors: extending the indication to non-diabetic kidney disease." Nephrology Dialysis Transplantation, vol. 35, (2020): pi33-i42.
Deshpande et al., "A Practical Stereoselective Synthesis and Novel Cocrystallizations of an Amphiphatic SGLT-2 Inhibitor". Organic Process Research & Development, vol. 16, 2012, pp. 577-585.
Diabetes, Abstract Book, 67th Scientific Sessions, Journal of the American Diabetes Association, Jun. 2007, vol. 56 Supplement 1, pp. A144-A145.
Dohan et al., "Lesions of the Pancreatic Islets Produced in Cats by Administration of Glucose" Science, 1947, p. 183, vol. 105, No. 2720, [Accessed at: https://www.jstor.org/stable/1674617, Jan. 7, 2024 07:41 +00:00.
Dohle, et al., Copper-Mediated Cross-Coupling of Functionalized Arylmagnesium Reagents with Functionalized Alkyl and Benzylic Halides; Organic Letters (2001) vol. 3 No. 18 p. 2871-2873.
Drug Watch "Type 2 Diabetes Mellitus" Formulary vol. 43 Aug. 2008 p. 304.
Duez et al., "DPP-4 inhibitors in the treatment of type 2 diabetes" Biochemical Pharmacology vol. 83 pp. 823-832, doi:10.1016/j.bcp.2011.11.028 (Year: 2011).
Durham et al., "The effect of metformin on measurements of insulin sensitivity and β-cell response in 18 horses and ponies with insulin resistance", Equine Veterinary Journal, vol. 40, No. 5 pp. 493-500 DOI 10.2746/042516408X273648 (Year: 2008).
Durham et al., "Type 2 diabetes mellitus with pancreatic b cell dysfunction in 3 horses confirmed with minimal model analysis". Equine Veterinary Journal, vol. 41, No. 9, 2009, pp. 924-929.
Ebner et al., "Disposition and Chemical Stability of Telmisartan 1-O-Acylglucuronide," The American Society for Pharmacology and Experimental Therapeutics, Drug Metabolism and Disposition, 1999, vol. 27, No. 10, pp. 1143-1149.
Ebner, et al. "In vitro glucuronidation of the angiotensin II receptor antagonist telmisartan in the cat: a comparison with other species." Journal of Veterinary Pharmacology and Therapeutics 36.2 (2013): 154-160.
Elischer, Melissa, "History of dairy cow breeds: Holstein", The Holstein Dairy Cow, Michigan State University Extension, Apr. 4, 2016, 2 pages.
Elkinson, et al., "Canagliflozin: first global approval." Drugs 73.9 (2013): 979-988.

(56) References Cited

OTHER PUBLICATIONS

Emmerich IU, "New drugs for small animals in 2012", Tierärztliche Praxis, Ausgabe K, Kleintiere/heimetiere, 42(4), Jan. 1, 2013, pp. 237-243.
Emmerich IU, "New drugs for small animals in 2012", Tieraztliche Praxis, Ausgabe K, Kleintiere/heimetiere, 42(4), Jan. 1, 2013, pp. 237-243_Abstract.
Ettinger Feldman 2005_Textbook Ref, Section VI, Therapeutic Considerations in Medicine and Disease, Veterinary Internal Medicine, 6. Edition, vol. 1, p. 530-531.
Excerpt from Chapter 14 of Basiswissen Physik, Chemie und Biochemie, 3rd ed., 2013.
Experimental report, Methods & Results, "Canine Lab Model of Diabetes mellitus in dogs", 1993, p. 1-2.
Extended European Search Report for European Application No./Patent No. 23175197.5, Dated Nov. 17, 2023, p. 1-8.
Extended European Search Report for European Patent Application No. 24204085.5, Dated Feb. 4, 2025, p. 1-11.
Frank et al., "Equine Metabolic Syndrome", ACVIM Consensus Statement, Journal of Veterinary Internal Medicine, vol. 24, No. 3, Apr. 2, 2010, pp. 467-475.
Frank et al., "Insulin dysregulation", Equine Veterinary Journal, Year 2013, vol. 46, pp. 103-112.
Frank et al.: "Equine Metabolic Syndrome", Journal of Equine Veterinary Science, 2009, pp. 259-267, vol. 29 No. 5.
Freeman, et al. "Feline hypertrophic cardiomyopathy: a spontaneous large animal model of human HCM." Cardiology research 8.4 (2017): 139-142.
French, et al., "Pharmacokinetics and Metabolic Effects of Triamcinolone Acetonide and Their Possible Relationships to Glucocorticoid-Induced Laminitis in Horses." Journal of Veterinary Pharmacology and Therapeutics, vol. 23, No. 5, 2000, pp. 287-292.
Fuerstner, et al., "Practical Method for the Rhodium-Catalyzed Addition of Aryl- and Alkenylboronic Acids to Aldehydes"; Advanced Synthesis and Catalysis (2001) vol. 343 No. 4 pp. 343-350.
Fujimori, et al., "Remogliflozin etabonate, in a novel category of selective low-affinity sodium glucose cotransporter (SGL T2) inhibitors, exhibits antidiabetic efficacy in rodent models." Journal of Pharmacology and Experimental Therapeutics 327 , No. 1 (2008): 268-276.
Gallo et al., "Probing SGLT2 as a therapeutic target for diabetes: Basic physiology and consequences" Diab Vasc Dis Res., Mar. 2015, pp. 78-89, vol. 12, No. 2.
Garrison, et al., "[Pro11,D-Ala 12]angiotensin I has rapid onset vasoconstrictor activity in the cat", Am J Physiol Endocrinol Metab 273: 1059-1064, 1997, 7 pages.
Gehlen et al., "Comparison of Insulin and Glucose Metabolism in Horses with Pituitary Pars Intermedia Dysfunction Treated Versus Not Treated with Pergolide". Journal of Equine Veterinary Science, vol. 34, 2014, pp. 508-513.
Ghassemi et al., "Synthesis and properties of new sulfonated poly(p-phenylene) derivatives for proton exchange membranes" Polymer (2004) pp. 5847-5854.
Grauer (ACE Inhibitors and CKD; accessed online Feb. 5, 2015), 2 pages.
Greco, "Treatment Of Feline Type 2 Diabetes Mellitus With Oral Hypoglycemic Agents" OMVA Conference Proceedings pp. 49-52 (Year: 2005).
Greco, et al. "Segregation of Active Constituents from Tablet Formulations During Grinding: Theoretical Considerations" Drug Development and Industrial Pharmacy, (1982) 8(4), pp. 565-578.
Grempler et al., "Empagliflozin, a novel selective sodium glucose cotransporter-2 (SGLT-2) inhibitor: characterisation and comparison with other SGLT-2 inhibitors." Diabetes, Obesity and Metabolism, vol. 14, 2012, pp. 83-90.
English Abstract for CN111870694B.
Perrier et al., "In vitro N-glucuronidation of SB 47436 (BMS 186295), a new AT1 nonpeptide angiotensin II receptor antagonist, by rat, monkey and human hepatic microsomal fractions." Abstract, The Journal of Pharmacology and Experimental Therapeutics, vol. 271, No. 1, Oct. 1994, pp. 91-99 (p. A-10).
Pershadsingh, et al., "Insulin-Sensitizing Effects Of Telmisartan: Implications For Treating Insulin-Resistant Hypertension And Cardiovascular Disease." Diabetes Care 27.4 (2004): 1015-1016.
Piya, et al. "Emerging Treatment Options For Type 2 Diabetes" British Journal of Clinical Pharmacology, (2010) vol. 70, No. 5, pp. 631-644.
Polzin, David, "Treating Feline Kidney Disease: An Evidence-Based Approach". North American Veterinary Conference Proceedings, Jan. 7, 2006, pp. 1-6. [Accessed at http://www.iknowledgenow.com/article.cfm?documentID=2817&transactionKey . . . on Dec. 16, 2014].
Powell et al., "Effect of LX4211 on Glucose Homeostasis and Body Composition in Preclinical Models" J Pharmacol Exp Ther vol. 350 pp. 232-242, 10.1124/jpet.114.214304 (Year: 2014).
Printz, et al., "Tweaking the Glucose Sensor: Adjusting Glucokinase Activity with Activator Compounds", Endocrinology, (2005) vol. 146, No. 9, pp. 3693-3695.
Rainier, et al. , "Aluminum- and Boron-Mediated C-Glycoside Synthesis from 1,2-Anhydroglycosides" Organic Letters, (2000) vol. 2, No. 17, pp. 2707-2709.
Rand et al., "Management Of Feline Diabetes Mellitus" Veterinary Clinics Of North America: Small Animal Practice vol. 31 No. 5 pp. 881-913 (Year: 2001).
Rand, Jacquie S. "Pathogenesis of Feline Diabetes." Veterinary Clinics of North America: Small Animal Practice, vol. 43, No. 2, 2013, pp. 221-231.
Randzio, et al., "Metastability and Instability of Organic Crystalline Substances" J. Phys. Chem. (2008) 112, pp. 1435-1444.
Redenti, et al. "Drug/Cyclodextrin/Hydroxy Acid Multicomponent Systems. Properties and Pharmaceutical Applications" Journal of Pharmaceutical Sciences, (2000) vol. 89, No. 1, pp. 1-8.
Reilly et al., "Carcinogenicity Risk Assessment Supports the Chronic Safety of Dapagliflozin, an Inhibitor of Sodium-Glucose Co-Transporter 2, in the Treatment of Type 2 Diabetes Mellitus" Diabetes Therapy vol. 5 pp. 73-96, DOI 10.1007/s13300-014-0053-3 (Year: 2014).
Remuzzi, Giuseppe, et al. "The Role Of Renin-Angiotensin-Aldosterone System In The Progression Of Chronic Kidney Disease." Kidney International 68 (2005): S57-S65.
Response dated Nov. 5, 2008 to Non-Final Office Action dated May 8, 2008 from U.S. Appl. No. 11/359,846, filed Feb. 22, 2006.
Response dated Sep. 25, 2008 to Non-Final Office Action dated Apr. 2, 2008 from U.S. Appl. No. 11/674,839, filed Feb. 14, 2007.
Response dated Sep. 25, 2008 to Non-Final Office Action dated Apr. 2, 2008 from U.S. Appl. No. 11/742,612, filed May 1, 2007.
Revesz, et al., "SAR of Benzoylpyridines and Benzophenones as p38α MAP Kinase Inhibitors with Oral Activity"; Bioorganic & Medicinal Chemistry Letters (2004) vol. 14 pp. 3601-3605.
Rodriguez-Iturbe et al., "Early treatment with cGMP phosphodiesterase inhibitor ameliorates progression of renal damage" Kidney International, vol. 68, 2005, pp. 2131-2142.
Rosenstock et al., "Effects of Dapagliflozin, an SGLT2 Inhibitor, on HbA1c, Body Weight, and Hypoglycemia Risk in Patients With Type 2 Diabetes Inadequately Controlled" Diabetes Care vol. 35 pp. 1473-1478 (Year: 2012).
Rossetti et al., "Correction of hyperglycemia with phlorizin normalizes tissue sensitivity to insulin in diabetic rats" The Journal of Clinical Investigation, 1987, pp. 1510-1515, vol. 79, No. 5.
Rudnic, et al., "Oral Solid Dosage Forms" Remington—The Science and Practice of Pharmacy, 21th Ed, (2005) Chapter 45, Multiple Compressed Tablets, p. 890.
Rush, et al., "Population and survival characteristics of cats with hypertrophic cardiomyopathy: 260 cases (1990-1999)." Journal of the American Veterinary Medical Association 220.2 (2002): 202-207.
Ryšavá, et al. "Effect Of Telmisartan On Blood Pressure Control And Kidney Function In Hypertensive, Proteinuric Patients With Chronic Kidney Disease." Blood pressure monitoring 10.4 (2005): 207-213.

(56) References Cited

OTHER PUBLICATIONS

Sako et al.; "Time-Action Profiles Of Insulin Detemir In Normal And Diabetic Dogs" Research in Veterinary Science, vol. 90, p. 396-403, 2011.
Santos-Gallego, et al. "Empagliflozin Ameliorates Adverse Left Ventricular Remodeling In Nondiabetic Heart Failure By Enhancing Myocardial Energetics." Journal of the American College of Cardiology 73.15 (2019): 1931-1944.
Schiweck et al., "Sugar Alcohols". Ullmann's Encyclopedia of Industrial Chemistry, Wiley-VCH Verlag GmbH & Co. KGaA, Weinheim, 2012, pp. 1-37.
Schlienger et al., "De l'ecorce des racines du pommier aux inhibiteurs du transporteur sodium-glucose de type 2 : sGLT2) : la folle histoire de la phloridzine" Medecine des Maladies Metaboliques, 05, Dec. 2023, pp. 280-286, vol. 18, No. 3.
Schlienger et al., From the bark of apple tree roots to sodium-glucose transporter type 2 inhibitors (sGLT2): the crazy story of phloridzin. Medicine of Metabolic Diseases, Dec. 5, 2023, pp. 280-286, vol. 18, No. 3., Machine translation May 2024.
Seman, et al., "Empagliflozin (BI 10773), a Potent and Selective SGLT2 Inhibitor, Induces Dose-Dependent Glucosuria in Healthy Subjects" (2013) Clinical Pharmacology in Drug Development, vol. 2, Issue 2, 20 pgs.
Sent et al., "Comparison of Efficacy of Long-term Oral Treatment with Telmisartan and Benazepril in Cats with Chronic Kidney Disease." Journal of Veterinary Internal Medicine, vol. 29, (2015): 1479-1487.
Sent, Dr. Ulrike, Second Declaration to 37 C.F.R. §1.132, Mar. 22, 2011.
Sent, Dr. Ulrike_Declaration, Pursuant to 37 C.F.R. §1.132 Mar. 19, 2009.
Sharma, "Telmisartan in patients with mild/moderate hypertension and chronic kidney disease." Clinical nephrology 63.4 (2005): p. 1-8.
Sherwin, et al., "The Prevention or Delay of Type 2 Diabetes" Diabetes Care, (2002) vol. 25, No. 4, pp. 742-749.
Sidransky, E., "Gaucher Disease: Insights from a Rare Mendelian Disorder." Discovery Medicine, vol. 14, No. 77, Oct. 2012, pp. 273-281.
Silverman, et al. "Handbook of Grignard Reagents" Marcel Dekker (1996) p. 82.
Singhal, et al. "Drug Polymorphism And Dosage Form Design: A Practical Perspective" Advanced Drug Delivery Reviews, 56, (2004) pp. 335-347.
Sinha et al., "Pioglitazone—Do we really need it to manage type 2 diabetes?" Diabetes & Metabolic Syndrome: Clnical Research & Reviews, vol. 7, No. 1, 2013, pp. 52-55.
Smith, et al., "Pharmacology of Nonpeptide Angiotensin II Receptor Antagonists", Annu. Rev. Pharmacol. Toxicol., 1992, pp. 135-165, vol. 32.
Snively et al., "Chronic Kidney Disease: Prevention and Treatment of Common Complications". American Family Physicians, vol. 70, No. 10, Nov. 2004m pp. 1921-1928.
Sommer, et al., "Displacement Of Halogen Of 2-Halogeno-Substituted Benzonitriles With Carbonions. Preparation Of (2-Cyanoaryl)Arylacetonitriles"; Journal of Organic Chemistry (1990) vol. 55 pp. 4817-4821.
Sparkes, et al., "ISFM Consensus Guidelines on the Practical Management of Diabetes Mellitus in Cats", Journal of Feline Medicine and Surgery, 17(3), 2015, pp. 235-250.
Stazi, et al., "Statistical Experimental Design-Driven Discovery of room-Temperature Conditions for Palladium-Catalyzed Cyanation of Aryl Bromides"; Tetrahedron Letters (2005) vol. 46 1815-1818; Elsevier Ltd.
Stebbins, et al., "Spinal Angiotensin II Influences Reflex Cardiovascular Responses to Muscle Contraction", American Journal Of Physiology, vol. 269, No. 4, Part 2, 1995 pp. R864-R868.
Submission Forwarding D30, Amendment in Response to Final Office Action dated Jan. 7, 2019, U.S. Appl. No. 15/113,127.
Suga et al., "Angiotensin II Type 1 Receptor Blockade Ameliorates Tubulointerstitial Injury Induced By Chronic Potassium Deficiency". 2002, Kidney International, vol. 61, pp. 951-958.
Suga et al., "SGL T1 in pancreatic a cells regulates glucagon secretion in mice, possible explaining the distinct effects of STGL T2 inhibitors on plasma glucagon levels", Molecular Metabolism 19 (2018), 12 pages.
Sugimoto et al., "Novel Therapeutic Agents for the Treatment of Diabetes Sodium-Glucose Co-Transporter (SGLT) 2 Inhibitors." Cutting-Edge of Medicine, vol. 102, No. 6, 2013, pp. 1474-1483.
Sugiyama, et al. "Telmisartan Inhibits Both Oxidative Stress And Renal Fibrosis After Unilateral Ureteral Obstruction In Acatalasemic Mice." Nephrology Dialysis Transplantation 20.12 (2005): 2670-2680.
Supplement to: Anker, et al., "Empagliflozin In Heart Failure With A Preserved Ejection Fraction." New England Journal of Medicine 385.16 (2021): 1451-1461.
International Search Report for PCT/EP2007/060531 mailed May 19, 2008.
International Search Report for PCT/EP2018/085193, Jun. 27, 2019.
Isaji, Masayuki "Sodium-glucose cotransporter inhibitors for diabetes" Current Opinion in Investigational Drugs, (2007) vol. 8, No. 4, pp. 285-292.
Israili, Z.H., "Clinical pharmacokinetics of angiotensin II (AT1) receptor blockers in hypertension". Journal of Human Hypertension, vol. 14, Suppl. 1, 2000, pp. S73-S86.
Jagdmann Jr, G. Erik ; Synthesis of 5-(4-Substituted Benzyl)-2,4-Diaminoquinazolines as Inhibitors of *Candida albicans* Dihydrofolate Reductase; Journal Heterocyclic Chemical (1995) vol. 32 pp. 1461-1465.
Jamil et al. "Acid Maltase Deficiency-Pompe's Disease." Journal of Pakistan Medical Association, vol. 61, No. 8, 2011, pp. 821-823.
Jensen, et al., "Plasma renin activity and angiotensin I and aldosterone concentrations in cats with hypertension associated with chronic renal disease." American Journal of Veterinary Research 58.5 (1997): 535-540.
Jiapu et al., "Small Animal Diseases", Beijing Agricultural University Press, Apr. 1993, the first edition, first print, pp. 6-10.
Johnson et al., "Insulin Resistance, and Metabolic Syndrome in Horses", Journal diabetes SciTechnol, (2012), vol. 6 (3), pp. 534-540.
Johnson et al., "Medical Implications of Obesity in Horses-Lessons for Human Obesity." Journal of Diabetes Science and Technology, vol. 3, No. 1, Jan. 2009, pp. 163-174.
Kadowaki, T et al. "PPAR gamma agonist and antagonist" Nihon Yakurigaku Zasshi (2001) vol. 118, No. 9, pp. 321-326.
Kadowaki, T et al. "PPAR gamma agonist and antagonist" Nihon Yakurigaku Zasshi (2001) vol. 118, No. 9, pp. 321-326. (English abstract).
Kakinuma et al., "(1S)-1,5-Anhydro-1-[5-(4-ethoxybenzyl)-2-methoxy-4-methylphenyl]-1-thio-d-glucitol (TS-071) is a Potent, Selective Sodium-Dependent Glucose Cotransporter 2 (SGLT2) Inhibitor for Type 2 Diabetes Treatment". Journal of Medicinal Chemistry, vol. 53, No. 8, 2010, pp. 3247-3261.
Kalgutkar, et al., "Preclinical species and human disposition of PF-04971729, a selective inhibitor of the sodium-dependent glucose cotransporter 2 and clinical candidate for the treatment of type 2 diabetes mellitus." Drug metabolism and disposition 39.9 (2011): 1609-1619.
Kaplan et al., Heart Failure Reviews, "Direct cardiovascular impact of SGL T2 inhibitors: mechanisms and effects", 2018, vol. 23, pp. 419-437.
Katsuno et al., "Sergliflozin, a Novel Selective Inhibitor of Low-Affinity Sodium Glucose Cotransporter (SGLT2), Validates the Critical Role of SGLT2 in Renal Glucose Reabsorption and Modulates Plasma Glucose Level." The Journal of Pharmacology and Experimental Therapeutics, vol. 320, No. 1, 2007, pp. 323-330.
Katsuno, et al., "Long-term Treatment with Sergliflozin Etabonate Improves Disturbed Glucose Metabolism in KK-Ay Mice." European Journal of Pharmacology 618.1-3 (2009): 98-104.

(56) References Cited

OTHER PUBLICATIONS

Katz et al., Equine Veterinary Journal, "A review of recent advances and current hypotheses on the pathogenesis of acute laminitis", vol. 44, pp. 752-761,DOI: 10.1111/j.2042-3306.2012.00664.x (Year: 2012).
Kemper et al., "Metabolism: A Determinant of Toxicology". Principles and Methods of Toxicology, 5th Edition, Chapter 3, Informa Healthcare USA, New York, NY, 2008, pp. 139-142.
Kidney Disease, The Medical Dictionary, (Accessed at: http://medical dictionary.thefreedictionary.com/kidney disease) Nov. 2015.
Knochel, et al., "Highly functionalized Organomagnesium Reagents Prepared through Halogen-Metal Exchange" Angew. Chem. Int. Ed. (2003) vol. 42, 4302-4320.
Koide et al., "Hypertrophic response to hemodynamic overload: role of load vs. renin-angiotensin system activation". American Journal of Physiology—Heart, vol. 276, 1999, pp. H350-H358.
Kondo et al., "Characterization of conjugated metabolites of a new angiotensin II receptor antagonist, candesartan cilexetil, in rats by liquid chromatography/electrospray tandem mass spectrometry following chemical derivatization." Abstract, Journal of Mass Spectrometry, vol. 31, No. 8, Aug. 1996, pp. 873-878 (p. A-11).
Koo, et al., 2-Pyridyl Cyanate: A Useful Reagent for he Preparation of Nitriles; Synthetic Communications (1996) vol. 26 No. 20 pp. 3709-3713; Marcel Dekker, Inc.
Krasovskiy, et al., "A LiCL-Mediated Br/Mg Exchange Reaction for the Preparation of Functionalized Aryl- and Heterarylmagnesium Compounds from Organic Bromides", Angew. Chem. Int. Ed. (2004) vol. 43, pp. 3333-3336.
Kumari et al. "Effect of Pre- and Posttreatment of Losartan in Feline Model of Myocardial Ischemic-Reperfusion Injury", Methods Find Exp Clin Pharmacol 2004, 26(1): 39-45, 8 pages.
Kuribayashi, et al., "Bis C-Glycosylated Diphenylmethanes for Stable Glycoepitope Mimetics"; Syntletters (1999) vol. 6 pp. 737-740.
Kuribayashi, et al., "C-Glycosylated Aryl tins: Versatile Building Blocks for Aryl C-Glycoside Glycomimetics"; J. Carbohydrate Chemistry (1999) vol. 18, No. 4 pp. 371-382.
Kuribayashi, et al., "C-Glycosylated Diphenylmethanes and Benzophenones: The Stille Coupling Reaction of C-Glycosylated Aryl tins with Benzyl Bromides and Acid Chlorides"; J. Carbohydrate Chemistry (1999) vol. 18, No. 4 pp. 393-401.
Kurosaki et al., "Ipragliflozin and other sodium-glucose cotransporter-2 (SGLT2) inhibitors in the treatment of type 2 diabetes: Preclinical and clinical data" Pharmacology & Therapeutics, Apr. 4, 2013, pp. 51-59, vol. 139.
Lanctôt S. et al., "Effect of intramammary infusion of chitosan hydrogels at drying-off on bovine mammary gland involution", Journal of Dairy Science, vol. 100, No. 3, 2017, pp. 2269-2281.
Langle, et al., "Selective Double Suzuki Cross-Coupling Reactions. Synthesis of Unsymmetrical Diaryl (or Heteroaryl) Methanes"; Tetrahedron Letters (2003) vol. 44, pp. 9255-9258; Pergamon Press.
Lau et al., "Effects of Diabetes Mellitus on Lactation in the Rat", Diabetes and Lactation, vol. 204, 1993, pp. 81-89.
Lazaro et al., "Forum Original Research Communication: Long-Term Blood Pressure Control Prevents Oxidative Renal Injury" Antioxidants & Redox Signaling, vol. 7, Nos. 9 & 10, 2005, pp. 1285-1293.
Lefebvre, et al., "Angiotensin-Converting Enzyme Inhibitors In The Therapy Of Renal Diseases", Journal of Veterinary Pharmacology and Therapeutics, vol. 27, 2004, pp. 265-281.
Li et al., "Efficacy Evaluation Of Telmisartan In Treatment Of Dilated Cardiomyopathy With Heart Failure", Chinese Heart Journal, vol. 18, No. 4, 2006, pp. 427-429_Chinese and Abstract in English.
Li et al., "Progress in Drug Therapy for Dilated Cardiomyopathy", Chinese Medical Abstracts—Geriatrics, 2002, vol. 11, No. 1, pp. 69-72.
Li, et al., "Lack of Pharmacokinetic Interaction between Dapagliflozin and Pioglitazone in Healthy Subjects" Journal of Clinical Pharmacology, (2009) vol. 49, No. 9, pp. 1093.
Liang, et al., "Effect of canagliflozin on renal threshold for glucose, glycemia, and body weight in normal and diabetic animal models." PloS one 7.2 (2012): e30555, 7 pages.
Liang, et al.,"JNJ-28431754/TA-7284, An SGLT Inhibitor, Lowers Blood Glucose And Reduces Body Weight In Obese And Type 2 Diabetic Animal Models." Diabetes. vol. 58. Supp. Suppl. 1A. Abstract No. 534-P (Year 2009).
Lim et al., "Angiotensin II Blockade Reverses Myocardial Fibrosis in a Transgenic Mouse Model of Human Hypertrophic Cardiomyopathy". Circulation, vol. 103, Feb. 2001, pp. 789-791. [Accessed at http://circ.ahaqjournals.org/ on Sep. 3, 2014].
Lin, et al., "Dapagliflozin Improves Cardiac Hemodynamics and Mitigates Arrhythmogenesis in Mitral Regurgitation-Induced Myocardial Dysfunction.", Journal of the American Heart Association 10.7 (2021): e019274, p. 1-18.
Lipworth, Brian J. "Clinical pharmacology of β3-adrenoceptors" Br J Clin Pharmacol (1996), 42: pp. 291-300.
List, et al., "Glucose Dynamics And Mechanistic Implications Of SGLT2 Inhibitors In Animals And Humans" (2011) Kidney International, vol. 79, Suppl 120, S20-S27.
Little, et al., "Heart failure is common in diabetic cats: findings from a retrospective case-controlled study in first-opinion practice." Journal of Small Animal Practice 49.1 (2008): 17-25.
Liu Yuqing,"Cardiovascular Imaging Diagnostics", 2000, p. 24.
Li-Yuan Bao et al.: "Progress and developments in the turbo Grignard reagent i—PrMgCl—LiCl"; Chemical Communications, vol. 51, No. 32, 2015, p. 6884-6900.
Lukens et al., "Pituitary-Diabetes In The Cat: Recovery Following Phlorhizin Treatment" Endocrinology, 1943, pp. 475-487, vol. 32.
Lukens et al., "Steroid Diabetes in the Cat—Protection of the Islets by Insulin or Phlorhizin" Diabetes, 1961, pp. 182-189, vol. 19, No. 3.
MacFarlane, D."Equine Pituitary Pars Intermedia Dysfunction" Vet Clin Equine, vol. 27 pp. 93-113 doi: 10.1016/j.cveq.2010.12.007 (Year:2011).
Supplemental experimental data, Dec. 1, 2024.
Suzuki, Hiromichi. "Investigation of Clinical Benefits of Different Types of ARBs in Treatment of Hypertension Associated with Renal Disease." Progress in Medicine 26.7 (2006): 145-151.
Syme et al., "Survival of Cats with Naturally Occurring Chronic Renal Failure Is Related to Severity of Proteinuria". Journal of Veterinary Internal Medicine, vol. 20, No. 3, 2006, pp. 528-535.
Tahara, et al. "Effects Of SGL T2 Selective Inhibitor Ipragliflozin On Hyperglycemia, Hyperlipidemia, Hepatic Steatosis, Oxidative Stress, Inflammation, And Obesity In Type 2 Diabetic Mice." European Journal of Pharmacology vol. 715 pp. 246-255, (2013), http://dx.doi.org/10.1016/j.ejphar.2013.05.014.
Tahara, et al., "Effects Of The SGL T2 Inhibitor Ipragliflozin On Various Diabetic Symptoms And Progression Of Overt Nephropathy In Type 2 Diabetic Mice." Naunyn-Schmiedeberg's Archives of Pharmacology 391.4 (2018): 395-406.
Tanaka, Chikako "Therapeutic Drugs for Metabolic Diseases, Chapter 2" (2002) New Yakurigaku (New Pharmacology) pp. 524-527.
Terami et al., "Long-Term Treatment with the Sodium glucose Cotransporter 2 Inhibitor", Dapagliflozin, Ameliorates Glucose Homeostasis and Diabetic Nephropathy in db/ db Mice, PLOSone, Jun. 2014, 9(6), e100777, pp. 1-13.
The Merck Index, Thirteen Edition, 2001; Reference 7412. Phloridzin, p. 1313.
Threlfall, Terry "Structural and Thermodynamic Explanations of Ostwald's Rule" Organic Process Research & Development (2003) vol. 7, pp. 1017-1027.
Tinworth, et al., "The Effect Of Oral Metformin On Insulin Sensitivity In Insulin-Resistant Ponies", The Veterinary Journal, 2012, vol. 191, pp. 79-84.
Tirmenstein et al., "Nonclinical Toxicology Assessments Support the Chronic Safety of Dapagliflozin, a First-in-Class Sodium-Glucose Cotransporter 2 Inhibitor". International Journal of Toxicology, vol. 32, No. 5, 2013, pp. 336-350.
Tran et al., "Modulation of microenvironmental pH and crystallinity of ionizable telmisartan using alkalizers in solid dispersions for controlled release", Elsevier, Journal of Controlled Release, 129 (2008), 59-65.

(56) References Cited

OTHER PUBLICATIONS

Treiber et al. 2006, The Journal of Nutrition, "Insulin Resistance in Equids: Possible Role in Laminitis", vol. 136 (7 Suppl): 2094S-2098S.
Treiber et al., "Laminitis in Ponies is a Diabetic-like State" Experimental Biology, The FASEB Journal, Meeting Abstracts, vol. 21, No. 6, Abstract No. 737.23, Apr. 2007, p. A833. [Accessed at https://www.fasebj.org/doi/10.1096/fasebj.21.6.A833 on Apr. 17, 2018].
Tykwinski, Rik R; Evolution in the Palladium-Catalyzed Cross-Coupling of sp- and sp2-Hybridized Carbon Atoms; Angew Chemical International Edition (2003) vol. 42 pp. 1566-1568.
U.S. Appl. No. 13/287,216, filed Nov. 2, 2011. Inventor: Rolf Grempler.
U.S. Appl. No. 13/367,739, filed Feb. 7, 2012. Inventor: Thomas Klein.
U.S. Appl. No. 13/413,702, filed Mar. 7, 2012. Inventor: Masanori Ito.
U.S. Appl. No. 13/637,413, filed Sep. 26, 2012. Inventor: Rolf Grempler.
U.S. Appl. No. 13/693,239, filed Dec. 4, 2012. Inventor: Klaus Dugi.
U.S. Appl. No. 13/785,365, filed Mar. 5, 2013. Inventor: Masanori Ito.
U.S. Appl. No. 13/833,097, filed Mar. 15, 2013. Inventor: Eric Williams Mayoux.
U.S. Appl. No. 12/545,175, filed Aug. 21, 2009, Inventor: Matthias Eckhardt.
Ueta et al., "Reduction of Renal Transport Maximum for Glucose by Inhibition of Na+-Glucose Cotransporter Suppresses Blood Glucose Elevation in Dogs." Biological and Pharmaceutical Bulletin, vol. 29, No. 1, 2006, pp. 114-118.
Ueta, et al., "Long-Term Treatment With The Na+ -Glucose Cotransporter Inhibitor T-1095 Causes Sustained Improvement In Hyperglycemia And Prevents Diabetic Neuropathy In Goto-Kakizaki Rats"; Life Sciences (2005) vol. 76 pp. 2655-2668.
Unsinn, et al., "A Convenient Alumination of Functionalized Aromatics by using the Frustrated Lewis Pair Et3Al and TMPMgCl·LiCl", Chemistry, vol. 19, No. 43, Oct. 18, 2013, p. 14687-14696.
US Label Bexagliflozin, Sep. 2022.
US Label Velagliflozin, Jun. 14, 2023.
Van Miert, "The use in animals of drugs licensed for human use only", Comparative Veterinary Pharmacology Toxicology and Therapy, Ch. 46, edited ASJPAM Van Miert, 2013, pp. 489-500.
Van Raalte et al., "Improving Glycaemic Control In Type 2 Diabetes" Stimulate Insulation Secretion Provide Beta-Cell Rest?, Diabetes Obes Metab. 2017; 19: pp. 1205-1213.
Venugopal et al., "Insulin Resistance In Equine Digital Vessel Rings: An In Vitro Model To Study Vascular Dysfunction In Equine Laminitis", 2011, Equine Veterinary Journal, vol. 43, No. 6, pp. 744-749.
Verbrugghe, Adronie, "Nutritional modulation of carbohydrate metabolism in domestic cats (*Felis catus*)" Ghent University, 2009, p. 53.
Villar et al., "Ibuprofen, Aspirin and Acetaminophen Toxicosis and Treatment in Dogs and Cats". Veterinary Human Toxicology, vol. 40, No. 3, 1998, pp. 156-162.
Wallace, et al., "Cyclopropylboronic Acid: Synthesis and Suzuki Cross-Coupling Reactions"; Tetrahedron Letters (2002) vol. 43 pp. 6987-6990; Pergamon Press.
Wancewicz, et al. "Short (12-Nucleotide) 2nd Generation Antisense Oligonucleotides Selectively Inhibit SGLT2 mRNA Expression Across Multiple Species and Are Bioavailable Following Intrajejunal Administration." Diabetes 56 (2007), Academic Journal, vol. 56, p. A144.
Washburn, William N., "Evolution of sodium glucose co-transporter 2 inhibitors as anti-diabetic agents." Expert Opinion on Therapeutic Patients, vol. 19, No. 11, 2009, pp. 1485-1499.
Web site: www.merck.com "Chronic Kidney Disease," accessed on Apr. 8, 2010, 7 pages.
Web site: www.merck.com "Tubulointerstitial Nephritis," accessed on Jun. 1, 2009, 9 pages.
Websters Third New International Dictionary, Editor: Gove, definition of prevent; 1963, 2 pgs.
Wheeler, et al., "SGLT2 Inhibitors: Slowing Of Chronic Kidney Disease Progression In Type 2 Diabetes." Diabetes Therapy 11 (2020): 2757-2774.
White, et al., "Effects of the angiotensin II receptor blockers telmisartan versus valsartan on the circadian variation of blood pressure: impact on the early morning period," Amer Journal of Hypertension, vol. 17, Issue 4, 2004, pp. 347-353.
Wienen et al., "A Review on Telmisartan: A Novel, Long-Acting Angiotensin II-Receptor Antagonist". Cardiovascular Drug Reviews, vol. 18, No. 2, 2000, pp. 127-154.
Wilansky et al., "The Effect Of Phenformin On Prediabetes", Metabolism, 1965, pp. 793-799, vol. 14, No. 7.
Wilkinson et al., Lipid based intramuscular long-acting injectables: Current state of the art, Jul. 3, 2022, pp. 1-20, vol. 178, No. 106253.
Wojtczak, A., "Prevention"' in Glossary of medical education terms: Parts 1-7. Ed. Medical Teacher. vol. 24, Nos. 2-6 and vol. 25, No. 1 &2. 2002.
Wolfe, et al., "Improved Functional Group Compatibility in the Palladium-Catalyzed Amination of Aryl Bromides"; Tetrahedron Letters, vol. 38, No. 36, Sep. 8, 1997, p. 6359-6362.
Written Opinion of the International Search Authority for PCT/EP2018/085193, Jun. 23, 2020.
Written Opinion of the International Search Authority PCT/EP2007/060531, mailed May 19, 2008.
Written Opinion of the International Search Authority PCT/EP2015/050940, mailed on Mar. 26, 2015.
Written Opinion of the International Search Authority PCT/EP2015/110402, mailed on Mar. 26, 2015.
Gross J.J. et al., "Glucose transport and milk secretion during manipulated plasma insulin and glucose concentrations and during LPS induced mastitis in dairy cows", Journal of Animal Physiology and Animal Nutrition, vol. 99, No. 4, Aug. 1, 2015, pp. 747-756.
Guangxi Agricultural College et al., "Oxidation in acidic solutions". Organic Chemistry, Guangxi People's Publishing House, Dec. 1982, p. 235.
Guidance for Industry, "Estimating the maximum safe starting dose in initial clinical trials for therapeutics in adult healthy volunteers", FDA, Jul. 2005, Pharmacology and Toxicology, 30 pages.
Hamilton, Kirk L. "Robert K. Crane—Na+-glucose cotransporter to cure?. " Frontiers in Physiology 4 (2013): 45054, pp. 1-5.
Han et al., "Dapagliflozin, a Selective SGLT2 Inhibitor, Improves Glucose Homeostasis in Normal and Diabetic Rats", Diabetes, vol. 57; Jun. 2008; p. 1723-1729 Han et al.; Diabetes, vol. 57; Jun. 2008; p. 1723-1729.
Han,Donghyun, "Long term effects after telmisartan administration for cardiovascular-renal axis disorder in cats", Journal of Biomedical Translational Research, 2019, 20(4):99-104.
Handlon, Anthony L. "Sodium glucose co-transporter 2 (SGLT2) inhibitors as potential antidiabetic agents" (2005) Expert Opinion on Therapeutic Patents, 15:11, 1531-1540.
Harley, et al., "Proteinuria in dogs and cats." The Canadian veterinary journal 53.6 (2012): 613-638.
Hatsuda, et al., A Practical Synthesis of Highly Functionalized Aryl Nitriles Through Cyanation of Aryl Bromides Employing Heterogeneous Pd/C; Tetrahedron Letters (2005) vol. 46 pp. 1849-1853; Elsevier Ltd.
Helvacı, et al., "A Story of Serendipities: From Phlorizin to Gliflozins. " Experimental and Clinical Transplantation: Official Journal of the Middle East Society for Organ Transplantation 21. Suppl 2 (2023): 105-108.
Henson et al., "Feline Models of Type 2 Diabetes Mellitus", ILAR Journal, vol. 37, No. 3, 2006, pp. 234-242.
Hirayama et al., Common mechanisms of inhibition for the Na+/glucose (hSGLT1) and Na+/C1-GABA (HGAT1) contransporters). British Journal of Pharmacology, vol. 134, Oct. 2001, pp. 484-495.
Hiwada, Kunio, "Presentation of New Drug: Telmisartan". Vascular Biology & Medicine, vol. 3, No. 5, 2002, pp. 571-576.
Hoenig, et al. "Effects of the sodium-glucose cotransporter 2 (SGLT 2) inhibitor velagliflozin, a new drug with therapeutic potential to

(56) References Cited

OTHER PUBLICATIONS treat diabetes in cats." Journal of Veterinary Pharmacology and Therapeutics 41.2 (2018): 266-273.
Honjo, et al. "Possible beneficial effect of telmisartan on glycemic control in diabetic subjects." Diabetes Care 28.2 (2005): 498-498.
Huang Yongqi, "Pharmacology and Pharmacology Experimental Tutorials", China Press of Traditional Chinese Medicine, published in Aug. 2014, p. 2.
Huskey et al., "N-glucuronidation reactions. I. Tetrazole N-glucuronidation of selected angiotensin II receptor antagonists in hepatic microsomes from rats, dogs, monkeys, and humans." Abstract, Drug Metabolism and Disposition, vol. 21, No. 5, 1993, pp. 792-299 (p. A-9).
Hussey, et al. "Safety, Pharmacokinetics and Pharmacodynamics of Remogliflozin Etabonate (SGLT2 Inhibitor) and Metformin When Co-Administered in Type 2 Diabetes Mellitus (T2DM) Patients" Diabetes, American Diabetes Association, (2009) XP00913667, vol. 58, p. A157.
Hutton, et al., A Convenient Preparation of dityrosine Via Miyaura Borylation-Suzuki Coupling of Iodotyrosine Derivatives; Tetrahedron Letters (2003) vol. 44 pp. 4895-4898; Pergamon Press.
Hynes, et al., "Further studies on the synthesis of quinazolines . . . "; Journal of Heterocyclic chemistry, vol. 28, No. 5, Aug. 1991, p. 1357-1363.
Idris, et al., "Sodium-Glucose Co-transporter-2 Inhibitors: An Emerging New Class of Oral Antidiabetic Drug." Diabetes, Obesity and Metabolism, vol. 11, No. 2, 2009, pp. 79-88.
Iida, et al., Tributylmagnesium Ate Complex-Mediated Novel Bromine-Magnesium Exchange Reaction for Selective Monosubstitution of Dibromoarenes; Tetrahedron Letters (2001) vol. 42 pp. 4841-4844; Pergamon Press.
Iino et al., "Renoprotective Effect of Losartan in Comparison to Amlodipine in Patients with Chronic Kidney Disease and Hypertension- a Report of the Japanese Losartan Therapy Intended for the Global Reneal Protection in Hypertensive Patients (JLIGHT) Study"_ Hypertension Research, vol. 27, No. 1, 2004, pp. 21-30.
International Search Report and Written Opinion for PCT/EP2014/056497 mailed Sep. 1, 2014.
International Search Report and Written Opinion for PCT/EP2014/077677 mailed Jun. 9, 2015.
International Search Report and Written Opinion for PCT/EP2015/050940 mailed Mar. 26, 2015.
International Search Report and Written Opinion for PCT/EP2015/056840 mailed Nov. 9, 2015.
International Search Report and Written Opinion for PCT/EP2016/069977 mailed on Oct. 7, 2016.
International Search Report and Written Opinion for PCT/EP2021/053585 mailed Sep. 1, 2014.
International Search Report and Written Opinion for PCT/EP2022/070898 mailed Nov. 15, 2022.
International Search Report and Written Opinion for PCT/EP2022/070940 mailed Oct. 13, 2022.
International Search Report and Written Opinion for PCT/EP2022/070943 mailed Oct. 26, 2022.
International Search Report and Written Opinion for PCT/EP2024/055543 mailed on Jun. 10, 2024.
International Search Report and Written Opinion for PCT/EP2024/060490 mailed on Jul. 26, 2024.
International Search Report and Written Opinion for PCT/EP2024/063672 mailed on Jul. 26, 2024.
International Search Report and Written Opinion for PCT/EP2024/063674 mailed on Nov. 4, 2024.
International Search Report and Written Opinion of PCT/EP2013/065736 mailed Sep. 3, 2013.
International Search Report and Written Opinion of PCT/EP2015/071637 mailed on Feb. 29, 2016.
International Search Report for PCT/EP2005/002618 mailed Jun. 30, 2005.
International Search Report for PCT/EP2005/056806 mailed Dec. 27, 2006.
International Search Report for PCT/EP2006/061520 mailed Jul. 26, 2006.
International Search Report for PCT/EP2006/061956 mailed on Jul. 5, 2006.
International Search report for PCT/EP2006/061957 mailed on Jul. 5, 2006.
International Search Report for PCT/EP2006/062191 mailed Aug. 8, 2006.
International Search Report for PCT/EP2006/064702 mailed on Jul. 26, 2007.
International Search Report for PCT/EP2006/065710 mailed Mar. 8, 2007.
International Search Report for PCT/EP2006/066107 mailed Jan. 11, 2007.
International Search Report for PCT/EP2006/066347 mailed Mar. 7, 2007.
International Search Report for PCT/EP2007/051411 mailed on May 2, 2007.
International Search Report for PCT/EP2007/054248 mailed on Jun. 18, 2007.
Written Opinion of the International Search Authority PCT/EP2022/070943, mailed on Oct. 26, 2022.
Written Opinion of the International Search Authority WO2023006747, mailed on Oct. 26, 2022.
Written Opinion of the International Searching Authority for PCT/EP2007054248 mailed on Jun. 18, 2007.
Written Opinion of the International Searching Authority for PCT/EP2010/056895 mailed on Aug. 3, 2010.
Written Opinion of the International Searching Authority for PCT/EP2020083267 mailed on Feb. 22, 2021.
Xiao et al., "Regional Hemodynamic Effects of the AT1 Receptor Antagonist CV-11974 in Conscious Renal Hypertensive Rats". Hypertension, vol. 26, 1995, pp. 989-997.
Xu et al., "Design, Synthesis, and Biological Evaluation of Deuterated C-Aryl Glycoside as a Potent and Long-Acting Renal Sodium-Dependent Glucose Cotransporter 2 Inhibitor for the Treatment of Type 2 Diabetes". Journal of Medicinal Chemistry, vol. 57, 2014, pp. 1236-1251.
Xue, et al., Zinc-mediated Synthesis of Alpha-C-Glycosides from 1,2-Anhydroglycosides; Synletters (2003) vol. 6 pp. 870-872.
Xue, Jintong, " Hypertensive Disease". Chapter 13. Practical Handbook for the Diagnosis and Treatment of cardiovascular Disease, First Edition, Zhengzhou University Press, 2005, pp. 480-508.
Xueyun, Physiological Experiment Guidance, Shanghai Science and Technology Press. Published in Jun. 1995, p. 55.
Xueyun, Physiological Experiment Guidance, Shanghai Science and Technology Press. Published in Jun. 1995, p. 55 (EN translation).
Yamada, et al., "Clinic: Careful Progress in the Field and new Therapeutic Methods" Medical Online, (2007) vol. 220, No. 13, pp. 1219-1221.
Yamamoto et al., "TS-071 is a novel, potent and selective renal sodium-glucose cotransporter 2 (SGLT2) inhibitor with anti-hyperglycaemic activity." British Journal of Pharmacology, vol. 164, No. 1, 2011, pp. 181-191.
Yang et al. "Concise Handbook of Poultry Disease Prevention and Control", 2002, the first edition, Jan. 2003, the second print Jan. 2003, pp. 301-330.
Yasuko, Bando, "Pathogenesis and molecular mechanisms of heart failure in diabetes What is diabetic cardiomyopathy? one." 14 Cardiac vol. 52 No. 1 (2020).
Yoshida et al.,"Metabolic effect of All receptor" Ketsuatsu (Blood Pressure), vol. 9, No. 8, 2002, pp. 802-806.
Yoshida et al.,"Metabolic effect of All receptor" Ketsuatsu (Blood Pressure), vol. 9, No. 8, 2002, pp. 802-806_English Abstract.
Zafeiriou et al., "Brain and Spinal MR Imaging Findings in Mucopolysaccharidoses:A review." American Journal of Neuroradiology, vol. 34, Jan. 2013, pp. 5-13.
Zeng, et al. "Antifibrotic effects of low dose SGL T2 Inhibition with empagliflozin in comparison to Ang II receptor blockade with telmisartan in 5/6 nephrectomised rats on high salt diet." Biomedicine & Pharmacotherapy 146 (2022): 112606, pp. 1-9.

(56) References Cited

OTHER PUBLICATIONS

Zhang Ningzi et al., "Handbook of Practical Cardiovascular Medicine", p. 680, 1997.
Zhang Yan et al., "China Traditional Chinese Medicine Press", 2005, p. 3.
Zhang, et al."Dapagliflozin Treatment In Patients With Different Stages Of Type 2 Diabetes Mellitus: Effects On Glycaemic Control And Body Weight" Diabetes, Obesity and Metabolism (2010) vol. 12, No. 6, p. 510-516.
Zhang, et al., "EGT1442, a potent and selective SGLT2 inhibitor, attenuates blood glucose and HbA1c levels in db/db mice and prolongs the survival of stroke-prone rats." Pharmacological Research 63.4 (2011): 284-293.
Zhang, Hong-Yu. "Research progress on synthesis of phloretin derivatives." Chinese Traditional and Herbal Drugs (2017): 4353-4360.
Zhao F. Q., "Biology of Glucose Transport in the Mammary Gland", J Mammary Gland Biol Neoplasia, vol. 19, 2014, pp. 3-17.
Zhao F. Q., et al., "Cloning and Expression of Bovine Sodium/Glucose Cotransporter SGLT", Journal of Dairy Science, vol. 88, No. 1, Aug. 1, 2005, pp. 2738-2748.
Zhao, et al., "Research progress of glucose regulates the lactose bio-synthesis of the lactation progress in the mammary gland" China Dairy Cattle, vol. 8,2009, pp. 26-30.
Niessen, Stijn JM, et al. "Efficacy and safety of once daily oral administration of sodiumglucose cotransporter2 inhibitor velagliflozin compared with twice daily insulin injection in diabetic cats." Journal of Veterinary Internal Medicine 38.4 (2024): 2099-2119.
Reiche D.B., et al., Co-Pending U.S. Appl. No. 18/086,830, filed Dec. 22, 2022, 96 Pages.
Reusch C.E., et al., Swiss Archives of Veterinary Medicine, 2011, vol. 153811, pp. 495-500.
Rudnic E., et al. "Oral Solid Dosage Forms," Remington's Pharmaceutical Sciences, 18th Edition, Gennaro, A.R. Ed, Macie Pub. Co., Chapter 89, 1990, pp. 1633-1665.
Schlienger J-L., et al., "From Apple Root Bark to Sodium-Glucose Transporter Type 2 (SGLT2) Inhibitors: The Crazy Story of Phloridzin," Medicine for Metabolic Diseases, Dec. 5, 2023, vol. 18, No. 3, pp. 280-286, (English Translation).
Sloan J.L., et al., "Disorders of Intracellular Cobalamin Metabolism," Gene Reviews, 2008, 42 Pages, (Initial Posting: Feb. 25, 2008).
Supplement to: Anker S.D., et al., "Empagliflozin In Heart Failure With A Preserved Ejection Fraction," New England Journal of Medicine, Supplementary Appendix, 2021, vol. 385, No. 16, pp. 1451-1461 (38 Pages), DOI: 10.1056/NEJMoa2107038.
Tanaka, et al., Veterinary Research Communications, 2005, vol. 29, No. 6, pp. 477-485.
Tashiro K., "Null-Steering Technique in HAPS Systems for Spectrum Sharing with Terrestrial Mobile Networks," IEICE Technical Report, IEICE, JP, JP, Jun. 16, 2021, vol. 121, No. 72 (RCS2021-75), pp. 267-272, DOI: 10.1152/ajplegacy.1962.203.6.975, XP009556586.
Tomonari K., et al., "Inhibitory Effects of Tofogliflozin on Cardiac Hypertrophy in Dahl Salt-Sensitive and Salt-Resistant Rats Fed a High-Fat Diet," International Heart Journal, JP, May 30, 2019, vol. 60, No. 3, pp. 728-735, DOI: 10.1536/ihj.18-392, ISSN: 1349-2365, XP093232879.
Toshiyuki T., et al., "Effect of Ipragliflozin, an SGLT2 Inhibitor, on Cardiac Histopathological Changes in a Non-diabetic Rat Model of Cardiomyopathy," Life Science, Aug. 10, 2019, vol. 230, pp. 19-27, DOI:10.1016/J.LFS.2019.05.051, XP085710549.
US Label"Velagliflozin Oral Solution," Snevelgo, Jun. 14, 2023, 1 Page.
Verbrugghe, et al., Critical Reviews in Food Science and Nutrition, 2012, vol. 52, No. 2, pp. 172-182.
Wang, Ying, et al. "Additive effect of aldose reductase Z-4 microsatellite polymorphism and glycaemic control on cataract development in type 2 diabetes." Journal of Diabetes and its Complications 28.2 (2013).
Warner, Timothy D., et al. "Nonsteroid drug selectivities for cyclo-oxygenase-1 rather than cyclo-oxygenase-2 are associated with human gastrointestinal toxicity: a full in vitro analysis." Proceedings of the National Academy of Sciences 96.13 (1999): 7563-7568.
Wright, Ernest M., Donald DF Loo, and Bruce A. Hirayama. "Biology of human sodium glucose transporters." Physiological reviews 91.2 (2011): 733-794.
Wright, Ernest M. "SGLT2 inhibitors: physiology and pharmacology." Kidney360 2.12 (2021): 2027-2037.
Written Opinion of the International Application No. PCT/EP2015/110402, dated Mar. 26, 2015.
Xueyun, "Chapter VI Calculation Method of Drug Dosage for Laboratory Animals," Physiological Experiment Guidance, Shanghai Science and Technology Press, Jun. 1995, p. 55 (2 Pages), (English Translation).
Yoshida H., et al., "Metabolic Effect of All Receptor Antagonists," Ketsuatsu (Blood Pressure), 2002, vol. 9, No. 8, pp. 802-806 (7 Pages), Japanese Translation.
Yurista S.R., et al., "Sodium-glucose Co-transporter 2 Inhibition With Empagliflozin Improves Cardiac Function in Non-diabetic Rats With Left Ventricular Dysfunction After Myocardial Infarction," European Journal of Heart Failure, NL, Apr. 29, 2019, vol. 21, No. 7, pp. 862-873, DOI: 10.1002/ejhf.1473, ISSN: 1388-9842, XP093232906, Retrieved from URL: https://onlinelibrary.wiley.com/doi/full-XML/10.1002/ejhf.1473.
Zhang N., et al., "Dapagliflozin Improves Left Ventricular Remodeling and Aorta Sympathetic Tone in a Pig Model of Heart Failure With Preserved Ejection Fraction," Cardiovascular Diabetology, GB, Dec. 1, 2019, vol. 18, No. 1, DOI: 10.1186/s12933-019-0914-1, ISSN 1475-2840, XP093166000, [Retrieved On Sep. 30, 2025] Retrieved From URL: https://epo.summon.serialssolutions.com/2.0.0/link/0/eLvHCXMwrR3JbtNAdFTSA1xYxGYoaDghgdJ4Gc_YUoUUSIsOCCEoh55G41mCqetETiJUfoWf5b2xY8UFgZC4RZ43.
Zini, Eric, et al. "Hyperglycemia but not hyperlipidaemia causes beta cell dysfunction and beta cell loss in the domestic cat." Diabetologia 52.2 (2009): 336-346.
Extended European Search Report for European Application No. 23175197.5, dated Nov. 17, 2023, 8 Pages.
Extended European Search Report for European Application No. 23185606.3, dated Feb. 21, 2024, 18 Pages.
Extended European Search Report for European Application No. 23204783.7, dated Jan. 29, 2024, 13 Pages.
Extended European Search Report for European Application No. 24174463.0, dated Dec. 11, 2024, 18 Pages.
Extended European Search Report for European Application No. 24193611.1, dated Jan. 2, 2025, 15 Pages.
Extended European Search Report for European Application No. 24204085.5, dated Feb. 4, 2025, 11 Pages.
Extended European Search Report for European Application No. EP18155079.9, dated Jun. 25, 2018, 10 Pages.
Extended European Search Report for European Application No. EP22202153.7, dated Mar. 17, 2023, 8 Pages.
Feldman, Edward C., Richard W. Nelson, and Marsha S. Feldman. "Intensive 50-week evaluation of glipizide administration in 50 cats with previously untreated diabetes mellitus." Journal of the American Veterinary Medical Association 210.6 (1997): 772-777.
Ferasin L., et al., "Management of Acute Heart Failure in Cats," Journal of Veterinary Cardiology, 2015, vol. 17, pp. S173-S189.
Frank N., et al., "Diagnosis And Treatment Of Pituitary Pars Intermedia Dysfunction (PPID)," The PPID Working Group, Sep. 2011.
Frank N., et al., "Equine Metabolic Syndrome," ACVIM Consensus Statement, Journal of Veterinary Internal Medicine, 2010, vol. 24, No. 3, pp. 467-475.
Frank N., et al., "Equine Metabolic Syndrome," Journal of Equine Veterinary Science, 2009, vol. 29, No. 5, pp. 259-267 (9 Pages).
Frank N., et al., "Insulin Dysregulation," Equine Veterinary Journal, 2014, vol. 46, pp. 103-112(10 Pages), DOI: 10.1111/evj.12169, First Published on 2013.
Freeman L.M., et al., "Feline Hypertrophic Cardiomyopathy: A Spontaneous Large Animal Model of Human HCM," Cardiology Research, 2017, vol. 8, No. 4, pp. 139-142(4 Pages).

(56) References Cited

OTHER PUBLICATIONS

French K., et al., "Pharmacokinetics and Metabolic Effects of Triamcinolone Acetonide and Their Possible Relationships to Glucocorticoid-induced Laminitis in Horses," Journal Of Veterinary Pharmacology And Therapeutics, 2000, vol. 23, pp. 287-292 (6 Pages).
Fuerstner A., et al., "Practical Method for the Rhodium-Catalyzed Addition of Aryl- and Alkenylboronic Acids to Aldehydes," Advanced Synthesis and Catalysis, 2001, vol. 343, No. 4, pp. 343-350.
Fujimori Y., et al., "Remogliflozin Etabonate, in a Novel Category of Selective Low-affinity Sodium Glucose Cotransporter (SGLT2) Inhibitors, Exhibits Antidiabetic Efficacy in Rodent Models," The Journal of Pharmacology and Experimental Therapeutics, 2008, vol. 327, No. 1, pp. 268-276.
Gallo L.A., "Probing SGLT2 as a Therapeutic Target for Diabetes: Basic Physiology and Consequences," Diabetes and Vascular Disease Research, Medinews, Birmingham, GB, Mar. 2015, vol. 12, No. 2, pp. 78-89, (20 Pages), DOI: 10.1177/1479164114561992, ISSN 1479-1641, XP093197873.
Garrison E.A., et al., "[Pro11, D-Ala12 ] Angiotensin I Has Rapid Onset Vasoconstrictor Activity in the Cat," American Journal of Physiology, Endocrinology and Metabolism, 1997, vol. 273, pp. E1059-E1064 (7 Pages).
Gehlen H., et al., "Comparison of Insulin and Glucose Metabolism in Horses with Pituitary Pars Intermedia Dysfunction Treated Versus Not Treated with Pergolide," Journal of Equine Veterinary Science, 2014, vol. 34, No. 4, pp. 508-513, Published Online on Nov. 9, 2013.
Gekkan Shinzo, Monthly Heart, Jan. 15, 2020, vol. 52 No. 1, p. 14-18, ISSN: 0005111931.
Ghassemi H., et al., "Synthesis and Properties of New Sulfonated Poly(p-phenylene) Derivatives for Proton Exchange Membranes," Polymer, 2004, pp. 5847-5854.
Gostelow, Ruth, et al. "Systematic review of feline diabetic remission: separating fact from opinion." The Veterinary Journal 202.2 (2014): 208-221.
Grauer G., "ACE Inhibitors and CKD," Hypertension, 2 Pages, [Retrieved on Feb. 5, 2015] Retrieved From URL: http://www.dvm360storage.com/cvc/proceedings/dc/Urology/Grauer/Grauer,Gregory_ACE_Inhibitors_and_CKD.pdf.
Greco D.S., "Treatment of Feline Type 2 Diabetes Mellitus With Oral Hypoglycemic Agents," OVMA Conference Proceedings, 2005, pp. 49-52.
Greco G.T., et al., "Segregation of Active Constituents from Tablet Formulations During Grinding: Theoretical Considerations," Drug Development and Industrial Pharmacy, 1982, vol. 8, No. 4, pp. 565-578.
Grempler R., et al., "Empagliflozin, A Novel Selective Sodium Glucose Cotransporter-2 (SGLT-2) Inhibitor: Characterisation and Comparison with Other SGLT-2 Inhibitors," Diabetes Obesity and Metabolism, Jan. 1, 2012, vol. 14, No. 01, pp. 83-90, (First published: Oct. 10, 2011), XP055228524, Retrieved from URL: http://dx.doi.org/10.1111/j.1463-1326.2011.01517.x.
Hoenig, et al., American Journal of Physiology, 2011, vol. 301, No. 6, pp. R1798-1807.
Hoenig, Margarethe. "Carbohydrate metabolism and pathogenesis of diabetes mellitus in dogs and cats." Progress in molecular biology and translational science 121 (2014): 377-412.
Hoenig, Margarethe, et al. "A feline model of experimentally induced islet amyloidosis." The American journal of pathology 157.6 (2000): 2143-2150.
Hoenig, Margarethe. "The cat as a model for human obesity and diabetes." Journal of diabetes science and technology 6.3 (2012): 525-533.
Hoenig, Molecular and Cellular Endocrinology, 2002, vol. 197, No. 1-2, pp. 221-229.
Hummel, Charles S., et al. "Structural selectivity of human SGLT inhibitors." American Journal of Physiology—Cell Physiology 302.2 (2012): C373-C382.
International Preliminary Report on Patentability for International Application No. PCT/EP2018/085193, dated Jul. 2, 2020, 10 Pages.
International Search Report and Written Opinion for International Application No. PCT/EP2023/063549, dated on Jul. 10, 2023, 20 Pages.
International Search Report for International Application No. PCT/EP2007/060531, dated May 19, 2008, 8 Pages.
International Search Report for International Application No. PCT/EP2020/083267, dated Feb. 22, 2021, 4 Pages.
Klein T., et al., U.S. Appl. No. 13/367,739, filed Feb. 7, 2012, 53 Pages.
Komoroski, B., et al. "Dapagliflozin, a novel, selective SGLT2 inhibitor, improved glycemic control over 2 weeks in patients with type 2 diabetes mellitus." Clinical Pharmacology & Therapeutics 85.5 (2009): 513-519.
Lapuerta, Pablo, et al. "Development of sotagliflozin, a dual sodium-dependent glucose transporter 1/2 inhibitor." Diabetes and Vascular Disease Research 12.2 (2015): 101-110.
Lehmann U., et al., "Palladium-Catalyzed Cross-Coupling Reactions Between Dihydropyranylindium Reagents and Aryl Halides: Synthesis of C-Aryl Glycals," Organic Letters, 2003, vol. 5, No. 14, pp. 2405-2408.
Malkina A., "Chronic Kidney Disease," Merck Manual, 2022, 11 Pages, [Retrieved on Apr. 8, 2010] Retrieved from URL : www.merck.com.
Mark J Acierno; Scott Brown; Amanda E Coleman; Rosanne E Jepson; Mark Papich; Rebecca L Stepien; Harriet M Syme, ACVIM consensus statement: Guidelines for the identification, evaluation, and management of systemic hypertension in dogs and cats, Journal of Veterinary Internal Medicine, Nov. 1, 2018 Wiley-Blackwell Publishing, Inc, US-ISSN 0891-6640, vol. 32, Nr:6, pp. 1803-1822, http://dx.doi.org/10.1111/jvim.15331, XP055717957.
Mayoux E.W., U.S. Appl. No. 13/833,097, filed Mar. 15, 2013, 43 Pages.
Michael J., et al., "The Sodium-Glucose Cotransporter 2 Inhibitor Dapagliflozin Prevents Cardiomyopathy in a Diabetic Lipodystrophic Mouse Model," Diabetes, Apr. 1, 2017, vol. 66, No. 4, pp. 1030-1040, DOI: 10.2337/db16-0733, ISSN: 0012-1797, XP093232710, Retrieved from URL: https://diabetesjournals.org/diabetes/article-pdf/66/4/1030/537116/db160733.pdf.
NADA: "Freedom of Information Vetsulin," pp. 141-236 (Mar. 24, 2008).
Nelson, R. W., et al. "Effect of an orally administered sulfonylurea, glipizide, for treatment of diabetes mellitus in cats." Journal of the American Veterinary Medical Association 203.6 (1993): 821-827.
Nelson, Richard W., and Claudia E. Reusch. "Animal models of disease: classification and etiology of diabetes in dogs and cats." Journal of endocrinology 222.3 (2014): T1-T9.
Nelson, Richard W., et al. "Transient clinical diabetes mellitus in cats: 10 cases (19891991)." Journal of Veterinary Internal Medicine 13.1 (1999): 28-35.
Abstract—Lutz, Thomas A., and Jacqueline S. Rand. "Pathogenesis of feline diabetes mellitus." Veterinary Clinics of North America: Small Animal Practice 25.3 (1995): 527-552.
Abstract of Dohan, F. C., and F. D. W. Lukens. "Experimental diabetes produced by the administration of glucose." Endocrinology 42.4 (1948): 244-262.
Bannwarth H., et al., "Basics of Physics, Chemistry, and Biochemistry," Excerpt from Chapter 14, 3rd Edition, 2013, pp. 323-325 (6 Pages).
Bannwarth H., et al., "Basics of Physics, Chemistry, and Biochemistry," Excerpt from Chapter 14, 3rd Edition, 2013, pp. 323-325 (6 Pages), English Abstract.
Beam, et al., Veterinary Ophthalmology, 1999, vol. 2, pp. 169-172.
Boehringer-Ingelheim: "Canine Diabetes Mellitus laboratory model," Experimental Report, Methods & Results, 1993, 2 Pages.
British Journal of Pharmacology vol. 164, Supplement 1, Nov. 2011, Guide to Receptors and Channels (GRAC), 5th Edition, on p. S231.
Catchpole, et al., Diabetologia, 2005, vol. 48, pp. 1948-1956.
Cefalu W.T., "Animal Models of Type 2 Diabetes: Clinical Presentation and Pathophysiological Relevance to the Human Condition," ILAR Journal, 2006, vol. 47, No. 3, 12 Pages.

(56) References Cited

OTHER PUBLICATIONS

Clark, M. H., et al. "Pharmacokinetics of pioglitazone in lean and obese cats 1." Journal of Veterinary Pharmacology and Therapeutics 35.5 (2012): 428-436.
Communication of a Notice of Opposition for European Application No. 21155065.2, dated Jul. 31, 2024, 67 Pages.
Conlon P.D., "Nonsteroidal Drugs Used in the Treatment of Inflammation," Clinical Pharmacology, Crossref Journals, Nov. 1988, vol. 18, No. 6, pp. 1115-1131 (17 Pages).
Coronel F., et al., "Hypertension Treatment in Nondiabetic Advanced Chronic Kidney Disease Patients with Irbesartan. Effect on Serum Uric Acid," Abstract, Journal of Hypertension, Jun. 17-21, 2005, vol. 23, Suppl. 2, p. S65 (3 Pages).
Court M.H., et al., "Molecular Basis for Deficient Acetaminophen Glucuronidation in Cats an Interspecies Comparison of Enzyme Kinetics in Liver Microsomes," Biochemical Pharmacology, Apr. 4, 1997, vol. 53, No. 7, pp. 1041-1047 (7 Pages).
Court M.H., et al., "Molecular Genetic Basis for Deficient Acetaminophen Glucuronidation by Cats: UGT1A6 is a Jseudogene, and Evidence for Reduced Diversity of Expressed Hepatic UGT1A Isoforms," Pharmacogenetics, 2000, vol. 10, pp. 355-369.
Court M.H., "Feline Drug Metabolism and Disposition: Pharmacokinetic Evidence for Species Differences and Molecular Mechanisms," Veterinary Clinics of North America: Small Animal Practice, Sep. 2013, vol. 43, No. 5, pp. 1-20 (20 Pages).
Curry, et al., Comparative Biochemistry and Physiology, 1982, vol. 72A, No. 2, pp. 333-338.
Custodio J.S. Jr., et al., "SGLT2 Inhibition and Heart Failure-Current Concepts," Heart Failure Reviews, 2018, vol. 23, pp. 409-418 (10 Pages).
De Champlain J., et al., "Do Angiotensin II Antagonists Provide Benefits beyond Blood Pressure Reduction?," Advances in Therapy, Mar./Apr. 2005, vol. 22, No. 2, pp. 117-136 (20 Pages).
De Laat M.A., et al., "Equine Laminitis: Induced by 48 H Hyperinsulinaemia in Standardbred Horses," Equine Veterinary Journal, 2010, vol. 42, No. 2, pp. 129-135 (7Pages).
Deacon C.F., "Perspectives in Diabetes Therapeutic Strategies Based on Glucagon-Like Peptide 1," Diabetes, Sep. 2004, vol. 53, pp. 2181-2189.
Decision of Invalidation Request for Chinese Patent Application No. 200580044703.3, Decision No. 42795, China National Intellectual Property Administration of People's Republic of China, dated Jan. 13, 2020, 16 Pages.
Declaration of Matthias Eckhardt Under 37 C.F.R. 1.132 for U.S. Appl. No. 15/113,127, dated Mar. 6, 2019, 05 Pages.
Declaration Under 37 C.F.R. 1.132 by Dania Birte Reiche for U.S. Appl. No. 15/113,127, dated Jul. 9, 2019, 07 Pages.
Declaration Under 37 C.F.R. 1.132 by Warnken T, for U.S. Appl. No. 17/094,591, dated Feb. 27, 2025, 11 Pages.
"Definition Of "Prevent","Oxford English Dictionary Online, Especially Definition 9a. at p. 2, 2010, 4 Pages, [Retrieved On May 27, 2010] Retrieved From URL: http://dictionary.oed.com/.
Dekkers C.C.J., "Sodium-glucose Cotransporter 2 Inhibitors: Extending the Indication to Non-diabetic Kidney Disease," Nephrology Dialysis Transplantation, 2020, vol. 35, Suppl. 1, pp. i33-i42.
Deshpande P.P., et al. "A Practical Stereoselective Synthesis and Novel Cocrystallizations of an Amphiphatic SGLT-2 Inhibitor," Organic Process Research & Development, 2012, vol. 16, No. 4, pp. 577-585.
Diabetes: "Clinical Therapeutics/new Technology-pharmacologic Treatment of Diabetes or Its Complications," Diabetes, Abstract Book 67th Scientific Sessions, Jun. 22-26, 2007, vol. 56, Supplement No. 1, pp. A114-A145 (5 Pages).
Dohan F.C., et al., "Lesions of the Pancreatic Islets Produced in Cats by Administration of Glucose," Science, Feb. 14, 1947, vol. 105, No. 2720, p. 183 (2 Pages), DOI: 10.1126/science.105.2720.183, XP093197861.
Dohle W., et al., "Copper-Mediated Cross-Coupling of Functionalized Arylmagnesium Reagents with Functionalized Alkyl and Benzylic Halides," Organic Letters, 2001, vol. 3, No. 18, pp. 2871-2873.
Drug Watch: "Type 2 Diabetes Mellitus," Formulary, Aug. 2008, vol. 43, p. 304.
Duez H., et al., "DPP-4 Inhibitors in the Treatment of Type 2 Diabetes," Biochemical Pharmacology, 2012, vol. 83, pp. 823-832 (10 Pages), DOI: 10.1016/j.bcp.2011.11.028, Epublished on Dec. 13, 2011.
Durham A.E., et al., "The Effect of Metformin on Measurements of Insulin Sensitivity and (Beta)-cell Response in 18 Horses and Ponies with Insulin Resistance," Equine Veterinary Journal, 2008, vol. 40, No. 5, pp. 493-500, DOI: 10.2746/042516408X273648.
Durham A.E., et al., "Type 2 Diabetes Mellitus With Pancreatic Beta Cell Dysfunction in 3 Horses Confirmed With Minimal Model Analysis," Equine Veterinary Journal, 2009, vol. 41, No. 9, pp. 924-929 (6 Pages).
Ebner T., et al., "Disposition and Chemical Stability of Telmisartan 1-O-Acylglucuronide," The American Society for Pharmacology and Experimental Therapeutics, Drug Metabolism and Disposition, 1999, vol. 27, No. 10, pp. 1143-1149 (7 Pages).
Ebner T., et al., "In Vitro Glucuronidation of the Angiotensin II Receptor Antagonist Telmisartan in the Cat: a Comparison with Other Species," Journal of Veterinary Pharmacology and Therapeutics, 2013, vol. 36, No. 2, pp. 154-160 (7 Pages).
Elischer M., "History of Dairy Cow Breeds: Holstein," The Holstein Dairy Cow, Michigan State University Extension, Apr. 4, 2016, 2 Pages, Retrieved from URL:.udel.edu/canr-animalscience/2016/04/07/the-holstein-dairy-cow/.
Elkinson S., et al., "Canagliflozin: First Global Approval," Drugs, Jun. 1, 2013, vol. 73, No. 9, pp. 979-988 (12 Pages).
Elkinson S., et al., "Canagliflozin: First Global Approval," Drugs, 2013, vol. 73, No. 9, pp. 979-988(10 Pages), Published Online (Jun. 1, 2013).
Emmerich I. U., "New Drugs For Small Animals in 2012", Veterinary practice, Edition K, Small Animals/Pets, Jan. 1, 2013, vol. 42, No. 4, pp. 237-243 (2 Pages) Abstract.
Emmerich I.U., "New Drugs for Small Animals in 2012," Veterinary Practice, Issue K, Small Animals/Home Animals, Jan. 1, 2013, vol. 42, No. 4, pp. 237-243, (Apr. 2013).
English_Abstract_for_WO2008089872A1_NPL.
Ettinger S.J., et al., "Therapeutic Considerations in Medicine and Disease," Textbook of Veterinary Internal Medicine Diseases of the Dog and Cat, Sixth Edition, vol. 1, Section VI, Table 143-1, 2005, pp. 530-531, (3 Pages).
European Application No. EP13197821, filed on Dec. 17, 2013, 71 Pages.
European Application No. EP14187228, filed on Oct. 1, 2014, 83 Pages.
Extended European Search Report for European Application No. 18208143, dated Apr. 12, 2019, 8 Pages.
Extended European Search Report for European Application No. 20172247.7, dated Aug. 7, 2020, 13 Pages.
Extended European Search Report for European Application No. 21155065.2, dated Jul. 9, 2021, 12 Pages.
Extended European Search Report for European Application No. 23171761.2, dated Aug. 23, 2023, 12 Pages.
Caira, Mino R. "Crystalline polymorphism of organic compounds." Design of Organic Solids. Berlin, Heidelberg: Springer Berlin Heidelberg, 1998. 163-208.
Adeghate et al. An update of SGLT1 and SGLT2 inhibitors in early phase diabetes-type 2 clinical trials. Expert Opinion On Investigational Drugs 2019, vol. 28, No. 9, 811-820. (Year: 2019).
The 'Glossary of Medical Education Terms', Institute for International Medical Education (IIME), Revised Feb. 2002. https:// www.iime.org/glossary.htm#P (accessed on Apr. 20, 2024) (Year: 2024).
Scheen, Effects of reducing blood pressure on cardiovascular outcomes and mortality in patients with type 2 diabetes: Focus on SGLT2 inhibitors and Empa-Reg Outcome, Diabetes Res. Clin. Pract., 2016, vol. 121 pp. 204-214 (Year: 2016).
Oh, Chang-Myung, et al. "Cardioprotective potential of an SGLT2 inhibitor against doxorubicin-induced heart failure." Korean circulation journal 49.12 (2019): 1183.

* cited by examiner

AQUEOUS PHARMACEUTICAL COMPOSITIONS COMPRISING SGLT-2 INHIBITORS

INCORPORATION BY REFERENCE

All references cited herein, are incorporated by reference herein, in their entirety.

FIELD OF THE INVENTION

The invention relates to the field of medicine, particularly veterinary medicine. In particular, the invention relates to novel aqueous pharmaceutical compositions comprising at least one SGLT-2 inhibitor and one or more solubilizing agents.

BACKGROUND OF THE INVENTION

The treatment of diabetes and other metabolic disorders includes the inhibition of the renal sodium-dependent glucose co-transporter SGLT-2. SGLT-2 in the kidney regulates glucose levels by mediating the reabsorption of glucose back into the plasma following filtration of the blood. SGLT-2 inhibition thus induces glucosuria and may reduce blood glucose levels. A large variety of SGLT-2 inhibitors are known. A pharmaceutical formulation of SGLT-2 inhibitors is essential in order to administer such compounds in an adequate way to the patient.

EP 1 609 785 discloses C-glycoside derivatives and salts thereof, wherein B ring is bonded to A ring via —X— and A ring is directly bonded to the glucose residue, and it is usable as a $Na^+$-glucose cotransporter inhibitor, especially for a therapeutic and/or preventive agent for diabetes such as insulin-dependent diabetes (type 1 diabetes) and insulin-independent diabetes (type 2 diabetes), as well as diabetes related diseases such as an insulin-resistant diseases and obesity.

WO 2006/064033 discloses glucopyranosyl-substituted benzene derivatives including the tautomers, the stereoisomers thereof, the mixtures thereof and the salts thereof, which are suitable for the treatment of metabolic disorders.

SGLT-2 inhibitors are for instance described in WO 2007/028814 which is directed to crystalline forms of 1-chloro-4-([beta]-D-glucopyranos-1-yl)-2-(4-ethynyl-benzyl)-benzene, a method for the preparation thereof, as well as the use thereof for preparing medicaments. It discloses solutions of 1-chloro-4-([beta]-D-glucopyranos-1-yl)-2-(4-ethynyl-benzyl)-benzene in a solvent or a mixture of solvents and further specifies exemplarily suitable organic solvents such as ethanol or ethanol/water mixtures.

WO 2007/080170 describes crystalline forms of 1'-(1-methylethyl)-4'-[(2-fluoro-4-methoxyphenyl) methyl]-5'-methyl-1H-pyrazol-3'-O-[beta]-D-glucopyranoside, a method for the preparation thereof, as well as the use thereof for preparing medicaments. It discloses solutions of 1'-(1-methylethyl)-4'-[(2-fluoro-4-methoxyphenyl) methyl]-5'-methyl-1H-pyrazol-3'-O-[beta]-D-glucopyranoside in a solvent or a mixture of solvents and further specifies exemplarily suitable organic solvents such as ethanol or ethanol/water mixtures.

In addition, WO 2007/093610 describes glucopyranosyl-substituted benzonitrile derivatives, pharmaceutical compositions containing such compounds, their medical uses as well as processes for their manufacture. It mentions that such glucopyranosyl-substituted benzonitrile derivatives can be formulated among other with one or more inert carriers and/or diluents, such as water/ethanol, water/glycerol, propylene glycol and the like. It further discloses among many other compounds also 1-cyano-2-(4-cyclopropyl-benzyl)-4-(β-D-glucopyranos-1-yl)-benzene (velagliflozin).

Further SGLT-2 inhibitors are described in WO 2007/128749 which relates to glucopyranosyl-substituted benzonitrile derivatives, pharmaceutical compositions containing such compounds, their medical uses as well as processes for their manufacture. It mentions that such glucopyranosyl-substituted benzonitrile derivatives can be formulated among other with one or more inert carriers and/or diluents, such as water/ethanol, water/glycerol, propylene glycol and the like. It further discloses among many other compounds also 1-cyano-2-(4-cyclopropyl-benzyl)-4-(β-D-glucopyranos-1-yl)-benzene (velagliflozin).

US 2011/077213 discloses methods for treating and/or preventing kidney stones, employing an SGLT-2 inhibitor alone, or in combination with a supply of carbohydrate, and/or in combination with a diuretic agent.

WO 2013/079501 is directed to crystalline dapagliflozin hydrate and a method for the preparation thereof. It discloses solutions of dapagliflozin in a solvent or a mixture of solvents and further specifies exemplarily suitable solvents such as water and C1-C4 alcohols or mixtures thereof.

WO 2014/016381 (US 2014/031540) describes crystalline complexes of 1-cyano-2-(4-cyclopropyl-benzyl)-4-(β-D-glucopyranos-1-yl)-benzene with natural amino acids, methods for the preparation thereof as well as the use thereof for preparing medicaments. It discloses solutions of 1-cyano-2-(4-cyclopropyl-benzyl)-4-(β-D-glucopyranos-1-yl)-benzene in a solvent or a mixture of solvents and further specifies exemplarily suitable organic solvents such as C1-C4 alkanols, ethanol and mixtures thereof, in particular with water.

Furthermore, WO 2014/195966 describes amorphous forms of canagliflozin and processes of manufacturing thereof as well as corresponding pharmaceutical compositions and their medicinal uses. It discloses solutions of canagliflozin in one or more organic solvents and further specifies exemplarily suitable organic solvents such as ethanol.

WO 2015/110402 relates to SGLT-2 inhibitors for use in the treatment and/or prevention of metabolic disorders in canine animals.

WO 2015/173584 discloses methods for avoiding an increase in glucagon secretion associated with the administration of a sodium glucose co-transporter 2 (SGLT-2) inhibitor via the co-administration of a dipeptidyl peptidase IV (DPP IV) inhibitor. Additionally, methods are disclosed for normalizing the glucagon secretion associated with the administration of a sodium glucose co-transporter 2 (SGLT-2) inhibitor via the co-administration of a dipeptidyl peptidase IV (DPP IV) inhibitor. The WO publication also relates to methods for treating diabetes, especially Type 2 diabetes, as well as hyperglycemia, hyperinsulinemia, obesity, hypertriglyceridemia, Syndrome X, diabetic complications, atherosclerosis and related diseases, comprising administering an SGLT-2 inhibitor and a dipeptidyl peptidase IV (DPP IV) inhibitor.

WO 2017/032799 deals with liquid pharmaceutical compositions comprising at least one SGLT-2 inhibitor and one or more polar organic solvents, wherein the one or more polar organic solvents preferably always comprise propane-1,2-diol (propylene glycol).

US 2017/145000 discloses canagliflozin monohydrate and its crystalline forms.

US 2020/237794 discloses one or more SGLT-2 inhibitors or pharmaceutically acceptable forms thereof for use in the treatment and/or prevention of a metabolic disorder of an equine animal, such as laminitis, vascular dysfunction, hypertension, hepatic lipidosis, atherosclerosis, hyperadrenocorticism, Pituitary Pars Intermedia Dysfunction and/or Equine Metabolic Syndrome.

WO 2020/219645 discloses methods of reducing the weight loss and/or increasing the weight of a feline in need thereof and/or methods of managing the disease of a feline with diabetes mellitus and elevated IGF-1 concentration, said methods include administering to a feline in need thereof a total daily dosage of about 2 to 50 mg of velagliflozin or a pharmaceutically acceptable form thereof.

WO 2021/105152 discloses the use of at least one SGLT-2 inhibitor in a non-human mammal, preferably ruminant, preferably for drying-off of a non-human mammal, preferably ruminant, as well as corresponding methods, such as improving and/or facilitating the drying-off of a non-human mammal, preferably ruminant, comprising administering to such non-human mammal, preferably ruminant, at least one SGLT-2 inhibitor.

WO 2021/165177 discloses the use of one or more SGLT-2 inhibitors or pharmaceutically acceptable forms thereof for the prophylaxis and/or treatment of one or more cardiac diseases in feline animals.

US 2022/016078 discloses a method of treating or preventing kidney stones in a patient: a therapeutically effective amount of a compound or a pharmaceutically acceptable salt, solvate or hydrate thereof which induces glucosuria or a pharmaceutical composition thereof is administered to the patient in need thereof.

WO 2023/006718 discloses the use of one or more SGLT-2 inhibitors or pharmaceutically acceptable forms thereof for the prophylaxis and/or treatment of one or more cardiac diseases in a non-human mammal/non-human mammal patient excluding a feline, in particular a canine/canine patient.

WO 2023/006745 discloses the use of one or more SGLT-2 inhibitors or pharmaceutically acceptable forms thereof for the prophylaxis and/or treatment of hypertension in a non-human mammal, preferably a carnivore, in particular a cat or a dog.

WO 2023/006747 discloses the use of one or more SGLT-2 inhibitors or pharmaceutically acceptable forms thereof for the prophylaxis and/or treatment of one or more renal diseases in a non-human mammal, such as a carnivore, in particular a cat or a dog.

Xu G et al. (Journal of Medical Chemistry 2014, 57: 1236-1251) is directed to the design, synthesis and biological evaluation of deuterated C-aryl glycosides as potent and long-acting renal SGLT-2 inhibitors for the treatment of type 2 diabetes.

Further challenges known in the prior art are the limited solubility of SGLT-2 inhibitors in water due to their positive $\log_{10} P$ values, which typically influences the bioavailability in the body of a patient or makes it difficult to find adequate solvents to get the substance dissolved in a liquid formulation before administering it into the body of a patient.

SUMMARY OF THE INVENTION

The present invention concerns an aqueous pharmaceutical composition comprising at least one SGLT-2 inhibitor and one or more solubilizing agents.

In the course of the present invention the term "aqueous" with regard to the term "pharmaceutical composition" refers to a water-containing pharmaceutical composition, wherein preferably such water is present in the form of an aqueous buffer, such as for instance citric acid buffer. However, any suitable aqueous buffer (system) can be used according to the knowledge and skills of the person skilled in the art. The water content/aqueous buffer content of such water-containing pharmaceutical composition is from 30 to 100 g/100 mL (30 to 100% w/v), preferably from 30 to 95 g/100 mL (30 to 95% w/v), more preferably from 30 to 90 g/100 mL (30 to 90% w/v), more preferably from 30 to 85 g/100 mL (30 to 85% w/v), even more preferably from 30 to 80 g/100 mL (30 to 80% w/v), most preferably from 50 to 80 g/100 mL (50 to 80% w/v).

The present invention also concerns an aqueous pharmaceutical composition as described and/or claimed herein, wherein the at least one SGLT-2 inhibitor is selected from the group consisting of:

(1) a glucopyranosyl-substituted benzene derivative of the formula (1)

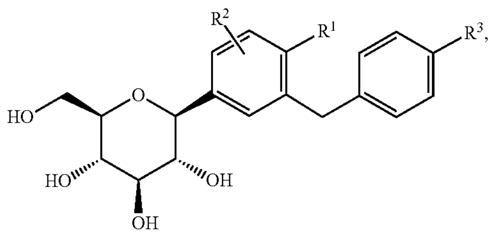

wherein $R^1$ denotes cyano, Cl or methyl (most preferably cyano); $R^2$ denotes H, methyl, methoxy or hydroxy (most preferably H) and $R^3$ denotes cyclopropyl, hydrogen, fluorine, chlorine, bromine, iodine, methyl, ethyl, propyl, isopropyl, butyl, sec-butyl, iso-butyl, tert-butyl, 3-methyl-but-1-yl, cyclobutyl, cyclopentyl, cyclohexyl, 1-hydroxy-cyclopropyl, 1-hydroxy-cyclobutyl, 1-hydroxy-cyclopentyl, 1-hydroxy-cyclohexyl, ethinyl, ethoxy, difluoromethyl, trifluoromethyl, pentafluoroethyl, 2-hydroxyl-ethyl, hydroxymethyl, 3-hydroxy-propyl, 2-hydroxy-2-methyl-prop-1-yl, 3-hydroxy-3-methyl-but-1-yl, 1-hydroxy-1-methyl-ethyl, 2,2,2-trifluoro-1-hydroxy-1-methyl-ethyl, 2,2,2-trifluoro-1-hydroxy-1-trifluoromethyl-ethyl, 2-methoxy-ethyl, 2-ethoxy-ethyl, hydroxy, difluoromethyloxy, trifluoromethyloxy, 2-methyloxy-ethyloxy, methylsulfanyl, methylsulfinyl, methlysulfonyl, ethylsulfinyl, ethylsulfonyl, trimethylsilyl, (R)-tetrahydrofuran-3-yloxy or (S)-tetrahydrofuran-3-yloxy or cyano;

wherein $R^3$ is preferably selected from cyclopropyl, ethyl, ethinyl, ethoxy, (R)-tetrahydrofuran-3-yloxy or (S)-tetrahydrofuran-3-yloxy; and most preferably $R^3$ is cyclopropyl, or a derivative thereof wherein one or more hydroxyl groups of the β-D-glucopyranosyl group are acylated with groups selected from ($C_{1-18}$-alkyl)carbonyl, ($C_{1-18}$-alkyl)oxycarbonyl, phenylcarbonyl and phenyl-($C_{1-3}$-alkyl)-carbonyl;

(2) Velagliflozin, represented by formula (2):
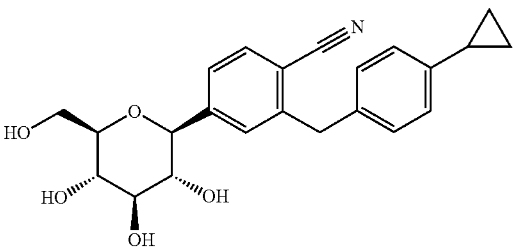 [SMILES: N#Cc1ccc([C@@H]2O[C@H](CO)[C@@H](O)[C@H](O)[C@H]2O)cc1Cc1ccc(C2CC2)cc1]
(3) Dapagliflozin, represented by formula (3):
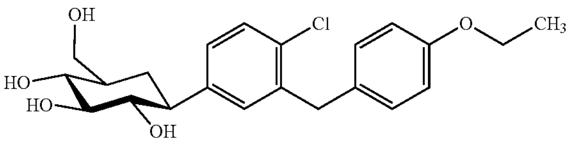
(4) Canagliflozin, represented by formula (4):
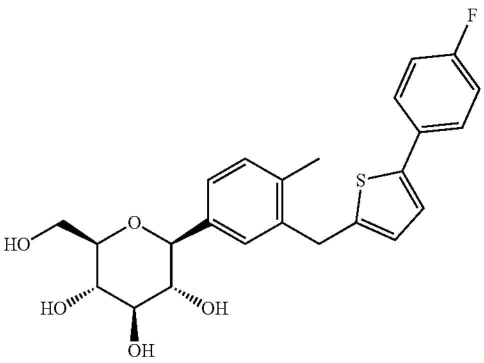 [SMILES: Cc1ccc([C@@H]2O[C@H](CO)[C@@H](O)[C@H](O)[C@H]2O)cc1Cc1ccc(-c2ccc(F)cc2)s1]
(5) Empagliflozin, represented by formula (5):
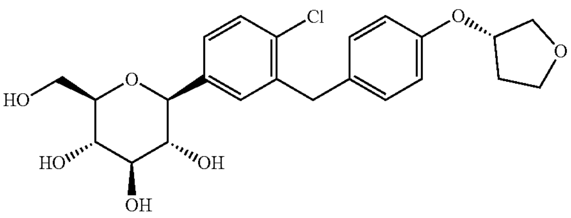
(6) Luseogliflozin, represented by formula (6):
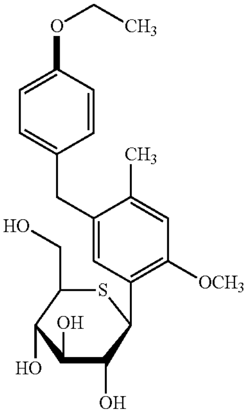
(7) Tofogliflozin, represented by formula (71:
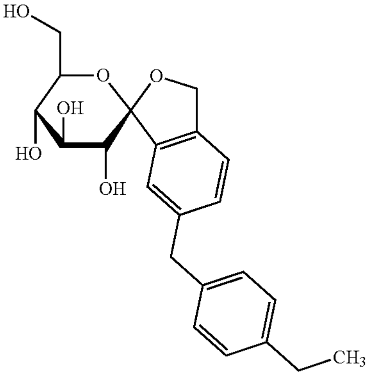
(8) Ipragliflozin, represented by formula (8):
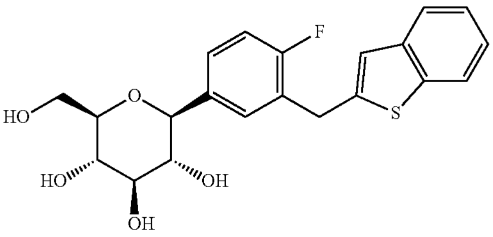 [SMILES: OC[C@H]1O[C@@H](c2ccc(F)c(Cc3cc4ccccc4s3)c2)[C@H](O)[C@@H](O)[C@@H]1O]
(9) Ertugliflozin, represented by formula (9):
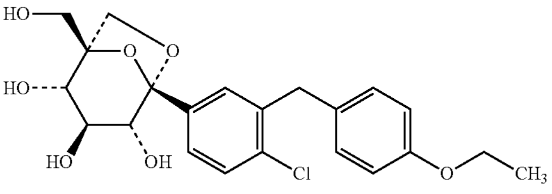 [SMILES: CCOc1ccc(Cc2cc([C@]34OC[C@](CO)(O3)[C@@H](O)[C@H](O)[C@H]4O)ccc2Cl)cc1]

(10) Atigliflozin, represented by formula (10):

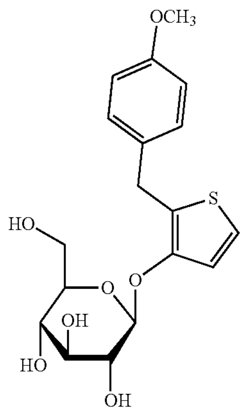

(11) Remogliflozin, represented by formula (11):

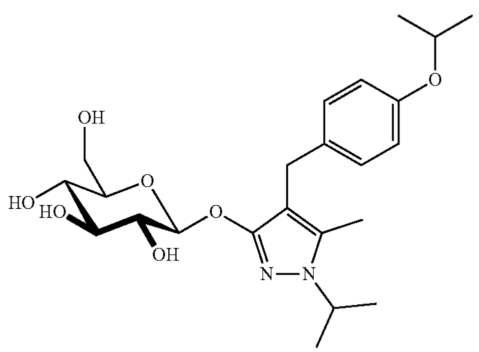

(11A) Remogliflozin etabonate, represented by formula (11A):

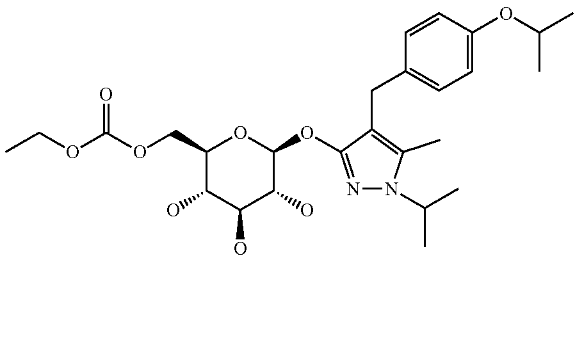 [SMILES: CCOC(=O)OC[C@H]1O[C@@H](Oc2nn(C(C)C)c(C)c2Cc2ccc(OC(C)C)cc2)[C@H](O)[C@@H](O)[C@@H]1O]

(12) a thiophene derivative of the formula (12)

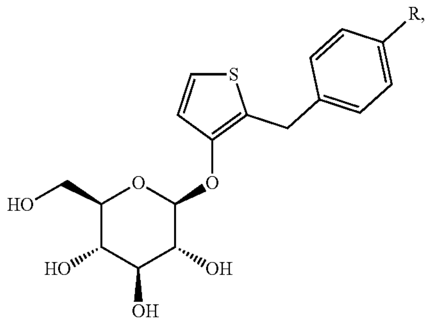

wherein R denotes methoxy or trifluoromethoxy;

(13) 1-(β-D-glucopyranosyl)-4-methyl-3-[5-(4-fluorophenyl)-2-thienylmethyl]benzene, represented by formula (13);

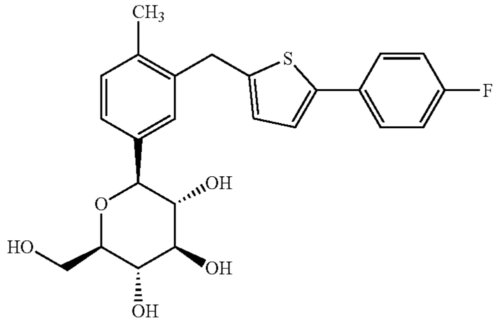 [SMILES: Cc1ccc([C@@H]2O[C@H](CO)[C@@H](O)[C@H](O)[C@H]2O)cc1Cc1ccc(-c2ccc(F)cc2)s1]

(14) a spiroketal derivative of the formula (14):

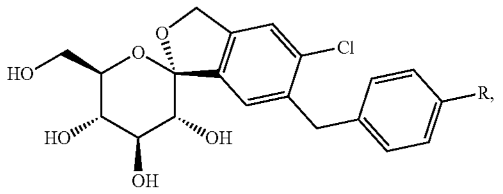

wherein R denotes methoxy, trifluoromethoxy, ethoxy, ethyl, isopropyl or tert. butyl;

(15) a pyrazole-O-glucoside derivative of the formula (15)

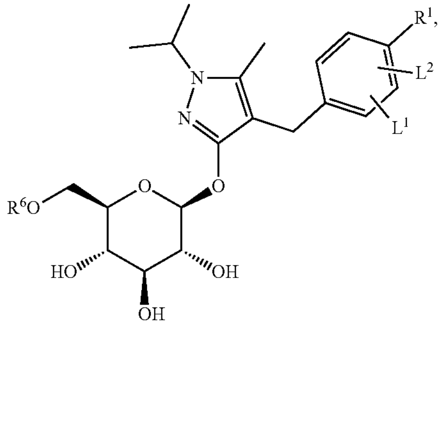

wherein $R^1$ denotes $C_{1-3}$-alkoxy, $L^1$, $L^2$ independently of each other denote H or F, $R^6$ denotes H, ($C_{1-3}$-alkyl)carbonyl, ($C_{1-6}$-alkyl)oxycarbonyl, phenyloxycarbonyl, benzyloxycarbonyl or benzylcarbonyl;

(16) Sotagliflozin, represented by formula (16):

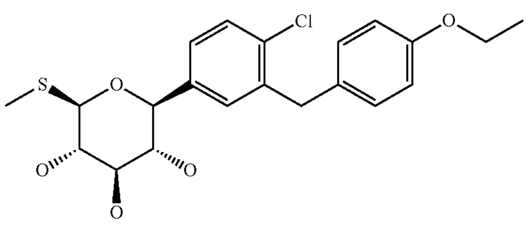 [SMILES: CCOc1ccc(Cc2cc([C@@H]3O[C@H](SC)[C@@H](O)[C@H](O)[C@H]3O)ccc2Cl)cc1]

(17) Sergliflozin, represented by formula (17):

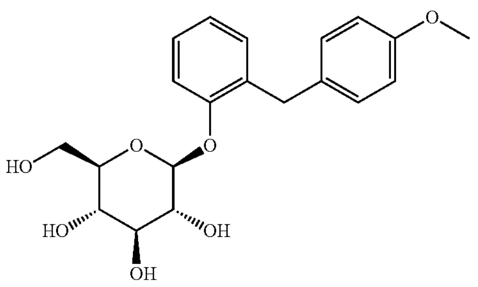 [SMILES: COc1ccc(Cc2ccccc2O[C@@H]2O[C@H](CO)[C@@H](O)[C@H](O)[C@H]2O)cc1]

(18) a compound represented by formula (18):

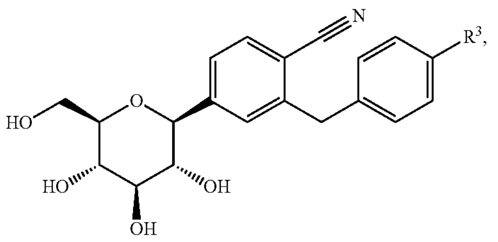

wherein $R^3$ denotes cyclopropyl, hydrogen, fluorine, chlorine, bromine, iodine, methyl, ethyl, propyl, isopropyl, butyl, sec-butyl, iso-butyl, tert-butyl, 3-methyl-but-1-yl, cyclobutyl, cyclopentyl, cyclohexyl, 1-hydroxy-cyclopropyl, 1-hydroxy-cyclobutyl, 1-hydroxy-cyclopentyl, 1-hydroxy-cyclohexyl, ethinyl, ethoxy, difluoromethyl, trifluoromethyl, pentafluoroethyl, 2-hydroxyl-ethyl, hydroxymethyl, 3-hydroxy-propyl, 2-hydroxy-2-methyl-prop-1-yl, 3-hydroxy-3-methyl-but-1-yl, 1-hydroxy-1-methyl-ethyl, 2,2,2-trifluoro-1-hydroxy-1-methyl-ethyl, 2,2,2-trifluoro-1-hydroxy-1-trifluoromethyl-ethyl, 2-methoxy-ethyl, 2-ethoxy-ethyl, hydroxy, difluoromethyloxy, trifluoromethyloxy, 2-methyloxy-ethyloxy, methylsulfanyl, methylsulfinyl, methlysulfonyl, ethylsulfinyl, ethylsulfonyl, trimethylsilyl, (R)-tetrahydrofuran-3-yloxy or (S)-tetrahydrofuran-3-yloxy or cyano, and wherein $R^3$ is preferably selected from cyclopropyl, ethyl, ethinyl, ethoxy, (R)-tetrahydrofuran-3-yloxy or (S)-tetrahydrofuran-3-yloxy; and $R^3$ most preferably is cyclopropyl, or a derivative thereof wherein one or more hydroxyl groups of the 3-D-glucopyranosyl group are acylated with groups selected from ($C_{1-18}$-alkyl)carbonyl, ($C_{1-18}$-alkyl)oxycarbonyl, phenylcarbonyl and phenyl-($C_{1-3}$-alkyl)-carbonyl;

(19) Bexagliflozin, represented by formula (19):

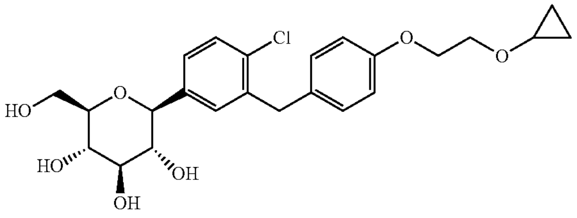 [SMILES: OC[C@H]1O[C@@H](c2ccc(Cl)c(Cc3ccc(OCCOC4CC4)cc3)c2)[C@H](O)[C@@H](O)[C@@H]1O]

(20) Janagliflozin, represented by formula (20):

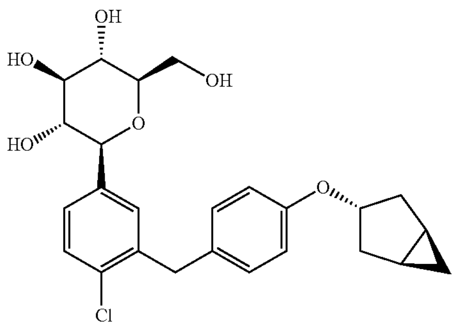 [SMILES: OC[C@H]1O[C@@H](c2ccc(Cl)c(Cc3ccc(O[C@H]4C[C@@H]5C[C@@H]5C4)cc3)c2)[C@H](O)[C@@H](O)[C@@H]1O]

(21) Rongliflozin, represented by formula (21):

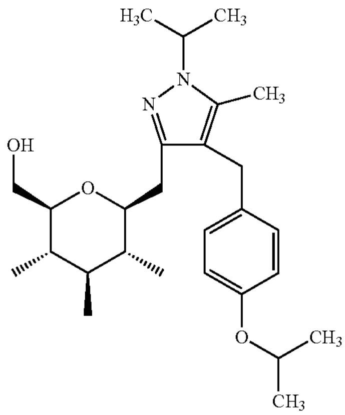 [SMILES: Cc1c(Cc2ccc(OC(C)C)cc2)c(C[C@@H]2O[C@H](CO)[C@@H](C)[C@H](C)[C@H]2C)nn1C(C)C]

(22) Wanpagliflozin;

(23) Enavogliflozin, represented by formula (23):

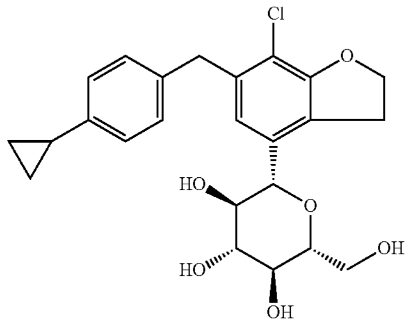 [SMILES: OC[C@H]1O[C@@H](c2cc(Cc3ccc(C4CC4)cc3)c(Cl)c3c2CCO3)[C@H](O)[C@@H](O)[C@@H]1O]

(24) TFC-039, represented by formula (24):

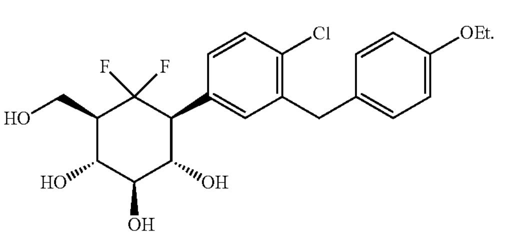 [SMILES: CCOc1ccc(Cc2cc([C@H]3[C@H](O)[C@@H](O)[C@H](O)[C@@H](CO)C3(F)F)ccc2Cl)cc1]

The present invention also concerns an aqueous pharmaceutical composition as described and/or claimed herein, wherein such aqueous pharmaceutical composition comprises only one SGLT-2 inhibitor, preferably only velagliflozin as single SGLT-2 inhibitor.

The present invention also concerns an aqueous pharmaceutical composition as described and/or claimed herein, wherein the at least one SGLT-2 inhibitor is velagliflozin, which preferably is the only SGLT-2 inhibitor contained in such aqueous pharmaceutical composition, and/or wherein the aqueous pharmaceutical composition is for, preferably direct, administration to a subject, preferably without further mandatory processing and/or purification steps, more preferably an animal, even more preferably a mammal, in particular a horse, cat, dog or cow; wherein preferably the aqueous pharmaceutical composition is sterile. The present invention also concerns an aqueous pharmaceutical composition as described and/or claimed herein for use in a method of treating and/or preventing one or more medicinal indications in a subject in need of such treatment and/or prevention, preferably an animal, more preferably a mammal, in particular a horse, cat, dog or cow, selected from among the medicinal indications:

(i) a metabolic disorder of an equine animal, wherein preferably the metabolic disorder is one or more disorders selected from insulin resistance, hyperinsulinemia, impaired glucose tolerance, dyslipidemia, dysadipokinemia, subclinical inflammation, systemic inflammation, low grade systemic inflammation, obesity, and/or regional adiposity, wherein preferably the metabolic disorder is insulin resistance, hyperinsulinemia, and/or a clinical condition associated with insulin resistance and/or hyperinsulinemia; wherein preferably said clinical condition is one or more conditions selected from impaired glucose tolerance, dyslipidemia, dysadipokinemia, subclinical inflammation, systemic inflammation, low grade systemic inflammation, obesity, and/or regional adiposity;

(ii) a metabolic disorder of an equine animal, wherein the metabolic disorder is one or more disorders selected from laminitis, vascular dysfunction, hypertension, hepatic lipidosis, atherosclerosis, hyperadrenocorticism, Pituitary Pars Intermedia Dysfunction and/or Equine Metabolic Syndrome, wherein preferably the metabolic disorder is a clinical condition/sign associated with insulin resistance and/or hyperinsulinemia, wherein said clinical condition/sign preferably is one or more conditions selected from laminitis, vascular dysfunction, hypertension, hepatic lipidosis, atherosclerosis, hyperadrenocorticism, Pituitary Pars Intermedia Dysfunction and/or Equine Metabolic Syndrome;

(iii) a metabolic disorder of a feline animal, wherein preferably the metabolic disorder is one or more selected from the group consisting of: ketoacidosis, pre-diabetes, diabetes mellitus type 1 or type 2, insulin resistance, acromegaly, diabetes with elevated IGF-1 concentration, obesity, hyperglycemia, impaired glucose tolerance, hyperinsulinemia, dyslipidemia, dysadipokinemia, subclinical inflammation, systemic inflammation, low grade systemic inflammation, hepatic lipidosis, atherosclerosis, inflammation of the pancreas, neuropathy and/or Syndrome X (metabolic syndrome) and/or loss of pancreatic beta cell function and/or wherein the remission of the metabolic disorder, preferably diabetic remission, is achieved and/or maintained;

(iv) a metabolic disorder of a canine animal, wherein preferably the metabolic disorder is one or more selected from the group consisting of: ketoacidosis, pre-diabetes, insulin dependent diabetes mellitus, insulin resistance diabetes, insulin resistance, obesity, hyperglycemia, hyperglycemia induced cataract formation, impaired glucose tolerance, hyperinsulinemia, dyslipidemia, dysadipokinemia, subclinical inflammation, systemic inflammation, low grade systemic inflammation, hepatic lipidosis, inflammation of the pancreas, metabolic disorder consequences, such as hypertension, renal dysfunction and/or musculoskeletal disorders, and/or Syndrome X (metabolic syndrome), preferably pre-diabetes, insulin dependent diabetes mellitus, insulin resistance diabetes, insulin resistance, wherein preferably the development of hyperglycemia induced cataract formation is prevented or remission is achieved and/or wherein preferably the development of metabolic disorder consequences, such as hypertension, renal dysfunction and/or musculoskeletal disorders, is prevented or progression is slowed or remission is achieved;

(v) a cardiac disease of a feline animal, wherein preferably the cardiac disease is one or more selected from the group consisting of: heart failure, heart failure due to one or more cardiomyopathies, heart failure due to hypertrophic cardiomyopathy (HCM), heart failure due to restrictive cardiomyopathy (RCM), heart failure due to dilated cardiomyopathy (DCM), heart failure due to unclassified cardiomyopathy (UCM), heart failure due to arrhythmogenic right ventricular cardiomyopathy (ARVC), hypertrophic cardiomyopathy (HCM), restrictive cardiomyopathy (RCM), dilated cardiomyopathy (DCM), unclassified cardiomyopathy (UCM), and/or arrhythmogenic right ventricular cardiomyopathy (ARVC); preferably selected from the group consisting of: heart failure due to one or more cardiomyopathies, heart failure due to hypertrophic cardiomyopathy (HCM), hypertrophic cardiomyopathy (HCM);

(vi) drying-off of a non-human mammal, preferably ruminant, improving and/or facilitating the drying-off of a non-human mammal, preferably ruminant, reducing the milk production, preferably milk production and/or secretion, in a pregnant and/or lactating non-human mammal, preferably ruminant, decreasing milk accumulation and/or engorgement in the udder, preferably udder and/or mammary gland, of a non-human mammal, preferably ruminant, decreasing the discomfort associated with udder engorgement, such as increasing the daily lying time and/or reduction of stress, of a non-human mammal, preferably ruminant, decreasing milk leakage after drying-off of a non-human mammal, preferably ruminant, decreasing the incidence of intramammary infections (IMI), preferably mastitis and/or metritis, in a non-human mammal, preferably ruminant;

(vii) a cardiac disease of a non-human mammal, excluding a feline, in particular a canine, wherein preferably the cardiac disease is one or more selected from the group consisting of: heart failure; congestive heart failure; asymptomatic/preclinical/occult heart failure; heart failure due to (myxomatous) mitral valve disease [(M)MVD]; congestive heart failure due to (myxomatous) mitral valve disease [(M)MVD]; asymptomatic/preclinical/occult heart failure due to (myxomatous) mitral valve disease [(M)MVD]; (myxomatous) mitral valve disease [(M)MVD]; clinically overt (myxomatous) mitral valve disease [(M)MVD]; asymptomatic/preclinical/occult (myxomatous) mitral valve disease [(M)MVD]; heart failure due to dilated cardiomyopathy (DCM); congestive heart failure due to dilated cardiomyopathy (DCM); asymptomatic/preclinical/occult heart failure due to dilated cardiomyopathy (DCM); dilated cardiomyopathy (DCM); clinically overt dilated cardiomyopathy (DCM); asymptomatic/preclinical/occult dilated cardiomyopathy (DCM); aortic stenosis (valvular, supravalvular and/or subvalvular);

(viii) hypertension in a non-human mammal, preferably a carnivore, more preferably a cat or a dog, wherein preferably the hypertension is one or more selected from the group consisting of: situational hypertension, secondary hypertension and idiopathic hypertension, wherein preferably the secondary hypertension is selected from the group consisting of hypertension associated with chronic kidney disease (CKD), diabetes, obesity, heart disease, endocrine disease, such as Cushing's disease, hyperthyroidism, acromegaly, and elevated blood pressure (BP) induced by medicaments, preferably by glucocorticoids, mineralocorticoids, erythropoiesis-stimulating agents, ephedrine and/or high dose sodium chloride;

(ix) a renal disease of a non-human mammal, preferably a carnivore, more preferably a cat or a dog, wherein preferably the renal disease is one or more selected from the group consisting of: renal dysplasia, glomerulopathy, polycystic kidney disease, amyloidosis, tubulo-nephritis/tubulointerstitial nephritis (TIN), acute kidney disease, chronic kidney disease.

The present invention further concerns a process for producing the aqueous pharmaceutical composition as described and claimed herein, comprising the steps:

(i) mixing the one or more organic solvents (if any), such as ethanol, with water (if no organic solvents are present, only water is used as starting material);

(ii) adding one or more solubilizing agents to the mixture (or water if no organic solvents are present) resulting from step (i);

(iii) dissolving the at least one SGLT-2 inhibitor, preferably velagliflozin, in the mixture resulting from step (ii);

(iv) optionally, dissolving the one or more preservatives in the mixture resulting from step (iii), (v) optionally, further dissolving further excipients, such as pH modifier(s), flavor(s), sweeteners, antioxidation agents, viscosity-enhancing agents and the like, in the mixture resulting from step (iii) or optionally (iv);

(vi) optionally, filtrating the mixture resulting from step (iii), optionally step (iv) or optionally step (v);

whereby, optionally, independently from each other after any of the individual process steps—be they mandatory or optional—an additional mixing step is performed.

In the course of the present invention, such process steps (i) to (vi) do not need to be carried out in the given order but can also be performed in any other meaningful order, e.g. (i), (v), (ii), (iii), (iv), (vi). It is within the knowledge of the skilled person to vary the order of process steps in order to obtain the desired process result, i.e. the aqueous pharmaceutical composition according to the present invention. For instance, if one or more viscosity-enhancing agents are added, it is preferred to heat the mixture up for complete dissolution of the one or more viscosity-enhancing agents. In turn such resulting mixture needs to be cooled down before the at least one SGLT-2 inhibitor, preferably velagliflozin (e.g., in the form of its L-proline-water cocrystal), is added in order to avoid unnecessary and unwanted degradation of the substance through such heating steps.

The present invention further concerns a kit-of-parts comprising:

(a) an aqueous pharmaceutical composition as described and claimed herein; and (b) a package leaflet including the information that the aqueous pharmaceutical composition is to be used for the prevention and/or treatment of one or more medicinal indications in a subject in need of such prevention and/or treatment, which are selected from among the medicinal indications:

(i) a metabolic disorder of an equine animal, wherein preferably the metabolic disorder is one or more disorders selected from insulin resistance, hyperinsulinemia, impaired glucose tolerance, dyslipidemia, dysadipokinemia, subclinical inflammation, systemic inflammation, low grade systemic inflammation, obesity, and/or regional adiposity, wherein preferably the metabolic disorder is insulin resistance, hyperinsulinemia, and/or a clinical condition associated with insulin resistance and/or hyperinsulinemia; wherein preferably said clinical condition is one or more conditions selected from impaired glucose tolerance, dyslipidemia, dysadipokinemia, subclinical inflammation, systemic inflammation, low grade systemic inflammation, obesity, and/or regional adiposity;

(ii) a metabolic disorder of an equine animal, wherein the metabolic disorder is one or more disorders selected from laminitis, vascular dysfunction, hypertension, hepatic lipidosis, atherosclerosis, hyperadrenocorticism, Pituitary Pars Intermedia Dysfunction and/or Equine Metabolic Syndrome, wherein preferably the metabolic disorder is a clinical condition/sign associated with insulin resistance and/or hyperinsulinemia, wherein said clinical condition/sign preferably is one or more conditions selected from laminitis, vascular dysfunction, hypertension, hepatic lipidosis, atherosclerosis, hyperadrenocorticism, Pituitary Pars Intermedia Dysfunction and/or Equine Metabolic Syndrome;

(iii) a metabolic disorder of a feline animal, wherein preferably the metabolic disorder is one or more selected from the group consisting of: ketoacidosis, pre-diabetes, diabetes mellitus type 1 or type 2, insulin resistance, acromegaly, diabetes with elevated IGF-1 concentration, obesity, hyperglycemia, impaired glucose tolerance, hyperinsulinemia, dyslipidemia, dysadipokinemia, subclinical inflammation, systemic inflammation, low grade systemic inflammation, hepatic lipidosis, atherosclerosis, inflammation of the pancreas, neuropathy and/or Syndrome X (metabolic syndrome) and/or loss of pancreatic beta cell function and/or wherein the remission of the metabolic disorder, preferably diabetic remission, is achieved and/or maintained;

(iv) a metabolic disorder of a canine animal, wherein preferably the metabolic disorder is one or more selected from the group consisting of: ketoacidosis, pre-diabetes, insulin dependent diabetes mellitus, insulin resistance diabetes, insulin resistance, obesity, hyperglycemia, hyperglycemia induced cataract formation, impaired glucose tolerance, hyperinsulinemia, dyslipidemia, dysadipokinemia, subclinical inflammation, systemic inflammation, low grade systemic inflammation, hepatic lipidosis, inflammation of the pancreas, metabolic disorder consequences, such as hypertension, renal dysfunction and/or musculoskeletal disorders, and/or Syndrome X (metabolic syndrome), preferably pre-diabetes, insulin dependent diabetes mellitus, insulin resistance diabetes, insulin resistance, wherein preferably the development of hyperglycemia induced cataract formation is prevented or remission is achieved and/or wherein preferably the development of metabolic disorder consequences, such as hypertension, renal dysfunction and/or musculoskeletal disorders, is prevented or progression is slowed or remission is achieved.

(v) a cardiac disease of a feline animal, wherein preferably the cardiac disease is one or more selected from the group consisting of: heart failure, heart failure due to one or more cardiomyopathies, heart failure due to hypertrophic cardiomyopathy (HCM), heart failure due to restrictive cardiomyopathy (RCM), heart failure due to dilated cardiomyopathy (DCM), heart failure due to unclassified cardiomyopathy (UCM), heart failure due to arrhythmogenic right ventricular cardiomyopathy (ARVC), hypertrophic cardiomyopathy (HCM), restrictive cardiomyopathy (RCM), dilated cardiomyopathy (DCM), unclassified cardiomyopathy (UCM), and/or arrhythmogenic right ventricular cardiomyopathy (ARVC); preferably selected from the group consisting of: heart failure due to one or more cardiomyopathies, heart failure due to hypertrophic cardiomyopathy (HCM), hypertrophic cardiomyopathy (HCM);

(vi) drying-off of a non-human mammal, preferably ruminant, improving and/or facilitating the drying-off of a non-human mammal, preferably ruminant, reducing the milk production, preferably milk production and/or secretion, in a pregnant and/or lactating non-human mammal, preferably ruminant, decreasing milk accumulation and/or engorgement in the udder, preferably udder and/or mammary gland, of a non-human mammal, preferably ruminant, decreasing the discomfort associated with udder engorgement, such as increasing the daily lying time and/or reduction of stress, of a non-human mammal, preferably ruminant, decreasing milk leakage after drying-off of a non-human mammal, preferably ruminant, decreasing the incidence of intramammary infections (IMI), preferably mastitis and/or metritis, in a non-human mammal, preferably ruminant (vii) a cardiac disease of a non-human mammal, excluding a feline, in particular a canine, wherein preferably the cardiac disease is one or more selected from the group consisting of: heart failure; congestive heart failure; asymptomatic/preclinical/occult heart failure; heart failure due to (myxomatous) mitral valve disease [(M)MVD]; congestive heart failure due to (myxomatous) mitral valve disease [(M)MVD]; asymptomatic/preclinical/occult heart failure due to (myxomatous) mitral valve disease [(M)MVD]; (myxomatous) mitral valve disease [(M)MVD]; clinically overt (myxomatous) mitral valve disease [(M)MVD]; asymptomatic/preclinical/occult (myxomatous) mitral valve disease [(M)MVD]; heart failure due to dilated cardiomyopathy (DCM); congestive heart failure due to dilated cardiomyopathy (DCM); asymptomatic/preclinical/occult heart failure due to dilated cardiomyopathy (DCM); dilated cardiomyopathy (DCM); clinically overt dilated cardiomyopathy (DCM); asymptomatic/preclinical/occult dilated cardiomyopathy (DCM); aortic stenosis (valvular, supravalvular and/or subvalvular);

(viii) hypertension in a non-human mammal, preferably a carnivore, more preferably a cat or a dog, wherein preferably the hypertension is one or more selected from the group consisting of: situational hypertension, secondary hypertension and idiopathic hypertension, wherein preferably the secondary hypertension is selected from the group consisting of hypertension associated with chronic kidney disease (CKD), diabetes, obesity, heart disease, endocrine disease, such as Cushing's disease, hyperthyroidism, acromegaly, and elevated blood pressure (BP) induced by medicaments, preferably by glucocorticoids, mineralocorticoids, erythropoiesis-stimulating agents, ephedrine and/or high dose sodium chloride;

(ix) a renal disease of a non-human mammal, preferably a carnivore, more preferably a cat or a dog, wherein preferably the renal disease is one or more selected from the group consisting of: renal dysplasia, glomerulopathy, polycystic kidney disease, amyloidosis, tubulo-nephritis/tubulointerstitial nephritis (TIN), acute kidney disease, chronic kidney disease.

The advantages of the aqueous pharmaceutical compositions according to the present invention are as follows:

They are suitable for, preferably direct, administration to a subject, preferably without further mandatory processing and/or purification steps. Preferably, they are therefore sterile and comply with GMP manufacturing conditions as well as GCP compliant clinical protocols;

They are stable against undesired contamination by/growth of microorganisms;

They are preferably true solutions, emulsions or suspensions, more preferably true solutions, in an aqueous based system with a minimum amount of organic solvents (if any) ensuring biocompatibility and reduction in costs.

DETAILED DESCRIPTION OF THE INVENTION

Before the embodiments of the present invention are described in further details it shall be noted that as used herein and in the appended claims, the singular forms "a", "an", and "the" include plural reference unless the context clearly dictates otherwise.

Unless defined otherwise, all technical and scientific terms used herein have the same meanings as commonly understood by one of ordinary skill in the art to which this invention belongs. All given ranges and values may vary by 1 to 5% unless indicated otherwise or known otherwise by the person skilled in the art, therefore, the term "about" was usually omitted from the description and claims. Although any methods and materials similar or equivalent to those described herein can be used in the practice or testing of the present invention, the preferred methods, devices, and materials are now described. All publications mentioned herein are incorporated herein by reference for the purpose of describing and disclosing the substances, excipients, carriers, and methodologies as reported in the publications which might be used in connection with the invention. Nothing herein is to be construed as an admission that the invention is not entitled to antedate such disclosure by virtue of prior invention.

The at least one SGLT-2 inhibitor according to the invention includes, but is not limited to, glucopyranosyl-substituted benzene derivatives, for example as described in WO 01/27128, WO 03/099836, WO 2005/092877, WO 2006/034489, WO 2006/064033, WO 2006/117359, WO 2006/117360, WO 2007/025943, WO 2007/028814, WO 2007/031548, WO 2007/093610, WO 2007/128749, WO 2008/049923, WO 2008/055870, WO 2008/055940, WO 2009/022020 or WO 2009/022008.

Moreover, the at least one SGLT-2 inhibitor according to the invention may be selected from the group consisting of the following compounds or pharmaceutically acceptable (crystalline) forms thereof:

(1) a glucopyranosyl-substituted benzene derivative of the formula (1)

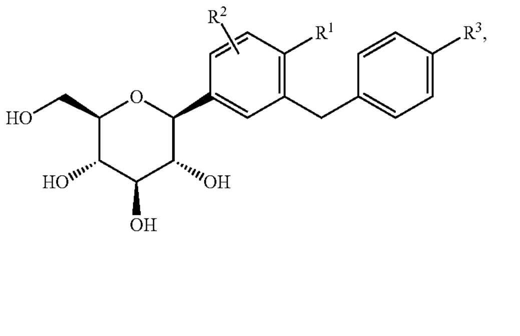

wherein R denotes cyano, C or methyl most preferably cyano);

$R^2$ denotes H, methyl, methoxy or hydroxy (most preferably H) and $R^3$ denotes cyclopropyl, hydrogen, fluorine, chlorine, bromine, iodine, methyl, ethyl, propyl, isopropyl, butyl, sec-butyl, iso-butyl, tert-butyl, 3-methyl-but-1-yl, cyclobutyl, cyclopentyl, cyclohexyl, 1-hydroxy-cyclopropyl, 1-hydroxy-cyclobutyl, 1-hydroxy-cyclopentyl, 1-hydroxy-cyclohexyl, ethinyl, ethoxy, difluoromethyl, trifluoromethyl, pentafluoroethyl, 2-hydroxyl-ethyl, hydroxymethyl, 3-hydroxy-propyl, 2-hydroxy-2-methyl-prop-1-yl, 3-hydroxy-3-methyl-but-1-yl, 1-hydroxy-1-methyl-ethyl, 2,2,2-trifluoro-1-hydroxy-1-methyl-ethyl, 2,2,2-trifluoro-1-hydroxy-1-trifluoromethyl-ethyl, 2-methoxy-ethyl, 2-ethoxy-ethyl, hydroxy, difluoromethyloxy, trifluoromethyloxy, 2-methyloxy-ethyloxy, methylsulfanyl, methylsulfinyl, methlysulfonyl, ethylsulfinyl, ethylsulfonyl, trimethylsilyl, (R)-tetrahydrofuran-3-yloxy or (S)-tetrahydrofuran-3-yloxy or cyano;

wherein $R^3$ is preferably selected from cyclopropyl, ethyl, ethinyl, ethoxy, (R)-tetrahydrofuran-3-yloxy or (S)-tetrahydrofuran-3-yloxy; and most preferably $R^3$ is cyclopropyl, or a derivative thereof wherein one or more hydroxyl groups of the 3-D-glucopyranosyl group are acylated with groups selected from ($C_{1-18}$-alkyl)carbonyl, ($C_{1-18}$-alkyl)oxycarbonyl, phenylcarbonyl and phenyl-($C_{1-3}$-alkyl)-carbonyl;

(2) Velagliflozin, represented by formula (2):

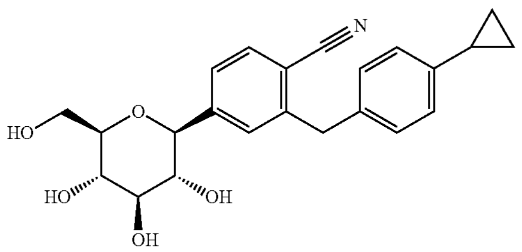 [SMILES: N#Cc1ccc([C@@H]2O[C@H](CO)[C@@H](O)[C@H](O)[C@H]2O)cc1Cc1ccc(C2CC2)cc1]

(3) Dapagliflozin, represented by formula (3):

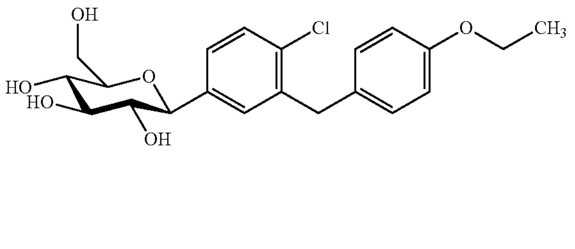

(4) Canagliflozin, represented by formula (4):
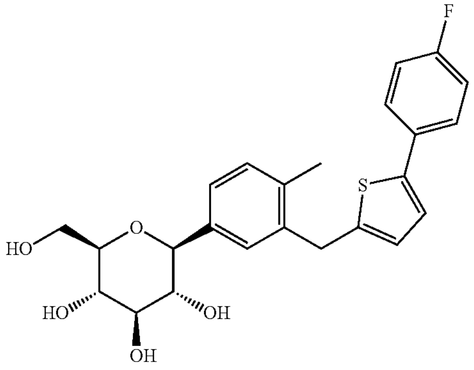 [SMILES: Cc1ccc([C@@H]2O[C@H](CO)[C@@H](O)[C@H](O)[C@H]2O)cc1Cc1ccc(-c2ccc(F)cc2)s1]
(5) Empagliflozin, represented by formula (5):
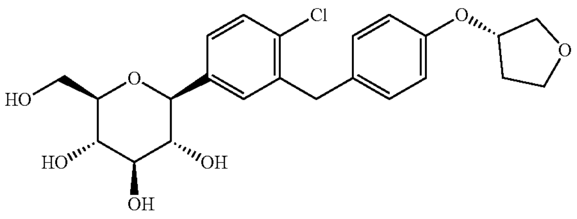 [SMILES: OC[C@H]1O[C@@H](c2ccc(Cl)c(Cc3ccc(O[C@H]4CCOC4)cc3)c2)[C@H](O)[C@@H](O)[C@@H]1O]
(6) Luseogliflozin, represented by formula (6):
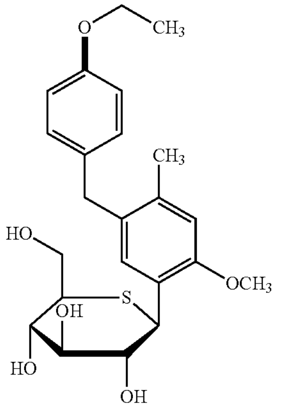
(7) Tofogliflozin, represented by formula (7):
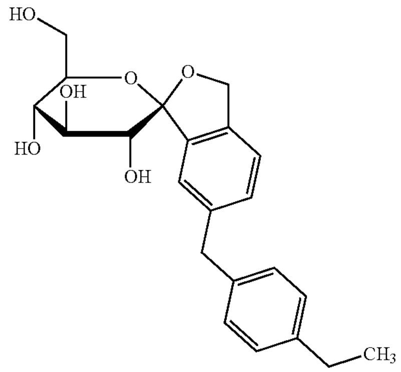
(8) Ipragliflozin, represented by formula (8):
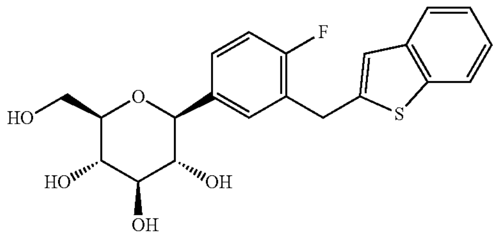 [SMILES: OC[C@H]1O[C@@H](c2ccc(F)c(Cc3cc4ccccc4s3)c2)[C@H](O)[C@@H](O)[C@@H]1O]
(9) Ertugliflozin, represented by formula (9):
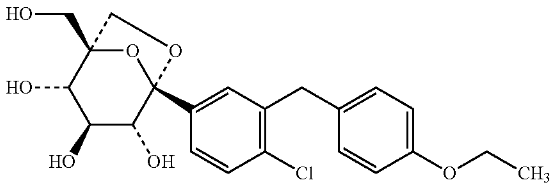 [SMILES: CCOc1ccc(Cc2cc([C@]34OC[C@](CO)(O3)[C@@H](O)[C@H](O)[C@H]4O)ccc2Cl)cc1]
(10) Atigliflozin, represented by formula (10):
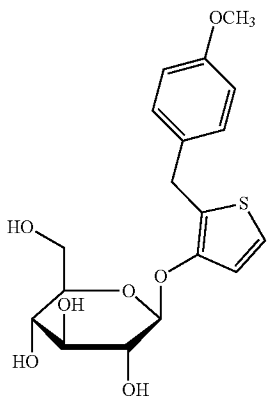

(11) Remogliflozin, represented by formula (11):

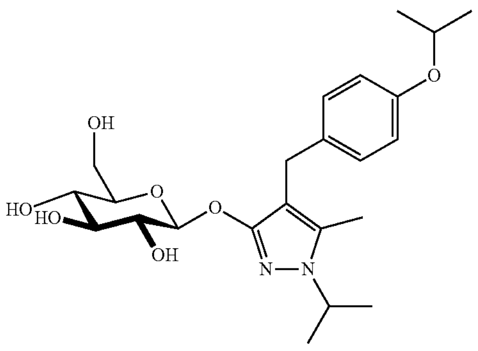

(11A) Remogliflozin etabonate, represented by formula (11A):

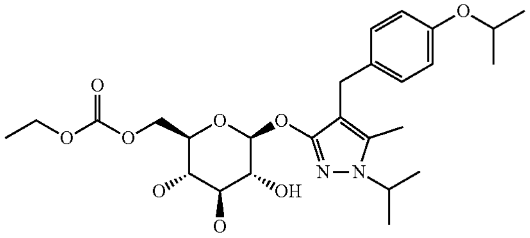 [SMILES: CCOC(=O)OC[C@H]1O[C@@H](Oc2nn(C(C)C)c(C)c2Cc2ccc(OC(C)C)cc2)[C@H](O)[C@@H](O)[C@@H]1O]

(12) a thiophene derivative of the formula (12)

(7-1)

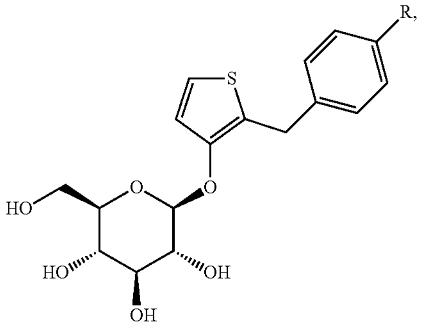

wherein R denotes methoxy or trifluoromethoxy;

(13) 1-(β-D-glucopyranosyl)-4-methyl-3-[5-(4-fluoro-phenyl)-2-thienylmethyl]benzene, represented by formula (13);

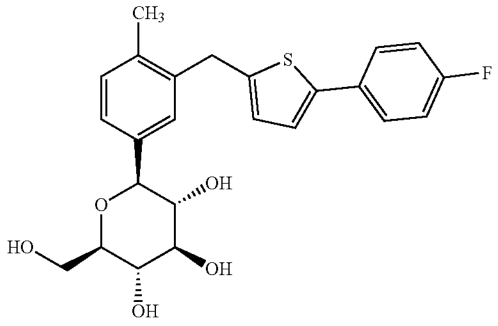 [SMILES: Cc1ccc([C@@H]2O[C@H](CO)[C@@H](O)[C@H](O)[C@H]2O)cc1Cc1ccc(-c2ccc(F)cc2)s1]

(14) a spiroketal derivative of the formula (14):

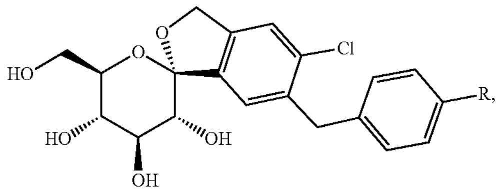

wherein R denotes methoxy, trifluoromethoxy, ethoxy, ethyl, isopropyl or tert. butyl;

(15) a pyrazole-O-glucoside derivative of the formula (15)

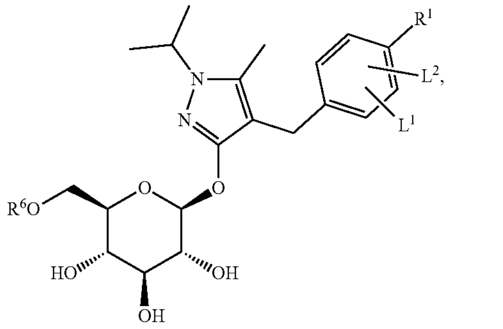

wherein $R^1$ denotes $C_{1-3}$-alkoxy, $L^1$, $L^2$ independently of each other denote H or F, $R^6$ denotes H, ($C_{1-3}$-alkyl)carbonyl, ($C_{1-6}$-alkyl)oxy-carbonyl, phenyloxycarbonyl, benzyloxycarbonyl or benzylcarbonyl;

(16) Sotagliflozin, represented by formula (16):

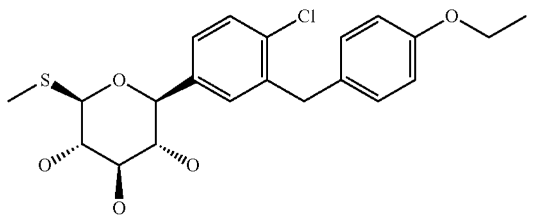 [SMILES: CCOc1ccc(Cc2cc([C@@H]3O[C@H](SC)[C@@H](O)[C@H](O)[C@H]3O)ccc2Cl)cc1]

(17) Sergliflozin, represented by formula (17):

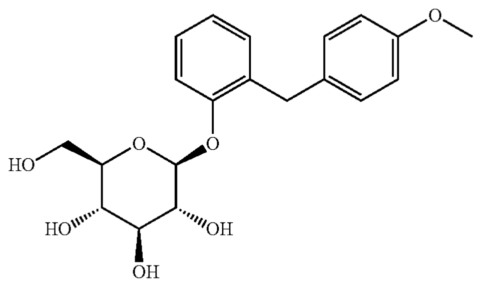 [SMILES: COc1ccc(Cc2ccccc2O[C@@H]2O[C@H](CO)[C@@H](O)[C@H](O)[C@H]2O)cc1]

(18) a compound represented by formula (18):

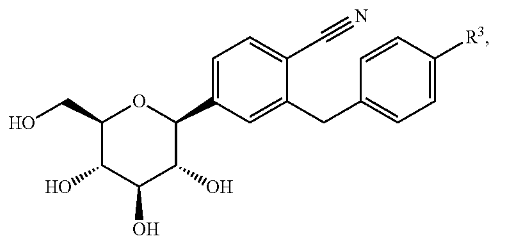

wherein $R^3$ denotes cyclopropyl, hydrogen, fluorine, chlorine, bromine, iodine, methyl, ethyl, propyl, isopropyl, butyl, sec-butyl, iso-butyl, tert-butyl, 3-methyl-but-1-yl, cyclobutyl, cyclopentyl, cyclohexyl, 1-hydroxy-cyclopropyl, 1-hydroxy-cyclobutyl, 1-hydroxy-cyclopentyl, 1-hydroxy-cyclohexyl, ethinyl, ethoxy, difluoromethyl, trifluoromethyl, pentafluoroethyl, 2-hydroxyl-ethyl, hydroxymethyl, 3-hydroxy-propyl, 2-hydroxy-2-methyl-prop-1-yl, 3-hydroxy-3-methyl-but-1-yl, 1-hydroxy-1-methyl-ethyl, 2,2,2-trifluoro-1-hydroxy-1-methyl-ethyl, 2,2,2-trifluoro-1-hydroxy-1-trifluoromethyl-ethyl, 2-methoxy-ethyl, 2-ethoxy-ethyl, hydroxy, difluoromethyloxy, trifluoromethyloxy, 2-methyloxy-ethyloxy, methylsulfanyl, methylsulfinyl, methlysulfonyl, ethylsulfinyl, ethylsulfonyl, trimethylsilyl, (R)-tetrahydrofuran-3-yloxy or (S)-tetrahydrofuran-3-yloxy or cyano; and wherein $R^3$ is preferably selected from cyclopropyl, ethyl, ethinyl, ethoxy, (R)-tetrahydrofuran-3-yloxy or (S)-tetrahydrofuran-3-yloxy; and $R^3$ most preferably is cyclopropyl, or a derivative thereof wherein one or more hydroxyl groups of the β-D-glucopyranosyl group are acylated with groups selected from ($C_{1-18}$-alkyl)carbonyl, ($C_{1-18}$-alkyl)oxycarbonyl, phenylcarbonyl and phenyl-($C_{1-3}$-alkyl)-carbonyl;

(19) Bexagliflozin, represented by formula (19):

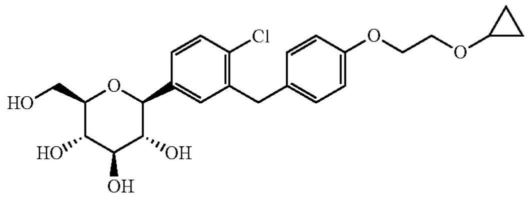 [SMILES: OC[C@H]1O[C@@H](c2ccc(Cl)c(Cc3ccc(OCCOC4CC4)cc3)c2)[C@H](O)[C@@H](O)[C@@H]1O]

(20) Janagliflozin, represented by formula (20):

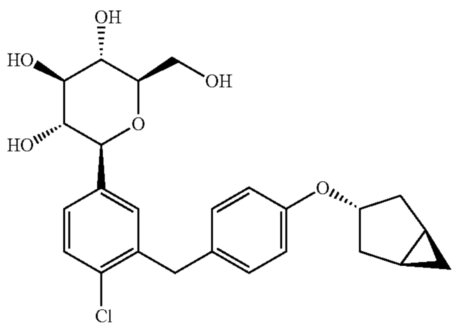 [SMILES: OC[C@H]1O[C@@H](c2ccc(Cl)c(Cc3ccc(O[C@H]4C[C@@H]5C[C@@H]5C4)cc3)c2)[C@H](O)[C@@H](O)[C@@H]1O]

(21) Rongliflozin, represented by formula (21):

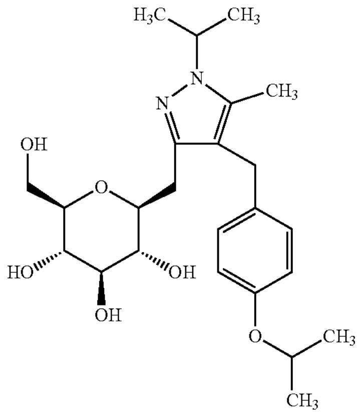 [SMILES: Cc1c(Cc2ccc(OC(C)C)cc2)c(C[C@@H]2O[C@H](CO)[C@@H](O)[C@H](O)[C@H]2O)nn1C(C)C]

(22) Wanpagliflozin

(23) Enavogliflozin, represented by formula (23):

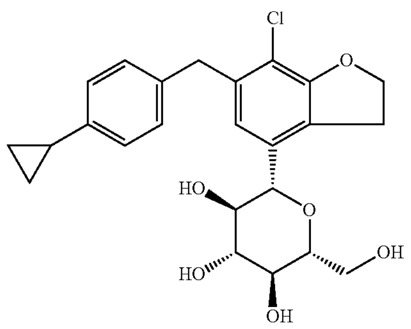 [SMILES: OC[C@H]1O[C@@H](c2cc(Cc3ccc(C4CC4)cc3)c(Cl)c3c2CCO3)[C@H](O)[C@@H](O)[C@@H]1O]

(24) TFC-039, represented by formula (24):

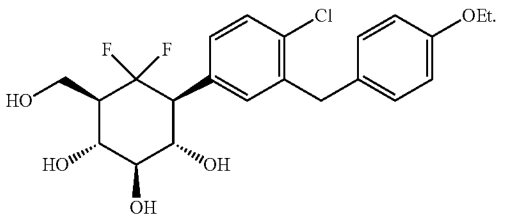 [SMILES: CCOc1ccc(Cc2cc([C@H]3[C@H](O)[C@@H](O)[C@H](O)[C@@H](CO)C3(F)F)ccc2Cl)cc1]

The term "velagliflozin" as employed herein refers to velagliflozin of the above structure as well as pharmaceutically acceptable forms thereof, including hydrates and solvates thereof, and crystalline forms thereof. The compound, methods of its synthesis and co-crystals thereof are described in WO 2007/128749, WO 2014/016381 and WO 2019/121509 for example.

The term "dapagliflozin" as employed herein refers to dapagliflozin of the above structure as well as pharmaceutically acceptable forms thereof, including hydrates and solvates thereof, and crystalline forms thereof. The compound and methods of its synthesis are described in WO 03/099836 for example. Preferred hydrates, solvates and crystalline forms are described in the patent applications WO 2008/116179 and WO 2008/002824 for example.

The term "canagliflozin" as employed herein refers to canagliflozin of the above structure as well as pharmaceutically acceptable forms thereof, including hydrates and solvates thereof, and crystalline forms thereof. The compound and methods of its synthesis are described in WO 2005/012326 and WO 2009/035969 for example. Preferred hydrates, solvates and crystalline forms are described in the patent application WO 2008/069327 for example.

The term "empagliflozin" as employed herein refers to empagliflozin of the above structure as well as pharmaceutically acceptable forms thereof, including hydrates and solvates thereof, and crystalline forms thereof. The compound and methods of its synthesis are described in WO 2005/092877, WO 2006/120208 and WO 2011/039108 for example. A preferred crystalline form is described in the patent applications WO 2006/117359 and WO 2011/039107 for example.

The term "atigliflozin" as employed herein refers to atigliflozin of the above structure as well as pharmaceutically acceptable forms thereof, including hydrates and solvates thereof, and crystalline forms thereof. The compound and methods of its synthesis are described in WO 2004/007517 for example.

The term "ipragliflozin" as employed herein refers to ipragliflozin of the above structure as well as pharmaceutically acceptable forms thereof, including hydrates and solvates thereof, and crystalline forms thereof. The compound and methods of its synthesis are described in WO 2004/080990, WO 2005/012326 and WO 2007/114475 for example.

The term "tofogliflozin" as employed herein refers to tofogliflozin of the above structure as well as pharmaceutically acceptable forms thereof, including hydrates and solvates thereof, and crystalline forms thereof. The compound and methods of its synthesis are described in WO 2007/140191 and WO 2008/013280 for example.

The term "luseogliflozin" as employed herein refers to luseogliflozin of the above structure as well as pharmaceutically acceptable forms thereof, including hydrates and solvates thereof, and crystalline forms thereof.

The term "ertugliflozin" as employed herein refers to ertugliflozin of the above structure as well as pharmaceutically acceptable forms thereof, including hydrates and solvates thereof, and crystalline forms thereof. The compound is described for example in WO 2010/023594.

The term "remogliflozin" as employed herein refers to remogliflozin of the above structure as well as pharmaceutically acceptable forms thereof, including prodrugs of remogliflozin, in particular remogliflozin etabonate, including hydrates and solvates thereof, and crystalline forms thereof. Methods of its synthesis are described in the patent applications EP 1 213 296 and EP 1 354 888 for example.

The term "sergliflozin" as employed herein refers to sergliflozin of the above structure as well as pharmaceutically acceptable forms thereof, including prodrugs of sergliflozin, in particular sergliflozin etabonate, including hydrates and solvates thereof, and crystalline forms thereof. Methods for its manufacture are described in the patent applications EP 1 344 780 and EP 1 489 089 for example.

The compound of formula (16) above, i.e. sotagliflozin, and its manufacture are described for example in WO 2008/042688 or WO 2009/014970.

The term "bexagliflozin" as employed herein refers to bexagliflozin of the above structure as well as pharmaceutically acceptable forms thereof, including hydrates and solvates thereof, and crystalline forms thereof. The compound and methods of its synthesis are described in WO 2009/026537 for example.

The term "TFC-039" as employed herein refers to the above structure as well as pharmaceutically acceptable forms thereof, including hydrates and solvates thereof, and crystalline forms thereof. The compound and methods of its synthesis are described in WO 2012/160218 for example.

Preferred SGLT-2 inhibitors are glucopyranosyl-substituted benzene derivatives. Optionally, one or more hydroxyl groups of the glucopyranosyl group in such one or more SGLT-2 inhibitors may be acylated with groups selected from ($C_{1-18}$-alkyl)carbonyl, ($C_{1-18}$-alkyl)oxycarbonyl, phenylcarbonyl and phenyl-($C_{1-3}$-alkyl)-carbonyl.

More preferred are glucopyranosyl-substituted benzonitrile derivatives of formula (1) as disclosed herein above. Yet more preferred are glucopyranosyl-substituted benzonitrile derivatives of formula (18):

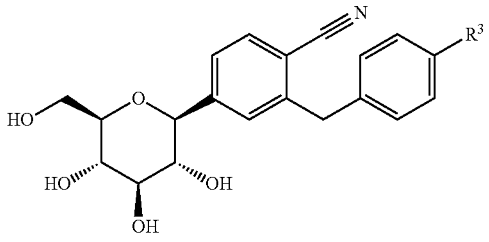

wherein $R^3$ denotes cyclopropyl, hydrogen, fluorine, chlorine, bromine, iodine, methyl, ethyl, propyl, isopropyl, butyl, sec-butyl, iso-butyl, tert-butyl, 3-methyl-but-1-yl, cyclobutyl, cyclopentyl, cyclohexyl, 1-hydroxy-cyclopropyl, 1-hydroxy-cyclobutyl, 1-hydroxy-cyclopentyl, 1-hydroxy-cyclohexyl, ethinyl, ethoxy, difluoromethyl, trifluoromethyl, pentafluoroethyl, 2-hydroxyl-ethyl, hydroxymethyl, 3-hydroxy-propyl, 2-hydroxy-2-methyl-prop-1-yl, 3-hydroxy-3-methyl-but-1-yl, 1-hydroxy-1-methyl-ethyl, 2,2,2-trifluoro-1-hydroxy-1-methyl-ethyl, 2,2,2-trifluoro-1-hydroxy-1-trifluoromethyl-ethyl, 2-methoxy-ethyl, 2-ethoxy-ethyl, hydroxy, difluoromethyloxy, trifluoromethyloxy, 2-methyloxy-ethyloxy, methylsulfanyl, methylsulfinyl, methlysulfonyl, ethylsulfinyl, ethylsulfonyl, trimethylsilyl, (R)-tetrahydrofuran-3-yloxy or (S)-tetrahydro-furan-3-yloxy or cyano; and wherein $R^3$ is preferably selected from cyclopropyl, ethyl, ethinyl, ethoxy, (R)-tetrahydrofuran-3-yloxy or (S)-tetrahydrofuran-3-yloxy; and $R^3$ most preferably is cyclopropyl, or a derivative thereof wherein one or more hydroxyl groups of the β-D-glucopyranosyl group are acylated with groups selected from ($C_{1-18}$-alkyl)carbonyl, ($C_{1-18}$-alkyl)oxycarbonyl, phenylcarbonyl and phenyl-($C_{1-3}$-alkyl)-carbonyl.

Preferably, such SGLT-2 inhibitor is velagliflozin as shown in formula (2). Optionally, one or more hydroxyl groups of the β-D-glucopyranosyl group of velagliflozin may be acylated with groups selected from ($C_{1-18}$-alkyl) carbonyl, ($C_{1-18}$-alkyl)oxycarbonyl, phenylcarbonyl and phenyl-($C_{1-3}$-alkyl)-carbonyl.

Thus, in a preferred embodiment, the at least one SGLT-2 inhibitor according to the present invention is a glucopyranosyl-substituted benzene derivative SGLT-2 inhibitor, preferably a SGLT-2 inhibitor of formula (1), more preferably of formula (18), or yet more preferably of formula (2), i.e. velagliflozin, in each case as defined herein above.

In the course of the present invention 1-cyano-2-(4-cyclopropyl-benzyl)-4-(β-D-glucopyranos-1-yl)-benzene (velagliflozin) is also referred to as "the substance" and is herewith understood to also comprise co-crystal 1-cyano-2-(4-cyclopropyl-benzyl)-4-(β-D-glucopyranos-1-yl)-benzene-L-proline as well as the 1:1:1-co-crystal 1-cyano-2-(4-cyclopropyl-benzyl)-4-(β-D-glucopyranos-1-yl)-benzene-L-proline-water (as disclosed in WO 2014/016381). Generally, in the case of disclosed and claimed concentrations (% w/v) and amounts (g, mg) the concentration or amount always refers to 1-cyano-2-(4-cyclopropyl-benzyl)-4-(β-D-glucopyranos-1-yl)-benzene as such, i.e. excluding L-proline and crystal water, unless otherwise explicitly stated—even though in practice (and in the example section) 1:1:1 co-crystal 1-cyano-2-(4-cyclopropyl-benzyl)-4-(β-D-glucopyranos-1-yl)-benzene-L-proline-water is actually added/used.

In the course of the present invention the term "for, preferably direct, administration to a subject" in connection with "aqueous pharmaceutical composition" means that such aqueous pharmaceutical compositions can be directly administrated to a subject, preferably without further mandatory processing and/or purification steps, and explicitly excludes (mixtures of) organic solvents that are solely mentioned in the context of producing crystalline complexes of SGLT-2 inhibitors. Preferably, such "aqueous pharmaceutical composition" that are "for direct administration to a subject" are therefore sterile and/or comply with GMP manufacturing conditions as well as GCP compliant clinical protocols.

In one aspect, the present invention relates to an aqueous pharmaceutical composition as described and/or claimed herein, wherein the aqueous pharmaceutical composition is for, preferably direct, administration to a subject, preferably without further mandatory processing and/or purification steps, more preferably an animal, even more preferably a mammal, in particular a horse, cat, dog or cow; wherein preferably the aqueous pharmaceutical composition is sterile.

In yet another aspect, the present invention relates to an aqueous pharmaceutical composition as described and/or claimed herein, wherein the at least one SGLT-2 inhibitor is velagliflozin, which preferably is the only SGLT-2 inhibitor contained in such aqueous pharmaceutical composition.

In another aspect, the present invention relates to an aqueous pharmaceutical composition as described and/or claimed herein, wherein the aqueous pharmaceutical composition is a solution, an emulsion or a suspension, preferably a solution, an emulsion or a suspension with an NTU value of equal to or less than 10.0, more preferably equal to or less than 7.0, even more preferably equal to or less than 3.0, and most preferably a solution, in particular a solution with an NTU value of equal to or less than 3.0.

In the course of the present invention the term "NTU" refers to Nephelometric Turbidity Units and to an opalescent value as defined and described in European Pharmacopoeia $8^{th}$ edition (Ph. Eur. 8, Chapter 2.2.1. "Clarity and degree of opalescence of liquids").

In another aspect, the present invention relates to an aqueous pharmaceutical composition as described and/or claimed herein, which contains one or more organic solvents that are independently from each other characterized by a negative $\log_{10}$ P value, preferably a negative decadic logarithmic partition coefficient (P) in an n-octanol/water system according to formula (II):

$$\log_{10} P_{n\text{-}octanol/water} = \text{concentration of unionized compound in n-octanol/concentration of unionized compound in water} \quad \text{(II).}$$

In a further aspect, the present invention relates to an aqueous pharmaceutical composition as described and/or claimed herein, wherein such aqueous pharmaceutical composition as a whole is characterized by a negative Log P-Parameter, preferably a negative Log P-Parameter of equal to or higher than −2.0 (i.e. −2.0≤Log P-Parameter <0). For the avoidance of doubt, the Log P-Parameter is defined as in Eq. 4 of Example 1 and is not identical with and should not be mistaken for the (negative) $\log_{10}$ P value as given for a(n) organic solvent(s).

In yet another aspect, the present invention relates to an aqueous pharmaceutical composition as described and/or claimed herein, wherein the one or more organic solvents are selected from the group consisting of: ethanol ($\log_{10}$ P: −0.16), propane-1,2,3-triol (glycerol; $\log_{10}$ P: −1.84), pyrrolidone ($\log_{10}$ P: −0.58), methylpyrrolidone ($\log_{10}$ P: −0.356), N,N-dimethylacetamide ($\log_{10}$ P: −0.583) and/or N,N-dimethylformamide ($\log_{10}$ P: −0.632). The $\log_{10}$ P values were taken from http://www.chemicalize.org/.

In yet another aspect, the present invention relates to an aqueous pharmaceutical composition as described and/or claimed herein, wherein such aqueous pharmaceutical composition comprises at least two different organic solvents, preferably propane-1,2,3-triol (glycerol) and ethanol.

In yet another aspect, the present invention relates to an aqueous pharmaceutical composition as described and/or claimed herein, wherein such composition contains no more than 20 g/100 mL (20% w/v) of organic solvents, preferably no more than 15 g/100 mL (15% w/v) of organic solvents, more preferably no more than 10 g/100 mL (10% w/v) of organic solvents.

In yet another aspect, the present invention relates to an aqueous pharmaceutical composition as described and/or claimed herein, wherein such composition does not contain propane-1,2-diol (propylene glycol).

In yet another aspect, the present invention relates to an aqueous pharmaceutical composition as described and/or claimed herein, wherein such aqueous pharmaceutical composition comprises ethanol as the only organic solvent contained in such aqueous pharmaceutical composition. Preferably, the ethanol is present in such aqueous pharmaceutical composition at no more than 20 g/100 mL (20% w/v), more preferably at no more than 15 g/100 mL (15% w/v), even more preferably at no more than 10 g/100 mL (10% w/v), most preferably it is present at 8 g/100 mL (8% w/v).

In yet another aspect, the present invention relates to an aqueous pharmaceutical composition as described and/or claimed herein, wherein such composition is substantially free of organic solvents, preferably does not contain any organic solvents. In case no organic solvent is present, the solvent of the aqueous pharmaceutical composition is 100% water, preferably in the form of aqueous buffer.

In yet another aspect, the present invention relates to an aqueous pharmaceutical composition as described and/or claimed herein, wherein such aqueous pharmaceutical composition comprises water in the form of aqueous buffer, such as citric acid buffer, phosphate buffer, ammonium sulphate buffer, ammonium acetate buffer, sodium acetate buffer and the like, preferably aqueous buffer with pH 4.5, more preferably citric acid buffer with pH 4.5.

In yet another aspect, the present invention relates to an aqueous pharmaceutical composition as described and/or claimed herein, wherein such aqueous pharmaceutical composition contains from 30 to 100 g/100 mL (30 to 100% w/v), preferably from 30 to 95 g/100 mL (30 to 95% w/v), more preferably from 30 to 90 g/100 mL (30 to 90% w/v), more preferably from 30 to 85 g/100 mL (30 to 85% w/v), even more preferably from 30 to 80 g/100 mL (30 to 80% w/v), most preferably from 50 to 80 g/100 mL (50 to 80% w/v) water, more preferably in the form of aqueous buffer, such as citric acid buffer, even more preferably aqueous buffer with pH 4.5, most preferably citric acid buffer with pH 4.5.

In yet another aspect, the present invention relates to an aqueous pharmaceutical composition as described and/or claimed herein, wherein such aqueous pharmaceutical composition has a (measured) pH value from 2 to 7, preferably from 3 to 7, more preferably from 3.0 to 6.5, even more preferably from 4.0 to 6.5, even more preferably from 4.0 to 5.0, and most preferably of 4.5. For the avoidance of doubt, the term "measured pH value" refers to the pH value actually measured for the whole aqueous pharmaceutical composition according to the present invention, i.e. comprising both organic solvent(s) phase, if any, and aqueous phase.

In yet another aspect, the present invention relates to an aqueous pharmaceutical composition as described and/or claimed herein, wherein such aqueous pharmaceutical composition additionally comprises one or more preservatives, preferably selected from the group consisting of: sorbic acid or salts thereof, preferably sodium sorbate, potassium sorbate, calcium sorbate; benzoic acid or salts thereof, preferably sodium benzoate; benzalkonium chloride; benzethonium chloride; benzyl alcohol, cetylpyridinium chloride; sodium metabisulfite; sodium acetate; parabens and salts thereof, preferably methylparaben, ethylparaben, propylparaben, butylparaben, butylparaben sodium; most preferably benzoic acid and/or salts thereof, such as sodium benzoate.

In yet another aspect, the present invention relates to an aqueous pharmaceutical composition as described and/or claimed herein, wherein such aqueous pharmaceutical composition additionally comprises one or more antioxidation agents, preferably selected from the group consisting of: ascorbic acid or pharmaceutically acceptable salts thereof, particularly sodium ascorbate; citric acid (anhydrous and/or monohydrate) or pharmaceutically acceptable salts thereof, more preferably sodium citrate; erythorbic acid; fumaric acid; malic acid; monothioglycerol; phosphoric acid; sodium metabisulfite; potassium metabisulfite; propionic acid; sodium bisulfite; sodium sulfite; resveratrol; butylhydroxyanisol; butylhydroxytoluene; gallate derivatives, particularly propylgallate, octylgallate; Vitamin E or pharmaceutically acceptable salts thereof, ascorbyl palmitate; edetic acid or pharmaceutically acceptable salts thereof, most preferably sodium metabisulfite.

In yet another aspect, the present invention relates to an aqueous pharmaceutical composition as described and/or claimed herein, wherein the one or more solubilizing agents are selected from the group consisting of: surfactants, anionic surfactants, non-ionic surfactants, hydrogenated castor oils, polyoxyethylene-polyoxypropylene block copolymers, polyethylene glycols, propylene glycol derivatives, polyvinylpyrrolidones, more preferably selected from the group consisting of: sodium dodecyl sulphate (SDS), Cremophor RH 40 (PEG-40 Hydrogenated Castor Oil, Macrogol glycerol hydroxystearate 40), polysorbate 20, Lutrol F 68 (Poloxamer 188), PEG 200, PEG 300, PEG 400, propylene glycol monolaurate, Kollidon 12 (povidone), wherein preferably the total amount of the one or more solubilizing agents is from 1 to 50 g/100 mL (1-50% w/v), more preferably from 1 to 45 g/100 mL (1-45% w/v), even more preferably from 1 to 40 g/100 mL (1-40% w/v), even more preferably from 1 to 35 g/100 mL (1-35% w/v), even more preferably from 1 to 30 g/100 mL (1-30% w/v), even more preferably from 1 to 25 g/100 mL (1-25% w/v), most preferably from 5 to 25 g/100 mL (5-25% w/v).

In yet another aspect, the present invention relates to an aqueous pharmaceutical composition as described and/or claimed herein, wherein two or more solubilizing agents are contained in the aqueous pharmaceutical composition.

In yet another aspect, the present invention relates to an aqueous pharmaceutical composition as described and/or claimed herein, wherein two solubilizing agents are contained in such aqueous pharmaceutical composition, wherein preferably the amount of the first solubilizing agent and the amount of second solubilizing agent are independently from each other selected from 1 to 50 g/100 mL (1-50% w/v), more preferably from 1 to 45 g/100 mL (1-45% w/v), even more preferably from 1 to 40 g/100 mL (1-40% w/v), even more preferably from 1 to 35 g/100 mL (1-35% w/v), even more preferably from 1 to 30 g/100 mL (1-30% w/v), even more preferably from 1 to 25 g/100 mL (1-25% w/v), most preferably from 5 to 25 g/100 mL (5-25% w/v), wherein more preferably these two solubilizing agents are independently from each other selected from the group consisting of: sodium dodecyl sulphate (SDS), Cremophor RH 40 (PEG-40 Hydrogenated Castor Oil, Macrogol glycerol hydroxystearate 40), polysorbate 20, Lutrol F 68 (Poloxamer 188), PEG 200, PEG 300, PEG 400, propylene glycol monolaurate, Kollidon 12 (povidone), wherein even more preferably, such two solubilizing agents are Kollidon 12 (povidone) as well as PEG 200, PEG 300, or PEG 400, most preferably Kollidon 12 (povidone) and PEG 300.

In yet another aspect, the present invention relates to an aqueous pharmaceutical composition as described and/or claimed herein, wherein such aqueous pharmaceutical composition additionally comprises one or more viscosity-enhancing agents, preferably selected from the group consisting of: inorganic gel forming agents, organic gel forming agents, cellulose derivatives, more preferably selected from the group consisting of: hydroxyl ethyl cellulose, hydroxyl propyl methyl cellulose, silicon dioxide.

In yet another aspect, the present invention relates to an aqueous pharmaceutical composition as described and/or claimed herein, wherein such aqueous pharmaceutical composition additionally comprises one or more flavours and/or sweeteners, preferably selected from the group consisting of: honey flavor, lime/salvia flavor, jasmine flavor, lavender flavor, peppermint flavor, raspberry flavor, lemon flavor, herbs flavor, meat flavor, vanillin/vanilla flavor, saccharine, aspartame, sorbitol, xylitol.

In yet another aspect, the present invention relates to an aqueous pharmaceutical composition as described and/or claimed herein, wherein such aqueous pharmaceutical composition does not comprise any apolar organic solvents, which are preferably and independently from each other characterized by a $\log_{10}$ P value of equal to or higher than 0.

In yet another aspect, the present invention relates to an aqueous pharmaceutical composition as described and/or claimed herein, wherein such aqueous pharmaceutical composition is for oral and/or parenteral administration, preferably oral administration.

In yet another aspect, the present invention relates to an aqueous pharmaceutical composition as described and/or claimed herein, comprising, preferably consisting of:

(i) at least one SGLT-2 inhibitor, preferably velagliflozin, more preferably only one single SGLT-2 inhibitor, even more preferably only velagliflozin as single SGLT-2 inhibitor;

(ii) optionally, but preferred, one or more preservatives; preferably selected from the group consisting of: sorbic acid or salts thereof, preferably sodium sorbate, potassium sorbate, calcium sorbate; benzoic acid or salts thereof, preferably sodium benzoate; benzalkonium chloride; benzethonium chloride; benzyl alcohol, cetylpyridinium chloride; sodium metabisulfite; sodium acetate; parabens and salts thereof, preferably methylparaben, ethylparaben, propylparaben, butylparaben, butylparaben sodium; or combinations thereof; most preferably benzoic acid and/or salts thereof, such as sodium benzoate;

(iii) optionally, one or more organic solvents, preferably selected from the group consisting of: ethanol, propane-1,2,3-triol (glycerol), pyrrolidone, methylpyrrolidone, N,N-dimethylacetamide and/or N,N-dimethylformamide, more preferably ethanol;

(iv) optionally, one or more flavors and/or sweeteners, preferably selected from the group consisting of: honey flavor, lime/salvia flavor, jasmine flavor, lavender flavor, peppermint flavor, raspberry flavor, lemon flavor, herbs flavor, meat flavor, vanillin/vanilla flavor, saccharine, aspartame, sorbitol, xylitol;

(v) water, preferably in the form of aqueous buffer, more preferably citric acid buffer, even more preferably aqueous buffer with pH 4.5, most preferably citric acid buffer with pH 4.5;

(vi) one or more solubilizing agents, preferably selected from the group consisting of: surfactants, anionic surfactants, non-ionic surfactants, hydrogenated castor oils, polyoxyethylene-polyoxypropylene block copolymers, polyethylene glycols, propylene glycol derivatives, polyvinylpyrrolidones, more preferably selected from the group consisting of: sodium dodecyl sulphate (SDS), Cremophor RH 40 (PEG-40 Hydrogenated Castor Oil, Macrogol glycerol hydroxystearate 40), polysorbate 20, Lutrol F 68 (Poloxamer 188), PEG 200, PEG 300, PEG 400, propylene glycol monolaurate, Kollidon 12 (povidone);

(vii) optionally, one or more viscosity-enhancing agents, preferably selected from the group consisting of: inorganic gel forming agents, organic gel forming agents, cellulose derivatives, more preferably selected from the group consisting of: hydroxyl ethyl cellulose, hydroxyl propyl methyl cellulose, silicon dioxide;

(viii) optionally, one or more antioxidation agents, preferably selected from the group consisting of: ascorbic acid or pharmaceutically acceptable salts thereof, particularly sodium ascorbate; citric acid (anhydrous and/or monohydrate) or pharmaceutically acceptable salts thereof, more preferably sodium citrate; erythorbic acid; fumaric acid; malic acid; monothioglycerol; phosphoric acid; sodium metabisulfite; potassium metabisulfite; propionic acid; sodium bisulfite; sodium sulfite; resveratrol; butylhydroxyanisol; butylhydroxytoluene; gallate derivatives, particularly propylgallate, octylgallate; Vitamin E or pharmaceutically acceptable salts thereof; ascorbyl palmitate; edetic acid or pharmaceutically acceptable salts thereof; most preferably sodium metabisulfite.

In yet another aspect, the present invention relates to an aqueous pharmaceutical composition as described and/or claimed herein, comprising, preferably consisting of:

(i) 0.5-20.0 g/100 mL (0.5-20.0% w/v), preferably 0.5-15.0 g/100 mL (0.5-15.0% w/v), more preferably 1.0-1.5 g/100 mL (1.0-1.5% w/v) at least one SGLT-2 inhibitor, preferably velagliflozin, more preferably only one single SGLT-2 inhibitor, even more preferably only velagliflozin as single SGLT-2 inhibitor;

(ii) 0-3.0 g/100 mL (0-3.0% w/v), preferably 0.05-3.0 g/100 mL (0.05-3.0% w/v), more preferably 0.05-2.0 g/100 mL (0.05-2.0% w/v) one or more preservatives; even more preferably selected from the group consisting of: sorbic acid or salts thereof, preferably sodium sorbate, potassium sorbate, calcium sorbate; benzoic acid or salts thereof, preferably sodium benzoate; benzalkonium chloride; benzethonium chloride; benzyl alcohol, cetylpyridinium chloride; sodium metabisulfite; sodium acetate; parabens and salts thereof, preferably methylparaben, ethylparaben, propylparaben, butylparaben, butylparaben sodium; or combinations thereof, most preferably benzoic acid and/or salts thereof, such as sodium benzoate;

(iii) 0-20 g/100 mL (0-20% w/v), preferably 0-15 g/100 mL (0-15% w/v), more preferably 0-12 g/100 mL (0-12% w/v), even more preferably 0-10 g/100 mL (0-10% w/v) one or more organic solvents, preferably selected from the group consisting of: ethanol, propane-1,2,3-triol (glycerol), pyrrolidone, methylpyrrolidone, N,N-dimethylacetamide and/or N,N-dimethylformamide, more preferably ethanol;

(iv) 0-40 g/100 mL (0-40% w/v), preferably 0-30 g/100 mL (0-30% w/v), more preferably 0-2 g/100 mL (0-2% w/v) one or more flavors and/or sweeteners, more preferably selected from the group consisting of: honey flavor, lime/salvia flavor, jasmine flavor, lavender flavor, peppermint flavor, raspberry flavor, lemon flavor, herbs flavor, meat flavor, vanillin/vanilla flavor, saccharine, aspartame, sorbitol, xylitol;

(v) 30 to 100 g/100 mL (30 to 100% w/v), preferably from 30 to 95 g/100 mL (30 to 95% w/v), more preferably from 30 to 90 g/100 mL (30 to 90% w/v), more preferably from 30 to 85 g/100 mL (30 to 85% w/v), even more preferably from 30 to 80 g/100 mL (30 to 80% w/v), most preferably from 50 to 80 g/100 mL (50 to 80% w/v) water, preferably in the form of aqueous buffer, more preferably citric acid buffer, even more preferably aqueous buffer with pH 4.5, most preferably citric acid buffer with pH 4.5;

(vi) 1 to 50 g/100 mL (1-50% w/v), preferably from 1 to 45 g/100 mL (1-45% w/v), even more preferably from 1 to 40 g/100 mL (1-40% w/v), even more preferably from 1 to 35 g/100 mL (1-35% w/v), even more preferably from 1 to 30 g/100 mL (1-30% w/v), even more preferably from 1 to 25 g/100 mL (1-25% w/v), most preferably from 5 to 25 g/100 mL (5-25% w/v) one or more solubilizing agents, preferably selected from the group consisting of: surfactants, anionic surfactants, non-ionic surfactants, hydrogenated castor oils, polyoxyethylene-polyoxypropylene block copolymers, polyethylene glycols, propylene glycol derivatives, polyvinylpyrrolidones, more preferably selected from the group consisting of: sodium dodecyl sulphate (SDS), Cremophor RH 40 (PEG-40 Hydrogenated Castor Oil, Macrogol glycerol hydroxystearate 40), polysorbate 20, Lutrol F 68 (Poloxamer 188), PEG 200, PEG 300, PEG 400, propylene glycol monolaurate, Kollidon 12 (povidone);

(vii) 0-40 g/100 mL (0-40% w/v), preferably 10-30 g/100 mL (10-30% w/v), one or more viscosity-enhancing agents, preferably selected from the group consisting of: inorganic gel forming agents, organic gel forming agents, cellulose derivatives, more preferably selected from the group consisting of: hydroxyl ethyl cellulose, hydroxyl propyl methyl cellulose, silicon dioxide;

(viii) 0-1.0 g/100 mL (0-1.0% w/v), preferably 0-0.5 g/100 mL (0-0.5% w/v), more preferably 0.1-0.3 g/100 mL (0.1-0.3% w/v), one or more antioxidation agents, preferably selected from the group consisting of: ascorbic acid or pharmaceutically acceptable salts thereof, particularly sodium ascorbate; citric acid (anhydrous and/or monohydrate) or pharmaceutically acceptable salts thereof, more preferably sodium citrate; erythorbic acid; fumaric acid; malic acid; monothioglycerol; phosphoric acid; sodium metabisulfite; potassium metabisulfite; propionic acid; sodium bisulfite; sodium sulfite; resveratrol; butylhydroxyanisol; butylhydroxytoluene; gallate derivatives, particularly propylgallate, octylgallate; Vitamin E or pharmaceutically acceptable salts thereof; ascorbyl palmitate; edetic acid or pharmaceutically acceptable salts thereof, most preferably sodium metabisulfite.

In yet another aspect, the present invention relates to an aqueous pharmaceutical composition as described and/or claimed herein, comprising, preferably consisting of: velagliflozin; sodium dodecyl sulphate (SDS), Cremophor RH 40 (PEG-40 Hydrogenated Castor Oil, Macrogol glycerol hydroxystearate 40), polysorbate 20, Lutrol F 68 (Poloxamer 188), PEG 200, PEG 300, PEG 400, propylene glycol monolaurate and/or Kollidon 12 (povidone); sodium benzoate; optionally, Na-metabisulfite; optionally, ethanol; water.

In yet another aspect, the present invention relates to an aqueous pharmaceutical composition as described and/or claimed herein, comprising, preferably consisting of: velagliflozin; citric acid monohydrate; NaOH; sodium dodecyl sulphate (SDS), Cremophor RH 40 (PEG-40 Hydrogenated Castor Oil, Macrogol glycerol hydroxystearate 40), polysorbate 20, Lutrol F 68 (Poloxamer 188), PEG 200, PEG 300, PEG 400, propylene glycol monolaurate and/or Kollidon 12 (povidone); sodium benzoate; optionally, Na-metabisulfite; optionally, ethanol; water.

In yet another aspect, the present invention relates to an aqueous pharmaceutical composition as described and/or claimed herein, comprising, preferably consisting of: velagliflozin; citric acid monohydrate; NaOH; sodium dodecyl sulphate (SDS), Cremophor RH 40 (PEG-40 Hydrogenated Castor Oil, Macrogol glycerol hydroxystearate 40), polysorbate 20, Lutrol F 68 (Poloxamer 188), PEG 200, PEG 300, PEG 400, propylene glycol monolaurate and/or Kollidon 12 (povidone); sodium benzoate; optionally, Na-metabisulfite; optionally, ethanol; sorbitol and/or xylitol; honey flavor and/or vanillin and/or meat flavor; water.

In yet another aspect, the present invention relates to an aqueous pharmaceutical composition as described and/or claimed herein, selected from:

| Ingredient | Composition 1 [mg/mL] | Composition 2 [mg/mL] | Composition 3 [mg/mL] | Composition 4 [mg/mL] |
|---|---|---|---|---|
| Velagliflozin | 15.0 | 15.0 | 15.0 | 15.0 |
| Citric Acid Monohydrate | 10.1 | 9.2 | 9.2 | 9.8 |
| NaOH 1M | 60.0 | 53.6 | 54.4 | 46.4 |
| Kollidon 12 | 75.0 | 75.0 | 75.0 | — |
| PEG 300 | — | — | — | 150.0 |
| Sodium benzoate | 2.0 | 2.0 | 2.0 | 2.0 |
| Na-metabisulfite | 2.0 | 2.0 | 2.0 | — |
| Ethanol, absolut | 80.0 | 80.0 | 80.0 | 80.0 |
| Sorbitol | 170.0 | 170.0 | 170.0 | 170.0 |
| Xylitol | 100.0 | 100.0 | — | 91.8 |
| Honey Flavor | 1.5 | — | — | 1.5 |
| Vanillin | — | 15.0 | — | — |
| Meat Flavor | — | — | 1.0 | — |
| Water, purified | 584.3 | 581.2 | 659.4 | 536.5 |

| Ingredient | Composition 5 [mg/mL] | Composition 6 [mg/mL] | Composition 7 [mg/mL] | Composition 8 [mg/mL] |
|---|---|---|---|---|
| Velagliflozin | 15.0 | 15.0 | 15.0 | 15.0 |
| Citric Acid Monohydrate | 9.8 | 9.8 | 9.8 | 9.8 |
| NaOH 1M | 46.4 | 46.4 | 46.4 | 46.4 |
| Kollidon 12 | — | 100.0 | 50.0 | — |
| PEG 300 | 150.0 | — | 100.0 | — |
| Sodium dodecyl sulphate (SDS; Na-Lauryl-Sulfate) | — | — | — | 50.0 |

-continued

| | | | | |
|---|---|---|---|---|
| Sodium benzoate | 2.0 | 2.0 | 2.0 | 2.0 |
| Na-metabisulfite | — | 2.0 | 2.0 | — |
| Sorbitol | 170.0 | 170.0 | 170.0 | 170.0 |
| Honey Flavor | 1.5 | 1.5 | 1.5 | 1.5 |
| Water, purified | ad. 1100 ml | ad. 1100 ml | ad. 1100 ml | Ad. 1100 ml |

| Ingredient | Composition 9 [mg/mL] | Composition 10 [mg/mL] | Composition 11 [mg/mL] | Composition 12 [mg/mL] |
|---|---|---|---|---|
| Velagliflozin | 15.0 | 15.0 | 15.0 | 15.0 |
| Citric Acid Monohydrate | 9.8 | 9.8 | 9.8 | 9.8 |
| NaOH 1M | 46.4 | 46.4 | 46.4 | 46.4 |
| Cremophor RH40 | 250.0 | — | — | — |
| Polysorbate 80 | — | 250.0 | — | — |
| Poloxamer 188 | — | — | 50.0 | — |
| PEG 400 | — | — | — | 200.0 |
| Sodium benzoate | 2.0 | 2.0 | 2.0 | 2.0 |
| Sorbitol | 170.0 | 170.0 | 170.0 | 170.0 |
| Honey Flavor | 1.5 | 1.5 | 1.5 | 1.5 |
| Water, purified | ad. 1100 ml | ad. 1100 ml | ad. 1100 ml | Ad. 1100 ml |

EXAMPLES

The following examples serve to further illustrate the present invention; but the same should not be construed as a limitation of the scope of the invention disclosed herein.

Example 1

The testing criteria applied are those for evaluation of the clarity of a liquid (formulation) comprising 1-cyano-2-(4-cyclopropyl-benzyl)-4-(β-D-glucopyranos-1-yl)-benzene (velagliflozin) according to Pharm. Eur. 8. Concerning the Ph. Eur. 8, Chapter 2.2.1. "Clarity and degree of opalescence of liquids", a liquid is considered clear if its opalescence is not more pronounced than that of reference suspension I having an opalescent value of 3 NTU (Table 1).

TABLE 1

Measurements of reference suspensions I-IV according Pharm. Eur. 8, Chapter 2.2.1

| Formazin suspensions | Opalescent values (NTU) |
|---|---|
| Reference suspension I | 3 |
| Reference suspension II | 6 |
| Reference suspension III | 18 |
| Reference suspension IV | 30 |
| Standard of opalescence | 60 |
| Primary opalescent suspension | 4000 |

In the following, exemplary pharmaceutical compositions of solvents which were mixed with 1-cyano-2-(4-cyclopropyl-benzyl)-4-(β-D-glucopyranos-1-yl)-benzene (velagliflozin; the substance) according to the present invention are given in detail. The turbidity was measured by using a Hach Lange 2100 N IS apparatus.

In order to quantify the solvent characteristics regarding their suitability to form a physical stable solution with the substance, a Log P-Parameter was introduced (Eq. 4). The Log P-Parameter describes the hydrophilic/hydrophobic nature of solvent mixture containing organic and aqueous solvents and is calculated as follows:

$$Mo_i = \frac{mo_i}{\sum_{i=1}^{n} mo_i} \quad \text{(Eq. 1)}$$

-continued $$\text{Log}Po = \sum_{i=1}^{n} (Mo_i \cdot \text{Log}P_i) \quad \text{(Eq. 2)}$$

$$X_o = 1 - \frac{a_w}{a_{sol}} \quad \text{(Eq. 3)}$$

$$\text{Log}P\ \text{Parameter} = \frac{\text{Log}Po}{X_o} \quad \text{(Eq. 4)}$$

$mo_i$[mol/g]: molecular amount of an organic solvent in the organic phase of a solvent mixture $Mo_i$[−]: molecular fraction of organic solvent $mo_i$ in the organic phase of a solvent mixture Log$P_i$[−]: $\log_{10} P_{n\text{-octanol/water}}$ = concentration of unionized compound in n-octanol/concentration of unionized compound in water of an organic solvent Log$Po$[−]: auxiliary parameter of the organic phase of a solvent mixture $a_w$[g]: mass of water or aqueous buffer in a solvent mixture $a_{sol}$[g]: mass of solvent mixture $X_o$[−]: mass fraction of organic phase in a solvent mixture As described in WO 2017/032799 instability phenomena are expected for Log P-Parameters <−2.0.

Exemplary Calculation

For ethanol the $\log_{10}$ P value (=Log $P_i$) is given as −0.16 and the molecular weight as 46.07 g/mol. The solvent mixture of Composition 1 consists of 80.0 mg/mL ethanol and 644.3 mg/mL $H_2O$ (sum of water purified and aqueous buffer), which corresponds to an organic phase of 11.0% (m/m).

Because ethanol is the only organic solvent, the amount of ethanol in the organic phase is 100% (m/m) or 100 g/100 g which corresponds to 0.0217 mol/g (=$mo_{ethanol}$). Therefore, $Mo_{ethanol}$ is 1 (Eq. 1) and Log Po is calculated as −0.16 (Eq. 2). The mass fraction of the organic phase is 11.0% (m/m) or according to Eq. 3 $X_o$=0.11. Following Eq. 4 a Log P Parameter of −1.45 is calculated for the solvent mixture of Composition 1.

Example 2

In the following Table 2, exemplary pharmaceutical compositions according to the present invention are given in detail (API: active pharmaceutical ingredient).

TABLE 2

| Exemplary pharmaceutical compositions according to the present invention | | |
|---|---|---|
| Ingredient | Concentration [mg/mL] | Function |
| SGLT-2 inhibitor (e.g. velagliflozin) | 5-200; preferably 5-150, more preferably 10-15 | API |
| Kollidon 12 | 1-500, preferably 1-450, more preferably 1-400, even more preferably 1-350, even more preferably 1-300; even more preferably 1-250, most preferably 50-250 | Solubilizer |
| Sodium Benzoate | 0-30; preferably 0.5-30, more preferably 0.5-20 | Preservative |
| Ethanol, abs. | 0-200; preferably 0-150; more preferably 0-120; most preferably 0-100 | Organic Solvent |
| Flavor | 0-30; preferably 0-20 | Flavor |
| Sodium metabisulfite | 0-10; preferably 1-3 | Antioxidant |
| Sweetener (e.g., Sorbitol, Xylitol) | 0-400; preferably 100-300 | Sweetener/ Viscosity Enhancer |
| Aqueous buffer (e.g., citric acid buffer pH 4.5) | 300-1000, 300-950, 300-900, 300-850; 300-800, preferably 500-800 | Water (pH adjusted) |

The production procedure of an exemplary pharmaceutical composition according to the present invention for a single small-scale batch (1000 mL) in form of a general instruction is as follows:

Prepare Buffer Solution

Weigh aqueous buffer solution in a vessel.

Weigh solubilizer components and add to buffer solution under stirring.

Weigh preservative and add to the solution under stirring (if any).

Weigh antioxidant and add to the solution under stirring.

Weigh organic solvent and add to the solution under stirring (if any).

Weigh sweetener and/or viscosity-enhancer and add to the solution under stirring.

Weigh the at least one SGLT-2 inhibitor, preferably velagliflozin, and add in portions to the solution.

Weigh flavor and add to the solution under stirring

Stir until fully dissolved.

Filtration of the solution.

Example 3

Formulation samples were produced with compositions listed in the following Table 3 (API: active pharmaceutical ingredient).

TABLE 3

| Exemplary pharmaceutical compositions according to the present invention | | |
|---|---|---|
| Ingredient | Concentration [mg/mL] | Function |
| SGLT-2 inhibitor (e.g. velagliflozin) | 5-200; preferably 5-150, more preferably 10-15 | API |
| PEG (e.g., PEG200, PEG300, PEG400) | 1-500, preferably 1-450, more preferably 1-400, even more preferably 1-350, even more preferably 1-300; even more preferably 1-250, most preferably 50-250 | Solubilizer |
| Sodium Benzoate | 0-30; preferably 0.5-30, more preferably 0.5-20 | Preservative |
| Ethanol, abs. | 0-200; preferably 0-150; more preferably 0-120; most preferably 0-100 | Organic Solvent |
| Flavor | 0-30; preferably 0-20 | Flavor |
| Sweetener (e.g., Sorbitol, Xylitol) | 0-400; preferably 100-300 | Sweetener/ Viscosity Enhancer |
| Aqueous buffer (e.g., citric acid buffer pH 4.5) | 300-1000, 300-950, 300-900, 300-850; 300-800, preferably 500-800 | Water (pH adjusted) |

The following procedure was used to prepare the samples:

1. Weigh entire amount of aqueous buffer into vessel
2. Weigh entire amount of PEG into a beaker and add slowly to stirred solution.
3. Weigh entire amount of ethanol, abs. into a beaker and add to stirred solution (if any). Stir until fully mixed.
4. Weigh preservative and add to the solution under stirring (if any).
5. Weigh entire amount of the at least one SGLT-2 inhibitor, preferably velagliflozin, into a beaker and add in portions to stirred solution. Stir until fully dissolved.
6. Weigh entire amount of flavour into a beaker and add to stirred solution. Stir until fully dissolved.
7. Weigh entire amount of sweetener and/or viscosity enhancer and add to the solution under stirring.
8. Stir until fully dissolved.
9. Use an 8 μm filter to filtrate the solution Example 4

Formulation samples were produced with compositions listed in the following Table 4.

TABLE 4

| Exemplary pharmaceutical compositions according to the present invention | | | | |
|---|---|---|---|---|
| Ingredient | Composition 1 [mg/mL] | Composition 2 [mg/mL] | Composition 3 [mg/mL] | Composition 4 [mg/mL] |
| Velagliflozin | 15.0 | 15.0 | 15.0 | 15.0 |
| Citric Acid Monohydrate | 10.1 | 9.2 | 9.2 | 9.8 |
| NaOH 1M | 60.0 | 53.6 | 54.4 | 46.4 |

TABLE 4-continued

Exemplary pharmaceutical compositions according to the present invention

| Ingredient | Composition 1 [mg/mL] | Composition 2 [mg/mL] | Composition 3 [mg/mL] | Composition 4 [mg/mL] |
|---|---|---|---|---|
| Kollidon 12 | 75.0 | 75.0 | 75.0 | — |
| PEG 300 | — | — | — | 150.0 |
| Sodium benzoate | 2.0 | 2.0 | 2.0 | 2.0 |
| Na metabisulfite | 2.0 | 2.0 | 2.0 | — |
| Ethanol, absolut | 80.0 | 80.0 | 80.0 | 80.0 |
| Sorbitol | 170.0 | 170.0 | 170.0 | 170.0 |
| Xylitol | 100.0 | 100.0 | — | 91.8 |
| Honey Flavor | 1.5 | — | — | 1.5 |
| Vanillin | — | 15.0 | — | — |
| Meat Flavor | — | — | 1.0 | — |
| Water, purified | 584.3 | 581.2 | 659.4 | 536.5 |

The following procedure was used to prepare the samples:

Weigh entire amount of water into vessel

Weigh entire amounts of NaOH 1N and citric acid monohydrate into a beaker and add to stirred water. Stir until fully dissolved.

Weigh entire amount of solubilizers (Kollidon 12 or PEG 300) into a beaker and add slowly to stirred solution.

Weigh entire amount of ethanol, abs. into a beaker and add to stirred solution. Stir until fully mixed.

Weigh antioxidant (if needed) and preservative and add to the solution under stirring.

Weigh entire amount of sweetener and/or viscosity enhancer and add to the solution under stirring.

Weigh entire amount of flavour into a beaker and add to stirred solution. Stir until fully dissolved.

Weigh entire amount of velagliflozin into a beaker and add in portions to stirred solution.

Stir until fully dissolved.

Use an 8 μm filter to filtrate the solution

The solutions were found to have the following characteristics (Table 5).

TABLE 5

| Formulation/ Solution | LogP-Parameter [—] (Eq. 4) | Turbidity [NTU] | Density* [g/mL] | Appearance |
|---|---|---|---|---|
| Composition 1 | −1.45 | 1.0 | 1.105 | yellowish, clear solution, no particles |
| Composition 2 | −1.43 | 1.4 | 1.108 | yellowish, clear solution, no particles |
| Composition 3 | −1.59 | 1.4 | 1.073 | yellowish, clear solution, no particles |
| Composition 4 | −1.33 | 0.8 | 1.108 | yellowish, clear solution, no particles |

*Density was measured using an Anton Paar DMA38 density meter

Furthermore, the efficacy of antimicrobial preservation of Compositions 1 to 4 was investigated. The testing criteria applied are those for evaluation of antimicrobial activity for oral preparations according to Pharm. Eur. 7 (tests at 14 days and 28 days). The acceptance criteria of the Ph. Eur. 7, Method 5.1.3 "Efficacy of Antimicrobial Preservation", and USP 34, Method <51>"Antimicrobial Effectiveness Testing" are listed in the following Table 6.

TABLE 6

Criteria for evaluation of antimicrobial activity for oral preparations according to Pharm. Eur. 7 and USP 34

| Type of micro-organism | Ph. Eur. 7 Method 5.1.3. Logarithmic reduction of microorganisms after 14 days | 28 days | USP 34 Method <51> 14 days | 28 days |
|---|---|---|---|---|
| Bacteria | >3 | No increase from 14 days [1] | >1.0 | No increase from 14 days [2] |
| Funghi | >1 | No increase from 14 days [1] | No increase from initial calc. count [2] | No increase from initial calc. count [2] |

[1] for Ph. Eur: No increase = no increase in number

[2] for USP: No increase = not more than 0.5 $log_{10}$ units higher than reference value The following microorganisms were tested: *Pseudomonas aeruginosa, Staphylococcus aureus, Escherichia coli, Candida albicans, Aspergillus brasiliensis, Burkholderia cepacia.*

In the performed tests the USP 34 Method <51> Criteria as listed in Table 6 were found to be fulfilled for all solutions for all microorganisms.

Example 5

After sample preparation the solution was filled in polyethylene bottles and closed with polypropylene caps for chemical stability investigations.

For the Compositions 1, 2, 3 and 4 the API content stays constant as 15.0±0.1 mg/mL and no additional degradation ≥1.0% was measured by HPLC analytics after 6 months at 25° C./60% r.h and 40° C./75% r.h. (table 7).

TABLE 7

| | Assay [mg/mL]/degradation [%] measured by HPLC | |
|---|---|---|
| Composition | 6 months at 25° C./60% r.h. | 6 months at 40° C./75% r.h. |
| 1 | 15.1/<1.0% | 15.1/<1.0% |
| 2 | 15.1/<1.0% | 15.1/<1.0% |
| 3 | 15.0/<1.0% | 14.9/<1.0% |
| 4 | 15.1/<1.0% | 15.1/<1.0% |

Example 6

Formulation samples were produced with compositions listed in the following Tables 8 and 9.

TABLE 8

| Exemplary pharmaceutical compositions according to the present invention | | | | |
|---|---|---|---|---|
| Ingredient | Composition 5 [mg/mL] | Composition 6 [mg/mL] | Composition 7 [mg/mL] | Composition 8 [mg/mL] |
| Velagliflozin | 15.0 | 15.0 | 15.0 | 15.0 |
| Citric Acid Monohydrate | 9.8 | 9.8 | 9.8 | 9.8 |
| NaOH 1M | 46.4 | 46.4 | 46.4 | 46.4 |
| Kollidon 12 | — | 100.0 | 50.0 | — |
| PEG 300 | 150.0 | — | 100.0 | — |
| Sodium dodecyl sulphate (SDS; Na-Lauryl-Sulfate) | — | — | — | 50.0 |
| Sodium benzoate | 2.0 | 2.0 | 2.0 | 2.0 |
| Na-metabisulfite | — | 2.0 | 2.0 | — |
| Sorbitol | 170.0 | 170.0 | 170.0 | 170.0 |
| Honey Flavor | 1.5 | 1.5 | 1.5 | 1.5 |
| Water, purified | ad. 1100 ml | ad. 1100 ml | ad. 1100 ml | Ad. 1100 ml |

TABLE 9

| Exemplary pharmaceutical compositions according to the present invention | | | | |
|---|---|---|---|---|
| Ingredient | Composition 9 [mg/mL] | Composition 10 [mg/mL] | Composition 11 [mg/mL] | Composition 12 [mg/mL] |
| Velagliflozin | 15.0 | 15.0 | 15.0 | 15.0 |
| Citric Acid Monohydrate | 9.8 | 9.8 | 9.8 | 9.8 |
| NaOH 1M | 46.4 | 46.4 | 46.4 | 46.4 |
| Cremophor RH40 | 250.0 | — | — | — |
| Polysorbate 80 | — | 250.0 | — | 1 |
| Poloxamer 188 | — | — | 50.0 | — |
| PEG 400 | — | — | — | 200.0 |
| Sodium benzoate | 2.0 | 2.0 | 2.0 | 2.0 |
| Sorbitol | 170.0 | 170.0 | 170.0 | 170.0 |
| Honey Flavor | 1.5 | 1.5 | 1.5 | 1.5 |
| Water, purified | ad. 1100 ml | ad. 1100 ml | ad. 1100 ml | Ad. 1100 ml |

The following procedure was used to prepare the samples:

Weigh approximately 80% of expected amount of water into vessel.

Weigh entire amounts of NaOH 1N and citric acid monohydrate into a beaker and add to stirred water. Stir until fully dissolved.

Weigh entire amount of respective solubilizers (Kollidon 12, PEG 300, Na-Lauryl-Sulfate, Cremophor RH40, Polysorbate 80, Poloxamer 188 and/or PEG 400) into a beaker and add slowly to stirred solution.

Weigh antioxidant (if needed) and preservative and add to the solution under stirring.

Weigh entire amount of sweetener and/or viscosity enhancer and add to the solution under stirring.

Weigh entire amount of flavour into a beaker and add to stirred solution. Stir until fully dissolved.

Weigh entire amount of velagliflozin into a beaker and add in portions to stirred solution.

Stir until fully dissolved.

Fill up to 1100 ml with water.

Stir until a homogeneous, clear solution is reached.

A temperature test (alternating storage between 4° C. and 23° C., over 3 weeks) showed no visual changes for all samples (Table 10).

TABLE 10

| Short-term storage test over 3 weeks with alternating storage at 4° C. and room temperature (23° C.)-visual inspection | |
|---|---|
| | Appearance |
| Composition 5 | Visually no noticeable changes after storage; No precipitation, crystallization or color change recognizable. |

TABLE 10-continued

Short-term storage test over 3 weeks with alternating storage at 4° C. and room temperature (23° C.)-visual inspection

| | Appearance |
|---|---|
| Composition 6 | Visually no noticeable changes after storage; No precipitation, crystallization or color change recognizable. |
| Composition 7 | Visually no noticeable changes after storage; No precipitation, crystallization or color change recognizable. |
| Composition 8 | Visually no noticeable changes after storage; No precipitation, crystallization or color change recognizable. |
| Composition 9 | Visually no noticeable changes after storage; No precipitation, crystallization or color change recognizable. |
| Composition 10 | Visually no noticeable changes after storage; No precipitation, crystallization or color change recognizable. |
| Composition 11 | Visually no noticeable changes after storage; No precipitation, crystallization or color change recognizable. |
| Composition 12 | Visually no noticeable changes after storage; No precipitation, crystallization or color change recognizable. |

REFERENCES (1) EP 1 609 785
(2) European Pharmacopoeia 7th edition, Method 5.1.3
(3) European Pharmacopoeia 8th edition, Chapter 2.2.1
(4) United States Pharmacopeia (USP) 34, Method <51>
(5) US 2011/077213
(6) US 2014/031540
(7) US 2017/145000
(8) US 2020/237794
(9) US 2022/016078
(10) WO 2006/064033
(11) WO 2007/028814
(12) WO 2007/080170
(13) WO 2007/093610
(14) WO 2007/128749
(15) WO 2013/079501
(16) WO 2014/016381
(17) WO 2014/195966
(18) WO 2015/110402
(19) WO 2015/173584
(20) WO 2017/032799
(21) WO 2020/219645
(22) WO 2021/105152
(23) WO 2021/165177
(24) WO 2023/006718
(25) WO 2023/006745
(26) WO 2023/006747
(27) Xu G et al., Journal of Medical Chemistry 2014, 57: 1236-1251

The following clauses are also part of the disclosure and are comprised by the spirit and scope of the present invention:

1. An aqueous pharmaceutical composition comprising at least one SGLT-2 inhibitor and one or more solubilizing agents.

2. The aqueous pharmaceutical composition according to clause 1, wherein the at least one SGLT-2 inhibitor is selected from the group consisting of:

(1) a glucopyranosyl-substituted benzene derivative of the formula (1)

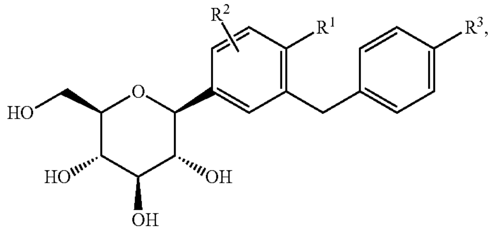

wherein $R^1$ denotes cyano, Cl or methyl (most preferably cyano);

$R^2$ denotes H, methyl, methoxy or hydroxy (most preferably H) and $R^3$ denotes cyclopropyl, hydrogen, fluorine, chlorine, bromine, iodine, methyl, ethyl, propyl, isopropyl, butyl, sec-butyl, iso-butyl, tert-butyl, 3-methyl-but-1-yl, cyclobutyl, cyclopentyl, cyclohexyl, 1-hydroxy-cyclopropyl, 1-hydroxy-cyclobutyl, 1-hydroxy-cyclopentyl, 1-hydroxy-cyclohexyl, ethinyl, ethoxy, difluoromethyl, trifluoromethyl, pentafluoroethyl, 2-hydroxyl-ethyl, hydroxymethyl, 3-hydroxypropyl, 2-hydroxy-2-methyl-prop-1-yl, 3-hydroxy-3-methyl-but-1-yl, 1-hydroxy-1-methyl-ethyl, 2,2,2-trifluoro-1-hydroxy-1-methyl-ethyl, 2,2,2-trifluoro-1-hydroxy-1-trifluoromethyl-ethyl, 2-methoxyethyl, 2-ethoxy-ethyl, hydroxy, difluoromethyloxy, trifluoromethyloxy, 2-methyloxy-ethyloxy, methylsulfanyl, methylsulfinyl, methlysulfonyl, ethylsulfinyl, ethylsulfonyl, trimethylsilyl, (R)-tetrahydrofuran-3-yloxy or (S)-tetrahydrofuran-3-yloxy or cyano;

wherein $R^3$ is preferably selected from cyclopropyl, ethyl, ethinyl, ethoxy, (R)-tetrahydrofuran-3-yloxy or (S)-tetrahydrofuran-3-yloxy; and most preferably $R^3$ is cyclopropyl, or a derivative thereof wherein one or more hydroxyl groups of the 3-D-glucopyranosyl group are acylated with groups selected from ($C_{1-18}$-alkyl)carbonyl, ($C_{1-18}$-alkyl)oxycarbonyl, phenylcarbonyl and phenyl-($C_{1-3}$-alkyl)-carbonyl;

(2) Velagliflozin, represented by formula (2):

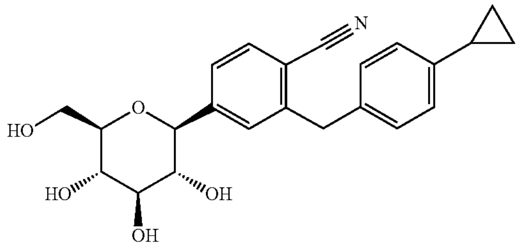 [SMILES: N#Cc1ccc([C@@H]2O[C@H](CO)[C@@H](O)[C@H](O)[C@H]2O)cc1Cc1ccc(C2CC2)cc1]

(3) Dapagliflozin, represented by formula (3):

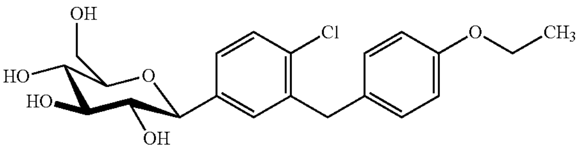

(4) Canagliflozin, represented by formula (4):
lp;3p
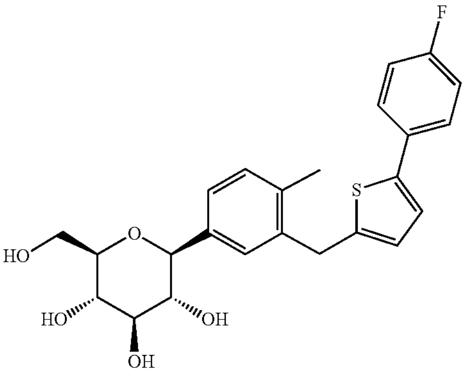 [SMILES: Cc1ccc([C@@H]2O[C@H](CO)[C@@H](O)[C@H](O)[C@H]2O)cc1Cc1ccc(-c2ccc(F)cc2)s1]
(5) Empagliflozin, represented by formula (5):
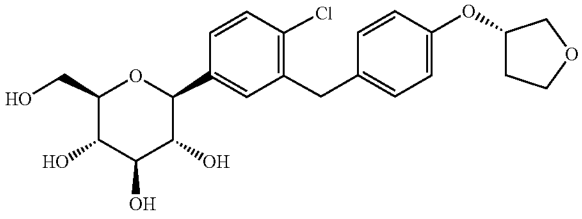 [SMILES: OC[C@H]1O[C@@H](c2ccc(Cl)c(Cc3ccc(O[C@H]4CCOC4)cc3)c2)[C@H](O)[C@@H](O)[C@@H]1O]
(6) Luseogliflozin, represented by formula (6):
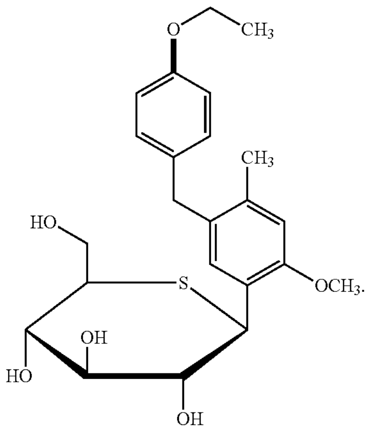
(7) Tofogliflozin, represented by formula (7):
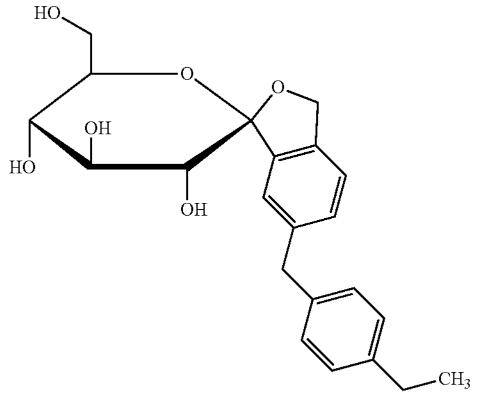
(8) Ipragliflozin, represented by formula (8):
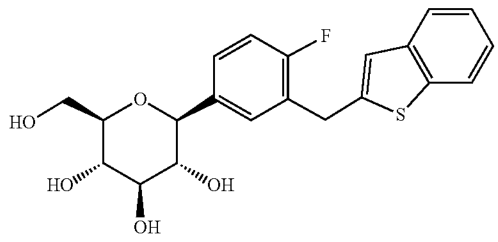 [SMILES: OC[C@H]1O[C@@H](c2ccc(F)c(Cc3cc4ccccc4s3)c2)[C@H](O)[C@@H](O)[C@@H]1O]
(9) Ertugliflozin, represented by formula (9):
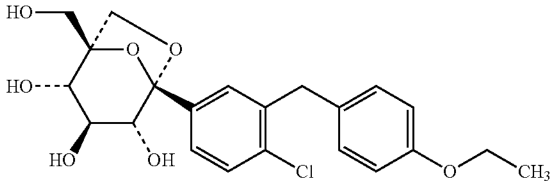 [SMILES: CCOc1ccc(Cc2cc([C@]34OC[C@](CO)(O3)[C@@H](O)[C@H](O)[C@H]4O)ccc2Cl)cc1]
(10) Atigliflozin, represented by formula (10):
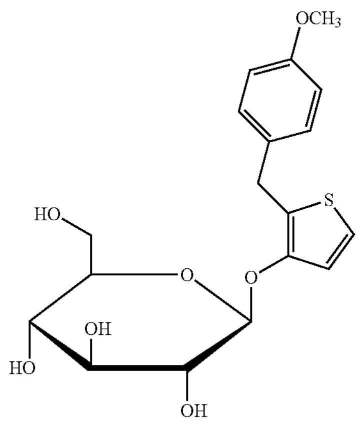

(11) Remogliflozin, represented by formula (11):

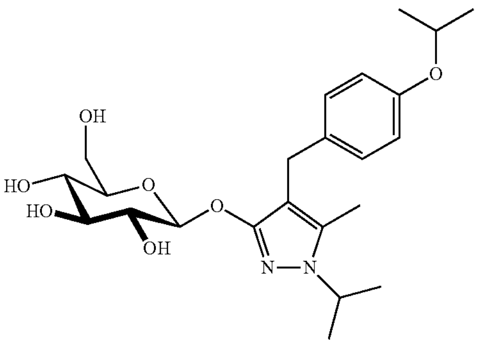

(11A) Remogliflozin etabonate, represented by formula (11A):

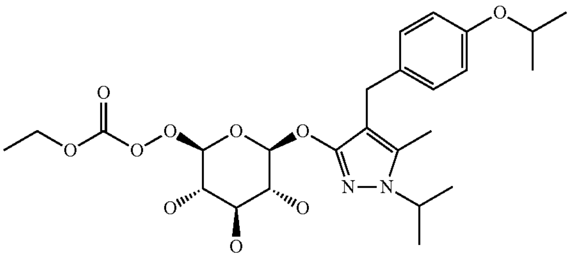 [SMILES: CCOC(=O)OO[C@H]1O[C@@H](Oc2nn(C(C)C)c(C)c2Cc2ccc(OC(C)C)cc2)[C@H](O)[C@@H](O)[C@@H]1O]

(12) a thiophene derivative of the formula (12)

(7-1)

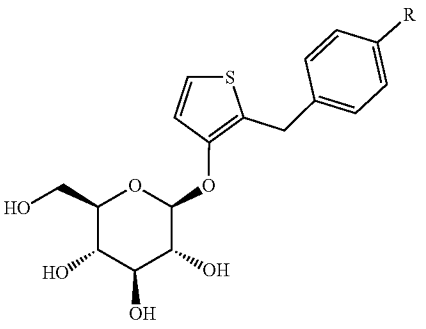

wherein R denotes methoxy or trifluoromethoxy;

(13) 1-(β-D-glucopyranosyl)-4-methyl-3-[5-(4-fluoro-phenyl)-2-thienylmethyl]benzene, represented by formula (13);

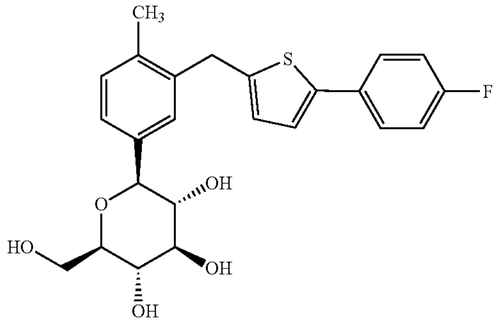 [SMILES: Cc1ccc([C@@H]2O[C@H](CO)[C@@H](O)[C@H](O)[C@H]2O)cc1Cc1ccc(-c2ccc(F)cc2)s1]

(14) a spiroketal derivative of the formula (14):

(9-1)

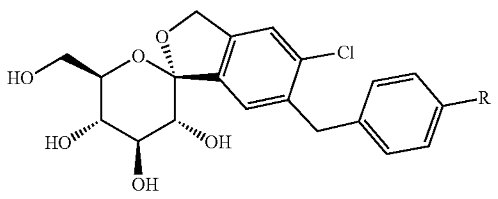

wherein R denotes methoxy, trifluoromethoxy, ethoxy, ethyl, isopropyl or tert. butyl;

(15) a pyrazole-O-glucoside derivative of the formula (15)

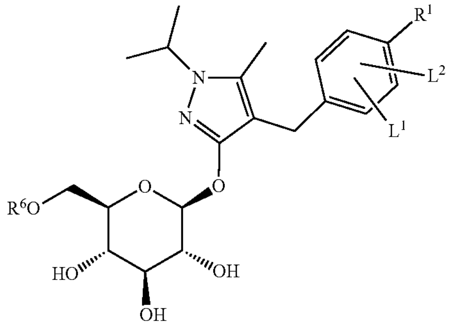

wherein $R^1$ denotes $C_{1-3}$-alkoxy, $L^1$, $L^2$ independently of each other denote H or F, $R^6$ denotes H, ($C_{1-3}$-alkyl)carbonyl, ($C_{1-6}$-alkyl)oxy-carbonyl, phenyloxycarbonyl, benzyloxycarbonyl or benzylcarbonyl;

(16) Sotagliflozin, represented by formula (16):

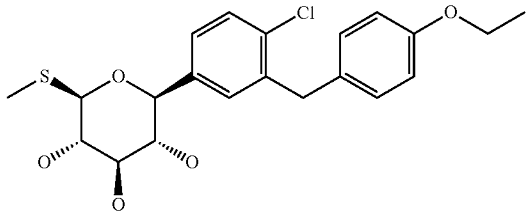 [SMILES: CCOc1ccc(Cc2cc([C@@H]3O[C@H](SC)[C@@H](O)[C@H](O)[C@H]3O)ccc2Cl)cc1]

(17) Sergliflozin, represented by formula (17):

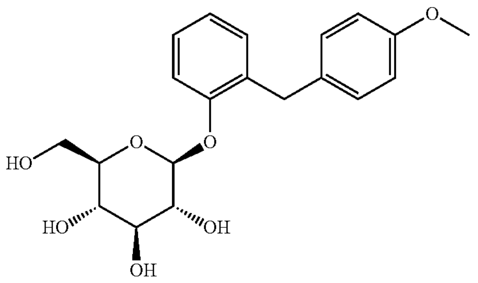 [SMILES: COc1ccc(Cc2ccccc2O[C@@H]2O[C@H](CO)[C@@H](O)[C@H](O)[C@H]2O)cc1]

(18) a compound represented by formula (18):

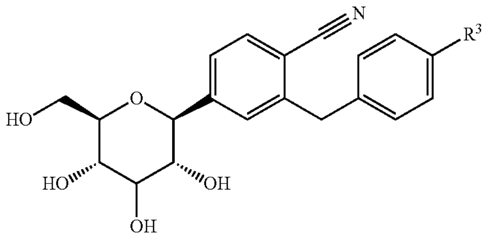

wherein $R^3$ denotes cyclopropyl, hydrogen, fluorine, chlorine, bromine, iodine, methyl, ethyl, propyl, isopropyl, butyl, sec-butyl, iso-butyl, tert-butyl, 3-methyl-but-1-yl, cyclobutyl, cyclopentyl, cyclohexyl, 1-hydroxy-cyclopropyl, 1-hydroxy-cyclobutyl, 1-hydroxy-cyclopentyl, 1-hydroxy-cyclohexyl, ethinyl, ethoxy, difluoromethyl, trifluoromethyl, pentafluoroethyl, 2-hydroxyl-ethyl, hydroxymethyl, 3-hydroxy-propyl, 2-hydroxy-2-methyl-prop-1-yl, 3-hydroxy-3-methyl-but-1-yl, 1-hydroxy-1-methyl-ethyl, 2,2,2-trifluoro-1-hydroxy-1-methyl-ethyl, 2,2,2-trifluoro-1-hydroxy-1-trifluoromethyl-ethyl, 2-methoxy-ethyl, 2-ethoxy-ethyl, hydroxy, difluoromethyloxy, trifluoromethyloxy, 2-methyloxy-ethyloxy, methylsulfanyl, methylsulfinyl, methlysulfonyl, ethylsulfinyl, ethylsulfonyl, trimethylsilyl, (R)-tetrahydrofuran-3-yloxy or (S)-tetrahydrofuran-3-yloxy or cyano, and wherein $R^3$ is preferably selected from cyclopropyl, ethyl, ethinyl, ethoxy, (R)-tetrahydrofuran-3-yloxy or (S)-tetrahydrofuran-3-yloxy; and $R^3$ most preferably is cyclopropyl, or a derivative thereof wherein one or more hydroxyl groups of the β-D-glucopyranosyl group are acylated with groups selected from ($C_{1-18}$-alkyl)carbonyl, ($C_{1-18}$-alkyl)oxycarbonyl, phenylcarbonyl and phenyl-($C_{1-3}$-alkyl)-carbonyl;

(19) Bexagliflozin, represented by formula (19):

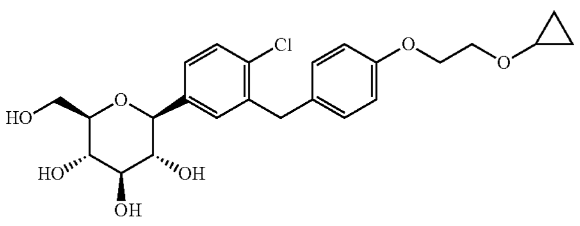 [SMILES: OC[C@H]1O[C@@H](c2ccc(Cl)c(Cc3ccc(OCCOC4CC4)cc3)c2)[C@H](O)[C@@H](O)[C@@H]1O]

(20) Janagliflozin, represented by formula (20):

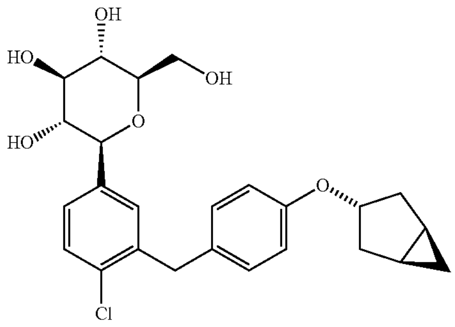

(21) Rongliflozin,

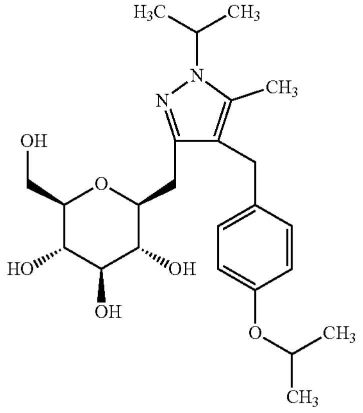 [SMILES: Cc1c(Cc2ccc(OC(C)C)cc2)c(C[C@@H]2O[C@H](CO)[C@@H](O)[C@H](O)[C@H]2O)nn1C(C)C]

(22) Wanpagliflozin.

3. The aqueous pharmaceutical composition according to any one of clauses 1 to 2, wherein the at least one SGLT-2 inhibitor is velagliflozin, which preferably is the only SGLT-2 inhibitor contained in such aqueous pharmaceutical composition, and/or wherein the aqueous pharmaceutical composition is for administration to a subject, preferably an animal, more preferably a mammal, in particular a horse, cat, dog or cow; wherein preferably the aqueous pharmaceutical composition is sterile.

4. The aqueous pharmaceutical composition according to any one of clauses 1 to 3, wherein such composition is substantially free of organic solvents, preferably does not contain any organic solvents.

5. The aqueous pharmaceutical composition according to any one of clauses 1 to 3, wherein such composition contains no more than 20 g/100 mL (20% w/v) of organic solvents, preferably no more than 15 g/100 mL (15% w/v) of organic solvents, more preferably no more than 10 g/100 mL (10% w/v) of organic solvents, wherein preferably the organic solvents comprise ethanol, wherein more preferably ethanol is the only organic solvent contained in such aqueous pharmaceutical composition.

6. The aqueous pharmaceutical composition according to clause 5, wherein such composition does not contain propane-1,2-diol (propylene glycol).

7. The aqueous pharmaceutical composition according to any one of clauses 1 to 6, wherein the one or more solubilizing agents are selected from the group consisting of: "surfactants, anionic surfactants, non-ionic surfactants, hydrogenated castor oils, polyoxyethylene-polyoxypropylene block copolymers, polyethylene glycols, propylene glycol derivatives, polyvinylpyrrolidones", preferably selected from the group consisting of: "Sodium dodecyl sulphate (SDS), Cremophor RH 40 (PEG-40 Hydrogenated Castor Oil, Macrogol glycerol hydroxystearate 40), polysorbate 20, Lutrol F 68 (Poloxamer 188), PEG 200, PEG 300, PEG 400, propylene glycol monolaurate, Kollidon 12 (povidone)", wherein preferably the total amount of the one or more solubilizing agents is from 1 to 50 g/100 mL (1-50% w/v), more preferably from 1 to 45 g/100 mL (1-45% w/v), even more preferably from 1 to 40 g/100 mL (1-40% w/v), even more preferably from 1 to 35 g/100 mL (1-35% w/v), even more preferably from 1 to 30 g/100 mL (1-30% w/v), even more preferably from 1 to 25 g/100 mL (1-25% w/v), most preferably from 5 to 25 g/100 mL (5-25% w/v).

8. The aqueous pharmaceutical composition according to any one of clauses 1 to 6, wherein two or more solubilizing agents are contained in the aqueous pharmaceutical composition.

9. The aqueous pharmaceutical composition according to clause 8, wherein two solubilizing agents are contained in such aqueous pharmaceutical composition, wherein preferably the amount of the first solubilizing agent and the amount of the second solubilizing agent are independently from each other selected from 1 to 50 g/100 mL (1-50% w/v), more preferably from 1 to 45 g/100 mL (1-45% w/v), even more preferably from 1 to 40 g/100 mL (1-40% w/v), even more preferably from 1 to 35 g/100 mL (1-35% w/v), even more preferably from 1 to 30 g/100 mL (1-30% w/v), even more preferably from 1 to 25 g/100 mL (1-25% w/v), most preferably from 5 to 25 g/100 mL (5-25% w/v), wherein more preferably these two solubilizing agents are independently from each other selected from the group consisting of: "sodium dodecyl sulphate (SDS), Cremophor RH 40 (PEG-40 Hydrogenated Castor Oil, Macrogol glycerol hydroxystearate 40), polysorbate 20, Lutrol F 68 (Poloxamer 188), PEG 200, PEG 300, PEG 400, propylene glycol monolaurate, Kollidon 12 (povidone)", wherein even more preferably, such two solubilizing agents are Kollidon 12 (povidone) as well as PEG 200, PEG 300, or PEG 400, most preferably Kollidon 12 (povidone) and PEG 300.

10. The aqueous pharmaceutical composition according to any one of clauses 1 to 9, wherein the aqueous pharmaceutical composition is a solution, an emulsion or a suspension, preferably a solution, an emulsion or a suspension with an NTU value of equal to or less than 10.0, more preferably equal to or less than 7.0, even more preferably equal to or less than 3.0, and most preferably a solution, in particular a solution with an NTU value of equal to or less than 3.0.

11. The aqueous pharmaceutical composition according to any one of clauses 1 to 10, wherein such aqueous pharmaceutical composition contains from 30 to 100 g/100 mL (30 to 100% w/v), preferably from 30 to 95 g/100 mL (30 to 95% w/v), more preferably from 30 to 90 g/100 mL (30 to 90% w/v), more preferably from 30 to 85 g/100 mL (30 to 85% w/v), even more preferably from 30 to 80 g/100 mL (30 to 80% w/v), most preferably from 50 to 80 g/100 mL (50 to 80% w/v) water, more preferably in the form of aqueous buffer, such as citric acid buffer.

12. The aqueous pharmaceutical composition according to clause 11, wherein such aqueous pharmaceutical composition has a measured pH value of from 2 to 7, preferably from 3 to 7, more preferably from 3.0 to 6.5, even more preferably from 4.0 to 6.5, even more preferably from 4.0 to 5.0, and most preferably of 4.5.

13. The aqueous pharmaceutical composition according to any one of clauses 1 to 12, wherein such aqueous pharmaceutical composition additionally comprises one or more preservatives, preferably selected from the group consisting of: sorbic acid or salts thereof, more preferably sodium sorbate, potassium sorbate, calcium sorbate; benzoic acid or salts thereof, more preferably sodium benzoate; benzalkonium chloride; benzethonium chloride; benzyl alcohol, cetylpyridinium chloride; sodium metabisulfite; sodium acetate; parabenes and salts thereof, more preferably methylparabene, ethylparabene, propylparabene, butylparabene, butylparabene sodium; most preferably benzoic acid and/or salts thereof, such as sodium benzoate; and/or additionally comprises one or more antioxidation agents, preferably selected from the group consisting of: ascorbic acid or pharmaceutically acceptable salts thereof, particularly sodium ascorbate; citric acid (anhydrous and/or monohydrate) or pharmaceutically acceptable salts thereof, more preferably sodium citrate; erythorbic acid; fumaric acid; malic acid; monothioglycerol; phosphoric acid; sodium metabisulfite; potassium metabisulfite; propionic acid; sodium bisulfite; sodium sulfite; resveratrol; butylhydroxyanisol; butylhydroxytoluene; gallate derivatives, particularly propylgallate, octylgallate; Vitamin E or pharmaceutically acceptable salts thereof; ascorbyl palmitate; edetic acid or pharmaceutically acceptable salts thereof; most preferably sodium metabisulfite; and/or additionally comprises one or more viscosity-enhancing agents, preferably selected from the group consisting of: "inorganic gel forming agents, organic gel forming agents, cellulose derivatives", more preferably selected from the group consisting of: "hydroxyl ethyl cellulose, hydroxyl propyl methyl cellulose, silicon dioxide"; and/or additionally comprises one or more flavours and/or sweeteners, preferably selected from the group consisting of: "honey flavor, lime/salvia flavor, jasmine flavor, lavender flavor, peppermint flavor, raspberry flavor, lemon flavor, herbs flavor, meat flavor, vanillin/vanilla flavor, saccharine, aspartame, sorbitol, xylitol".

14. The aqueous pharmaceutical composition according to any one of clauses 1 to 13 comprising, preferably consisting of:

(i) at least one SGLT-2 inhibitor, preferably velagliflozin, more preferably only one single SGLT-2 inhibitor, even more preferably only velagliflozin as single SGLT-2 inhibitor;

(ii) optionally, but preferred, one or more preservatives; preferably selected from the group consisting of: sorbic acid or salts thereof, preferably sodium sorbate, potassium sorbate, calcium sorbate; benzoic acid or salts thereof, preferably sodium benzoate; benzalkonium chloride; benzethonium chloride; benzyl alcohol, cetylpyridinium chloride; sodium metabisulfite; sodium acetate; parabenes and salts thereof, preferably methylparabene, ethylparabene, propylparabene, butylparabene, butylparabene sodium; or combinations thereof; most preferably benzoic acid and/or salts thereof, such as sodium benzoate;

(iii) optionally, one or more organic solvents, preferably selected from the group consisting of: "ethanol, propane-1,2,3-triol (glycerol), pyrrolidone, methylpyrrolidone, N,N-dimethylacetamide and/or N,N-dimethylformamide", more preferably ethanol;

(iv) optionally, one or more flavors and/or sweeteners, preferably selected from the group consisting of: "honey flavor, lime/salvia flavor, jasmine flavor, lavender flavor, peppermint flavor, raspberry flavor, lemon flavor, herbs flavor, meat flavor, vanillin/vanilla flavor, saccharine, aspartame, sorbitol, xylitol";

(v) water, preferably in the form of aqueous buffer, more preferably citric acid buffer, even more preferably aqueous buffer with pH 4.5, most preferably citric acid buffer with pH 4.5;

(vi) one or more solubilizing agents, preferably selected from the group consisting of: "surfactants, anionic surfactants, non-ionic surfactants, hydrogenated castor oils, polyoxyethylene-polyoxypropylene block copolymers, polyethylene glycols, propylene glycol derivatives, polyvinylpyrrolidones", more preferably selected from the group consisting of: "sodium dodecyl sulphate (SDS), Cremophor RH 40 (PEG-40 Hydrogenated Castor Oil, Macrogol glycerol hydroxystearate 40), polysorbate 20, Lutrol F 68 (Poloxamer 188), PEG 200, PEG 300, PEG 400, propylene glycol monolaurate, Kollidon 12 (povidone)";

(vii) optionally, one or more viscosity-enhancing agents, preferably selected from the group consisting of: "inorganic gel forming agents, organic gel forming agents, cellulose derivatives", more preferably selected from the group consisting of: "hydroxyl ethyl cellulose, hydroxyl propyl methyl cellulose, silicon dioxide";

(viii) optionally, one or more antioxidation agents, preferably selected from the group consisting of: ascorbic acid or pharmaceutically acceptable salts thereof, particularly sodium ascorbate; citric acid (anhydrous and/or monohydrate) or pharmaceutically acceptable salts thereof, more preferably sodium citrate; erythorbic acid; fumaric acid; malic acid; monothioglycerol; phosphoric acid; sodium metabisulfite; potassium metabisulfite; propionic acid; sodium bisulfite; sodium sulfite; resveratrol; butylhydroxyanisol; butylhydroxytoluene; gallate derivatives, particularly propylgallate, octylgallate; Vitamin E or pharmaceutically acceptable salts thereof; ascorbyl palmitate; edetic acid or pharmaceutically acceptable salts thereof, most preferably sodium metabisulfite.

15. The aqueous pharmaceutical composition according to any one of clauses 1 to 14 comprising, preferably consisting of:

(i) 0.5-20.0 g/100 mL (0.5-20.0% w/v), preferably 0.5-15.0 g/100 mL (0.5-15.0% w/v), more preferably 1.0-1.5 g/100 mL (1.0-1.5% w/v) at least one SGLT-2 inhibitor, preferably velagliflozin, more preferably only one single SGLT-2 inhibitor, even more preferably only velagliflozin as single SGLT-2 inhibitor;

(ii) 0-3.0 g/100 mL (0-3.0% w/v), preferably 0.05-3.0 g/100 mL (0.05-3.0% w/v), more preferably 0.05-2.0 g/100 mL (0.05-2.0% w/v) one or more preservatives; more preferably selected from the group consisting of: sorbic acid or salts thereof, preferably sodium sorbate, potassium sorbate, calcium sorbate; benzoic acid or salts thereof, preferably sodium benzoate; benzalkonium chloride; benzethonium chloride; benzyl alcohol, cetylpyridinium chloride; sodium metabisulfite; sodium acetate; parabenes and salts thereof, preferably methylparabene, ethylparabene, propylparabene, butylparabene, butylparabene sodium; or combinations thereof, most preferably benzoic acid and/or salts thereof, such as sodium benzoate;

(iii) 0-20 g/100 mL (0-20% w/v), preferably 0-15 g/100 mL (0-15% w/v), more preferably 0-12 g/100 mL (0-12% w/v), even more preferably 0-10 g/100 mL (0-10% w/v) one or more organic solvents, preferably selected from the group consisting of: "ethanol, propane-1,2,3-triol (glycerol), pyrrolidone, methylpyrrolidone, N,N-dimethylacetamide and/or N,N-dimethylformamide", more preferably ethanol;

(iv) 0-40 g/100 mL (0-40% w/v), preferably 0-30 g/100 mL (0-30% w/v), more preferably 0-2 g/100 mL (0-2% w/v) one or more flavors and/or sweeteners, more preferably selected from the group consisting of: "honey flavor, lime/salvia flavor, jasmine flavor, lavender flavor, peppermint flavor, raspberry flavor, lemon flavor, herbs flavor, meat flavor, vanillin/vanilla flavor, saccharine, aspartame, sorbitol, xylitol";

(v) 30 to 100 g/100 mL (30 to 100% w/v), preferably from 30 to 95 g/100 mL (30 to 95% w/v), more preferably from 30 to 90 g/100 mL (30 to 90% w/v), more preferably from 30 to 85 g/100 mL (30 to 85% w/v), even more preferably from 30 to 80 g/100 mL (30 to 80% w/v), most preferably from 50 to 80 g/100 mL (50 to 80% w/v) water, preferably in the form of aqueous buffer, more preferably citric acid buffer, even more preferably aqueous buffer with pH 4.5, most preferably citric acid buffer with pH 4.5;

(vi) 1 to 50 g/100 mL (1-50% w/v), preferably from 1 to 45 g/100 mL (1-45% w/v), even more preferably from 1 to 40 g/100 mL (1-40% w/v), even more preferably from 1 to 35 g/100 mL (1-35% w/v), even more preferably from 1 to 30 g/100 mL (1-30% w/v), even more preferably from 1 to 25 g/100 mL (1-25% w/v), most preferably from 5 to 25 g/100 mL (5-25% w/v) one or more solubilizing agents, preferably selected from the group consisting of: "surfactants, anionic surfactants, non-ionic surfactants, hydrogenated castor oils, polyoxyethylene-polyoxypropylene block copolymers, polyethylene glycols, propylene glycol derivatives, polyvinylpyrrolidones", more preferably selected from the group consisting of: "sodium dodecyl sulphate (SDS), Cremophor RH 40 (PEG-40 Hydrogenated Castor Oil, Macrogol glycerol hydroxystearate 40), polysorbate 20, Lutrol F 68 (Poloxamer 188), PEG 200, PEG 300, PEG 400, propylene glycol monolaurate, Kollidon 12 (povidone)";

(vii) 0-40 g/100 mL (0-40% w/v), preferably 10-30 g/100 mL (10-30% w/v) one or more viscosity-enhancing agents, preferably selected from the group consisting of: "inorganic gel forming agents, organic gel forming agents, cellulose derivatives", more preferably selected from the group consisting of: "hydroxyl ethyl cellulose, hydroxyl propyl methyl cellulose, silicon dioxide";

(viii) 0-1.0 g/100 mL (0-1.0% w/v), preferably 0-0.5 g/100 mL (0-0.5% w/v), more preferably 0.1-0.3 g/100 mL (0.1-0.3% w/v) one or more antioxidation agents, preferably selected from the group consisting of: ascorbic acid or pharmaceutically acceptable salts thereof, particularly sodium ascorbate; citric acid (anhydrous and/or monohydrate) or pharmaceutically acceptable salts thereof, more preferably sodium citrate; erythorbic acid; fumaric acid; malic acid; monothioglycerol; phosphoric acid; sodium metabisulfite; potassium metabisulfite; propionic acid; sodium bisulfite; sodium sulfite; resveratrol; butylhydroxyanisol; butylhydroxytoluene; gallate derivatives, particularly propylgallate, octylgallate; Vitamin E or pharmaceutically acceptable salts thereof; ascorbyl palmitate; edetic acid or pharmaceutically acceptable salts thereof, most preferably sodium metabisulfite.

16. The aqueous pharmaceutical composition according to any one of clauses 1 to 15 comprising: velagliflozin; sodium dodecyl sulphate (SDS), Cremophor RH 40 (PEG- 40 Hydrogenated Castor Oil, Macrogol glycerol hydroxystearate 40), polysorbate 20, Lutrol F 68 (Poloxamer 188), PEG 200, PEG 300, PEG 400, propylene glycol monolaurate and/or Kollidon 12 (povidone); sodium benzoate; optionally, Na-metabisulfite; optionally, ethanol; water.

17. The aqueous pharmaceutical composition according to any one of clauses 1 to 16 selected from the group consisting of the following compositions 1 to 12:

| Ingredient | Composition 1 [mg/mL] | Composition 2 [mg/mL] | Composition 3 [mg/mL] | Composition 4 [mg/mL] |
|---|---|---|---|---|
| Velagliflozin | 15.0 | 15.0 | 15.0 | 15.0 |
| Citric Acid Monohydrate | 10.1 | 9.2 | 9.2 | 9.8 |
| NaOH 1M | 60.0 | 53.6 | 54.4 | 46.4 |
| Kollidon 12 | 75.0 | 75.0 | 75.0 | — |
| PEG 300 | — | — | — | 150.0 |
| Sodium benzoate | 2.0 | 2.0 | 2.0 | 2.0 |
| Na metabisulfite | 2.0 | 2.0 | 2.0 | — |
| Ethanol, absolut | 80.0 | 80.0 | 80.0 | 80.0 |
| Sorbitol | 170.0 | 170.0 | 170.0 | 170.0 |
| Xylitol | 100.0 | 100.0 | — | 91.8 |
| Honey Flavor | 1.5 | — | — | 1.5 |
| Vanillin | — | 15.0 | — | — |
| Meat Flavor | — | — | 1.0 | — |
| Water, purified | 584.3 | 581.2 | 659.4 | 536.5 |

| Ingredient | Composition 5 [mg/mL] | Composition 6 [mg/mL] | Composition 7 [mg/mL] | Composition 8 [mg/mL] |
|---|---|---|---|---|
| Velagliflozin | 15.0 | 15.0 | 15.0 | 15.0 |
| Citric Acid Monohydrate | 9.8 | 9.8 | 9.8 | 9.8 |
| NaOH 1M | 46.4 | 46.4 | 46.4 | 46.4 |
| Kollidon 12 | — | 100.0 | 50.0 | — |
| PEG 300 | 150.0 | — | 100.0 | — |
| Sodium dodecyl sulphate (SDS; Na-Lauryl-Sulfate) | — | — | — | 50.0 |
| Sodium benzoate | 2.0 | 2.0 | 2.0 | 2.0 |
| Na-metabisulfite | — | 2.0 | 2.0 | — |
| Sorbitol | 170.0 | 170.0 | 170.0 | 170.0 |
| Honey Flavor | 1.5 | 1.5 | 1.5 | 1.5 |
| Water, purified | ad. 1100 ml | ad. 1100 ml | ad. 1100 ml | Ad. 1100 ml |

| Ingredient | Composition 9 [mg/mL] | Composition 10 [mg/mL] | Composition 11 [mg/mL] | Composition 12 [mg/mL] |
|---|---|---|---|---|
| Velagliflozin | 15.0 | 15.0 | 15.0 | 15.0 |
| Citric Acid Monohydrate | 9.8 | 9.8 | 9.8 | 9.8 |
| NaOH 1M | 46.4 | 46.4 | 46.4 | 46.4 |
| Cremophor RH40 | 250.0 | — | — | — |
| Polysorbate 80 | — | 250.0 | — | — |
| Poloxamer 188 | — | — | 50.0 | — |
| PEG 400 | — | — | — | 200.0 |
| Sodium benzoate | 2.0 | 2.0 | 2.0 | 2.0 |
| Sorbitol | 170.0 | 170.0 | 170.0 | 170.0 |
| Honey Flavor | 1.5 | 1.5 | 1.5 | 1.5 |
| Water, purified | ad. 1100 ml | ad. 1100 ml | ad. 1100 ml | Ad. 1100 ml |

18. The aqueous pharmaceutical composition according to any one of clauses 1 to 17, wherein such aqueous pharmaceutical composition is for oral and/or parenteral administration, preferably oral administration.

19. The aqueous pharmaceutical composition according to any one of clauses 1 to 18 for use in a method of treating and/or preventing one or more medicinal indications in a subject in need of such treatment and/or prevention, preferably an animal, more preferably a mammal, in particular a horse, cat, dog or cow, selected from among the medicinal indications:

(i) a metabolic disorder of an equine animal, wherein preferably the metabolic disorder is one or more disorders selected from insulin resistance, hyperinsulinemia, impaired glucose tolerance, dyslipidemia, dysadipokinemia, subclinical inflammation, systemic inflammation, low grade systemic inflammation, obesity, and/or regional adiposity, wherein preferably the metabolic disorder is insulin resistance, hyperinsulinemia, and/or a clinical condition associated with insulin resistance and/or hyperinsulinemia; wherein preferably said clinical condition is one or more conditions selected from impaired glucose tolerance, dyslipidemia, dysadipokinemia, subclinical inflammation, systemic inflammation, low grade systemic inflammation, obesity, and/or regional adiposity;

(ii) a metabolic disorder of an equine animal, wherein the metabolic disorder is one or more disorders selected from laminitis, vascular dysfunction, hypertension, hepatic lipidosis, atherosclerosis, hyperadrenocorticism, Pituitary Pars Intermedia Dysfunction and/or Equine Metabolic Syndrome, wherein preferably the metabolic disorder is a clinical condition/sign associated with insulin resistance and/or hyperinsulinemia, wherein said clinical condition/sign preferably is one or more conditions selected from laminitis, vascular dysfunction, hypertension, hepatic lipidosis, atherosclerosis, hyperadrenocorticism, Pituitary Pars Intermedia Dysfunction and/or Equine Metabolic Syndrome;

(iii) a metabolic disorder of a feline animal, wherein preferably the metabolic disorder is one or more selected from the group consisting of: ketoacidosis, pre-diabetes, diabetes mellitus type 1 or type 2, insulin resistance, obesity, hyperglycemia, impaired glucose tolerance, hyperinsulinemia, dyslipidemia, dysadipokinemia, subclinical inflammation, systemic inflammation, low grade systemic inflammation, hepatic lipidosis, atherosclerosis, inflammation of the pancreas, neuropathy and/or Syndrome X (metabolic syndrome) and/or loss of pancreatic beta cell function and/or wherein the remission of the metabolic disorder, preferably diabetic remission, is achieved and/or maintained;

(iv) a metabolic disorder of a canine animal, wherein preferably the metabolic disorder is one or more selected from the group consisting of: ketoacidosis, pre-diabetes, insulin dependent diabetes mellitus, insulin resistance diabetes, insulin resistance, obesity, hyperglycemia, hyperglycemia induced cataract formation, impaired glucose tolerance, hyperinsulinemia, dyslipidemia, dysadipokinemia, subclinical inflammation, systemic inflammation, low grade systemic inflammation, hepatic lipidosis, inflammation of the pancreas, metabolic disorder consequences, such as hypertension, renal dysfunction and/or musculoskeletal disorders, and/or Syndrome X (metabolic syndrome), preferably pre-diabetes, insulin dependent diabetes mellitus, insulin resistance diabetes, insulin resistance, wherein preferably the development of hyperglycemia induced cataract formation is prevented or remission is achieved and/or wherein preferably the development of metabolic disorder consequences, such as hypertension, renal dysfunction and/or musculoskeletal disorders, is prevented or progression is slowed or remission is achieved.

(v) a cardiac disease of a feline animal, wherein preferably the cardiac disease is one or more selected from the group consisting of: heart failure, heart failure due to one or more cardiomyopathies, heart failure due to hypertrophic cardiomyopathy (HCM), heart failure due to restrictive cardiomyopathy (RCM), heart failure due to dilated cardiomyopathy (DCM), heart failure due to unclassified cardiomyopathy (UCM), heart failure due to arrhythmogenic right ventricular cardiomyopathy (ARVC), hypertrophic cardiomyopathy (HCM), restrictive cardiomyopathy (RCM), dilated cardiomyopathy (DCM), unclassified cardiomyopathy (UCM), and/or arrhythmogenic right ventricular cardiomyopathy (ARVC); preferably selected from the group consisting of: heart failure due to one or more cardiomyopathies, heart failure due to hypertrophic cardiomyopathy (HCM), hypertrophic cardiomyopathy (HCM);

(vi) drying-off of a non-human mammal, preferably ruminant, improving and/or facilitating the drying-off of a non-human mammal, preferably ruminant, reducing the milk production, preferably milk production and/or secretion, in a pregnant and/or lactating non-human mammal, preferably ruminant, decreasing milk accumulation and/or engorgement in the udder, preferably udder and/or mammary gland, of a non-human mammal, preferably ruminant, decreasing the discomfort associated with udder engorgement, such as increasing the daily lying time and/or reduction of stress, of a non-human mammal, preferably ruminant, decreasing milk leakage after drying-off of a non-human mammal, preferably ruminant, decreasing the incidence of intramammary infections (IMI), preferably mastitis and/or metritis, in a non-human mammal, preferably ruminant.

20. A process for producing the aqueous pharmaceutical composition according to any one of clauses 1 to 18, comprising the steps (in any meaningful order):

(i) mixing the one or more organic solvents (if any), such as ethanol, with water (if no organic solvents are present, only water is used as starting material);

(ii) adding one or more solubilizing agents to the mixture (or water) resulting from step (i);

(iii) dissolving the at least one SGLT-2 inhibitor, preferably velagliflozin, in the mixture resulting from step (ii);

(iv) optionally, dissolving the one or more preservatives in the mixture resulting from step (iii), (v) optionally, further dissolving further excipients, such as pH modifier(s), flavor(s), sweeteners, antioxidation agents, viscosity-enhancing agents and the like, in the mixture resulting from step (iii) or optionally (iv);

(vi) optionally, filtrating the mixture resulting from step (iii), optionally step (iv) or optionally step (v);

whereby, optionally, independently from each other after any of the individual process steps—be they mandatory or optional—an additional mixing step is performed.

21. A kit-of-parts comprising:

(a) an aqueous pharmaceutical composition according to any one of clauses 1 to 18; and (b) a package leaflet including the information that the aqueous pharmaceutical composition is to be used for the prevention and/or treatment of one or more medicinal indications in a subject in need of such prevention and/or treatment, which are selected from among the medicinal indications:

(i) a metabolic disorder of an equine animal, wherein preferably the metabolic disorder is one or more disorders selected from insulin resistance, hyperinsulinemia, impaired glucose tolerance, dyslipidemia, dysadipokinemia, subclinical inflammation, systemic inflammation, low grade systemic inflammation, obesity, and/or regional adiposity, wherein preferably the metabolic disorder is insulin resistance, hyperinsulinemia, and/or a clinical condition associated with insulin resistance and/or hyperinsulinaemia; wherein preferably said clinical condition is one or more conditions selected from impaired glucose tolerance, dyslipidemia, dysadipokinemia, subclinical inflammation, systemic inflammation, low grade systemic inflammation, obesity, and/or regional adiposity;

(ii) a metabolic disorder of an equine animal, wherein the metabolic disorder is one or more disorders selected from laminitis, vascular dysfunction, hypertension, hepatic lipidosis, atherosclerosis, hyperadrenocorticism, Pituitary Pars Intermedia Dysfunction and/or Equine Metabolic Syndrome, wherein preferably the metabolic disorder is a clinical condition/sign associated with insulin resistance and/or hyperinsulinaemia, wherein said clinical condition/sign preferably is one or more conditions selected from laminitis, vascular dysfunction, hypertension, hepatic lipidosis, atherosclerosis, hyperadrenocorticism, Pituitary Pars Intermedia Dysfunction and/or Equine Metabolic Syndrome;

(iii) a metabolic disorder of a feline animal, wherein preferably the metabolic disorder is one or more selected from the group consisting of: ketoacidosis, pre-diabetes, diabetes mellitus type 1 or type 2, insulin resistance, obesity, hyperglycemia, impaired glucose tolerance, hyperinsulinemia, dyslipidemia, dysadipokinemia, subclinical inflammation, systemic inflammation, low grade systemic inflammation, hepatic lipidosis, atherosclerosis, inflammation of the pancreas, neuropathy and/or Syndrome X (metabolic syndrome) and/or loss of pancreatic beta cell function and/or wherein the remission of the metabolic disorder, preferably diabetic remission, is achieved and/or maintained;

(iv) a metabolic disorder of a canine animal, wherein preferably the metabolic disorder is one or more selected from the group consisting of: ketoacidosis, pre-diabetes, insulin dependent diabetes mellitus, insulin resistance diabetes, insulin resistance, obesity, hyperglycemia, hyperglycemia induced cataract formation, impaired glucose tolerance, hyperinsulinemia, dyslipidemia, dysadipokinemia, subclinical inflammation, systemic inflammation, low grade systemic inflammation, hepatic lipidosis, inflammation of the pancreas, metabolic disorder consequences, such as hypertension, renal dysfunction and/or musculoskeletal disorders, and/or Syndrome X (metabolic syndrome), preferably pre-diabetes, insulin dependent diabetes mellitus, insulin resistance diabetes, insulin resistance, wherein preferably the development of hyperglycemia induced cataract formation is prevented or remission is achieved and/or wherein preferably the development of metabolic disorder consequences, such as hypertension, renal dysfunction and/or musculoskeletal disorders, is prevented or progression is slowed or remission is achieved.

(v) a cardiac disease of a feline animal, wherein preferably the cardiac disease is one or more selected from the group consisting of: heart failure, heart failure due to one or more cardiomyopathies, heart failure due to hypertrophic cardiomyopathy (HCM), heart failure due to restrictive cardiomyopathy (RCM), heart failure due to dilated cardiomyopathy (DCM), heart failure due to unclassified cardiomyopathy (UCM), heart failure due to arrhythmogenic right ventricular cardiomyopathy (ARVC), hypertrophic cardiomyopathy (HCM), restrictive cardiomyopathy (RCM), dilated cardiomyopathy (DCM), unclassified cardiomyopathy (UCM), and/or arrhythmogenic right ventricular cardiomyopathy (ARVC); preferably selected from the group consisting of: heart failure due to one or more cardiomyopathies, heart failure due to hypertrophic cardiomyopathy (HCM), hypertrophic cardiomyopathy (HCM);

(vi) drying-off of a non-human mammal, preferably ruminant, improving and/or facilitating the drying-off of a non-human mammal, preferably ruminant, reducing the milk production, preferably milk production and/or secretion, in a pregnant and/or lactating non-human mammal, preferably ruminant, decreasing milk accumulation and/or engorgement in the udder, preferably udder and/or mammary gland, of a non-human mammal, preferably ruminant, decreasing the discomfort associated with udder engorgement, such as increasing the daily lying time and/or reduction of stress, of a non-human mammal, preferably ruminant, decreasing milk leakage after drying-off of a non-human mammal, preferably ruminant, decreasing the incidence of intramammary infections (IMI), preferably mastitis and/or metritis, in a non-human mammal, preferably ruminant.

The invention claimed is:

1. An aqueous pharmaceutical composition comprising at least one SGLT-2 inhibitor and one or more solubilizing agents, wherein:

the aqueous pharmaceutical composition is free of ethanol, propane-1,2-diol (propylene glycol), and glycerol; and the at least one SGLT-2 inhibitor comprises Velagliflozin, represented by the following formula:

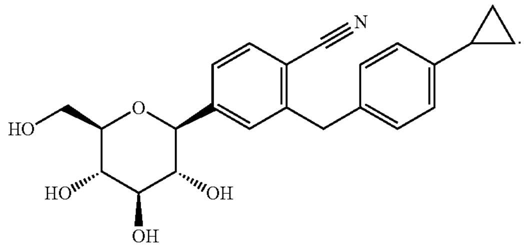 [SMILES: N#Cc1ccc([C@@H]2O[C@H](CO)[C@@H](O)[C@H](O)[C@H]2O)cc1Cc1ccc(C2CC2)cc1]

2. The aqueous pharmaceutical composition according to claim 1, wherein the at least one SGLT-2 inhibitor further includes one or more SGLT-2 inhibitors selected from the group consisting of:

(1) a glucopyranosyl-substituted benzene derivative of the formula (1) other than Velagliflozin

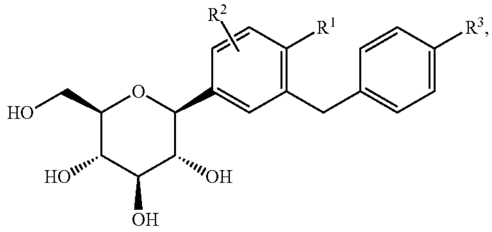

wherein $R^1$ denotes cyano, or methyl;

$R^2$ denotes H, methyl, methoxy or hydroxy; and $R^3$ denotes cyclopropyl, hydrogen, fluorine, chlorine, bromine, iodine, methyl, ethyl, propyl, isopropyl, butyl, sec-butyl, iso-butyl, tert-butyl, 3-methyl-but-1-yl, cyclobutyl, cyclopentyl, cyclohexyl, 1-hydroxy-cyclopropyl, 1-hydroxy-cyclobutyl, 1-hydroxy-cyclopentyl, 1-hydroxy-cyclohexyl, ethinyl, ethoxy, difluoromethyl, trifluoromethyl, pentafluoroethyl, 2-hydroxyl-ethyl, hydroxymethyl, 3-hydroxy-propyl, 2-hydroxy-2-methyl-prop-1-yl, 3-hydroxy-3-methyl-but-1-yl, 1-hydroxy-1-methyl-ethyl, 2,2,2-trifluoro-1-hydroxy-1-methyl-ethyl, 2,2,2-trifluoro-1-hydroxy-1-trifluoromethyl-ethyl, 2-methoxy-ethyl, 2-ethoxy-ethyl, hydroxy, difluoromethyloxy, trifluoromethyloxy, 2-methyloxy-ethyloxy, methylsulfanyl, methylsulfinyl, methlysulfonyl, ethylsulfinyl, ethylsulfonyl, trimethylsilyl, (R)-tetrahydro-furan-3-yloxy or (S)-tetrahydrofuran-3-yloxy or cyano;

wherein $R^3$ is selected from cyclopropyl, ethyl, ethinyl, ethoxy, (R)-tetrahydrofuran-3-yloxy or (S)-tetrahydrofuran-3-yloxy;

or a derivative thereof wherein one or more hydroxyl groups of the β-D-glucopyranosyl group are acylated with groups selected from ($C_{1-18}$-alkyl)carbonyl, ($C_{1-18}$-alkyl)oxycarbonyl, phenylcarbonyl and phenyl-($C_{1-3}$-alkyl)-carbonyl;

(3) Dapagliflozin, represented by formula (3):

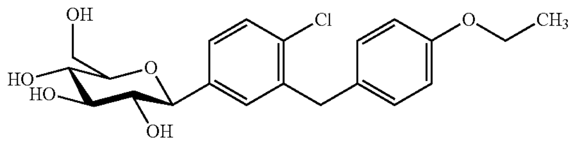

(4) Canagliflozin, represented by formula (4):

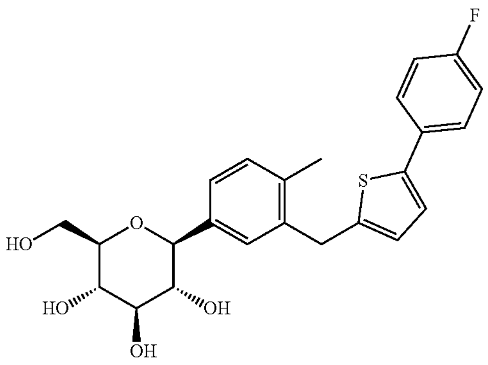 [SMILES: Cc1ccc([C@@H]2O[C@H](CO)[C@@H](O)[C@H](O)[C@H]2O)cc1Cc1ccc(-c2ccc(F)cc2)s1]

(5) Empagliflozin, represented by formula (5):

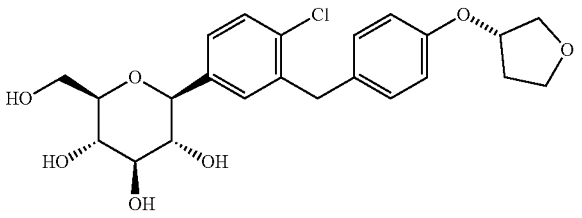

(6) Luseogliflozin, represented by formula (6):

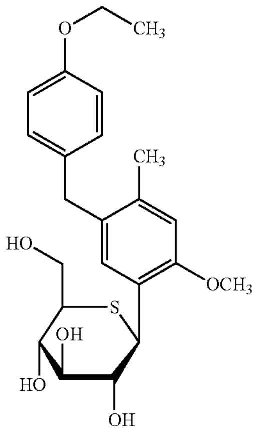

(7) Tofogliflozin, represented by formula (7):

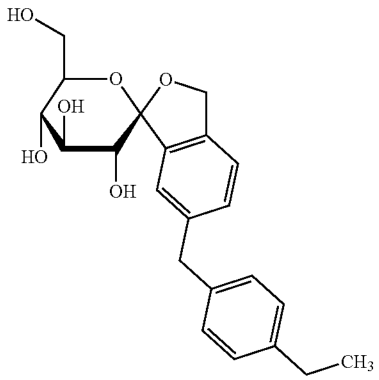

(8) Ipragliflozin, represented by formula (8):

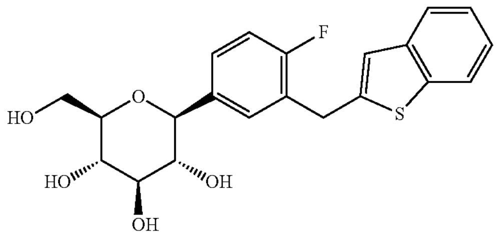 [SMILES: OC[C@H]1O[C@@H](c2ccc(F)c(Cc3cc4ccccc4s3)c2)[C@H](O)[C@@H](O)[C@@H]1O]

(9) Ertugliflozin, represented by formula (9):

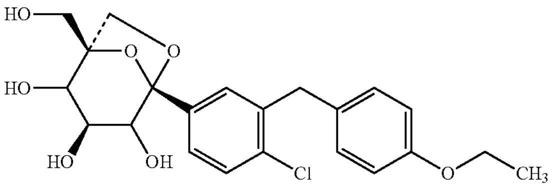 [SMILES: CCOc1ccc(Cc2cc([C@]34OC[C@](CO)(O3)C(O)[C@H](O)C4O)ccc2Cl)cc1]

(10) Atigliflozin, represented by formula (10):

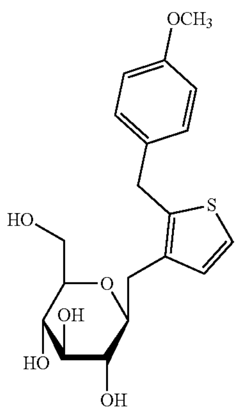

(11) Remogliflozin, represented by formula (11):

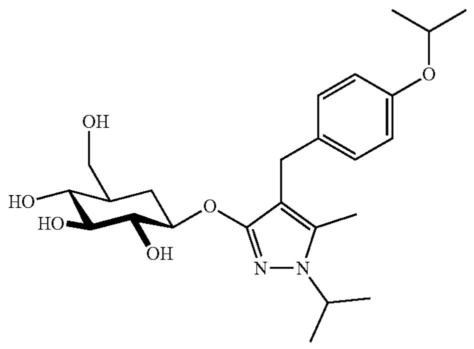

(11A) Remogliflozin etabonate, represented by formula (11A):

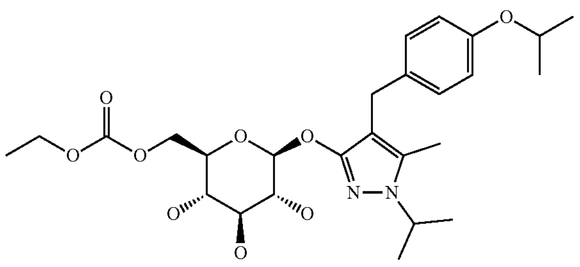 [SMILES: CCOC(=O)OC[C@H]1O[C@@H](Oc2nn(C(C)C)c(C)c2Cc2ccc(OC(C)C)cc2)[C@H](O)[C@@H](O)[C@@H]1O]

(12) a thiophene derivative of the formula (12)

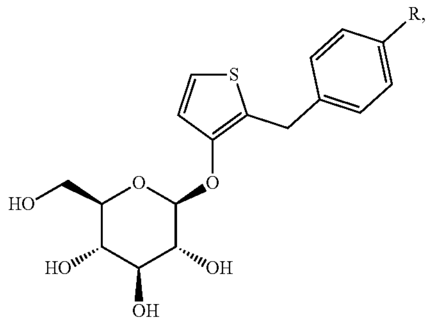

wherein R denotes methoxy or trifluoromethoxy;

(13) 1-(β-D-glucopyranosyl)-4-methyl-3-[5-(4-fluoro-phenyl)-2-thienylmethyl]benzene, represented by formula (13);

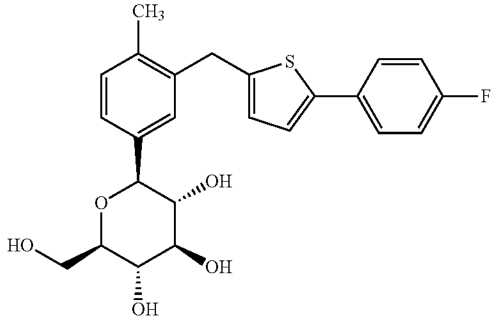 [SMILES: Cc1ccc([C@@H]2O[C@H](CO)[C@@H](O)[C@H](O)[C@H]2O)cc1Cc1ccc(-c2ccc(F)cc2)s1]

(14) a spiroketal derivative of the formula (14):

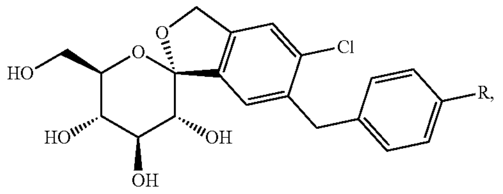

wherein R denotes methoxy, trifluoromethoxy, ethoxy, ethyl, isopropyl or tert butyl;

(15) a pyrazole-O-glucoside derivative of the formula (15)

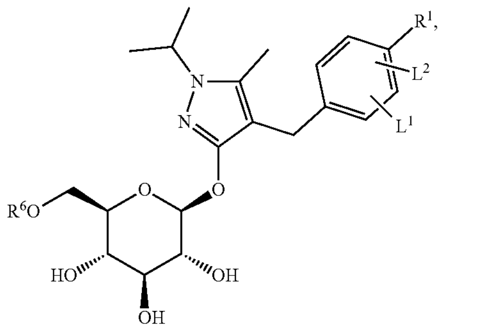

wherein $R^1$ denotes $C_{1-3}$-alkoxy, $L^1$, $L^2$ independently of each other denote H or F, $R^6$ denotes H, ($C_{1-3}$-alkyl)carbonyl, ($C_{1-6}$-alkyl)oxy-carbonyl, phenyloxycarbonyl, benzyloxycarbonyl or benzylcarbonyl;

(16) Sotagliflozin, represented by formula (16):

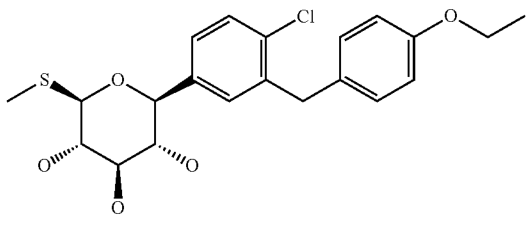 [SMILES: CCOc1ccc(Cc2cc([C@@H]3O[C@H](SC)[C@@H](O)[C@H](O)[C@H]3O)ccc2Cl)cc1]

(17) Sergliflozin, represented by formula (17):

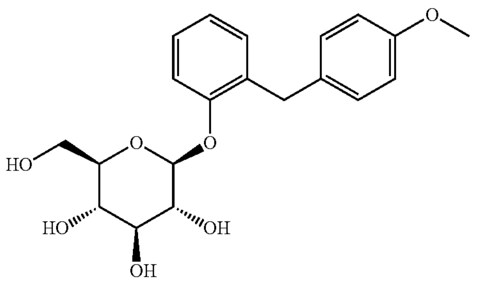 [SMILES: COc1ccc(Cc2ccccc2O[C@@H]2O[C@H](CO)[C@@H](O)[C@H](O)[C@H]2O)cc1]

(18) a compound represented by formula (18):

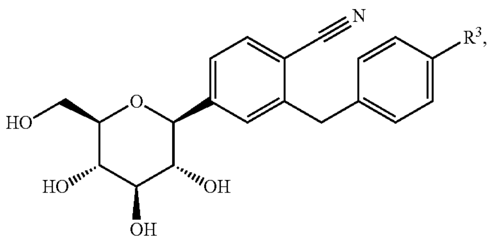

wherein $R^3$ denotes cyclopropyl, hydrogen, fluorine, chlorine, bromine, iodine, methyl, ethyl, propyl, isopropyl, butyl, sec-butyl, iso-butyl, tert-butyl, 3-methyl-but-1-yl, cyclobutyl, cyclopentyl, cyclohexyl, 1-hydroxy-cyclopropyl, 1-hydroxy-cyclobutyl, 1-hydroxy-cyclopentyl, 1-hydroxy-cyclohexyl, ethinyl, ethoxy, difluoromethyl, trifluoromethyl, pentafluoroethyl, 2-hydroxyl-ethyl, hydroxymethyl, 3-hydroxy-propyl, 2-hydroxy-2-methyl-prop-1-yl, 3-hydroxy-3-methyl-but-1-yl, 1-hydroxy-1-methyl-ethyl, 2,2,2-trifluoro-1-hydroxy-1-methyl-ethyl, 2,2,2-trifluoro-1-hydroxy-1-trifluoromethyl-ethyl, 2-methoxy-ethyl, 2-ethoxy-ethyl, hydroxy, difluoromethyloxy, trifluoromethyloxy, 2-methyloxy-ethyloxy, methyl-sulfanyl, methylsulfinyl, methlysulfonyl, ethylsulfinyl, ethylsulfonyl, trimethylsilyl, (R)-tetrahydro-furan-3-yloxy or (S)-tetrahydrofuran-3-yloxy or cyano, and wherein $R^3$ is selected from cyclopropyl, ethyl, ethinyl, ethoxy, (R)-tetrahydrofuran-3-yloxy or (S)-tetrahydrofuran-3-yloxy;

or a derivative thereof wherein one or more hydroxyl groups of the β-D-glucopyranosyl group are acylated with groups selected from ($C_{1-18}$-alkyl)carbonyl, ($C_{1-18}$-alkyl)oxycarbonyl, phenylcarbonyl and phenyl-($C_{1-3}$-alkyl)-carbonyl;

(19) Bexagliflozin, represented by formula (19):

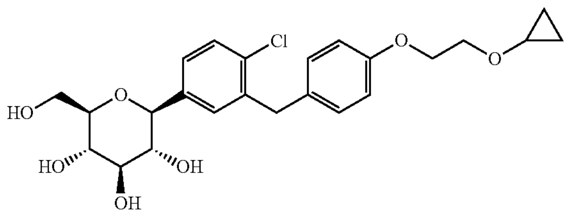 [SMILES: OC[C@H]1O[C@@H](c2ccc(Cl)c(Cc3ccc(OCCOC4CC4)cc3)c2)[C@H](O)[C@@H](O)[C@@H]1O]

(20) Janagliflozin, represented by formula (20):

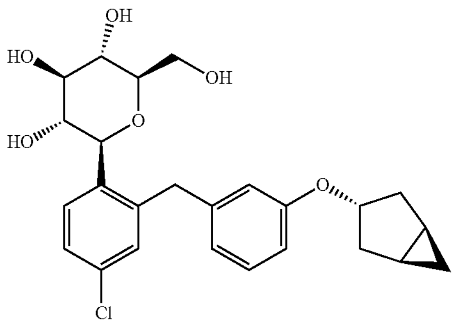 [SMILES: OC[C@H]1O[C@@H](c2ccc(Cl)cc2Cc2cccc(O[C@H]3C[C@@H]4C[C@@H]4C3)c2)[C@H](O)[C@@H](O)[C@@H]1O]

(21) Rongliflozin, represented by formula (21):

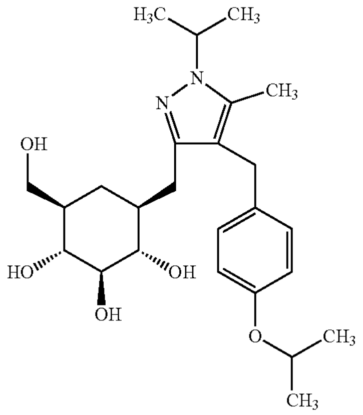 [SMILES: Cc1c(Cc2ccc(OC(C)C)cc2)c(C[C@@H]2C[C@H](CO)[C@@H](O)[C@H](O)[C@H]2O)nn1C(C)C]

(22) Wanpagliflozin;

(23) Enavogliflozin, represented by formula (23):

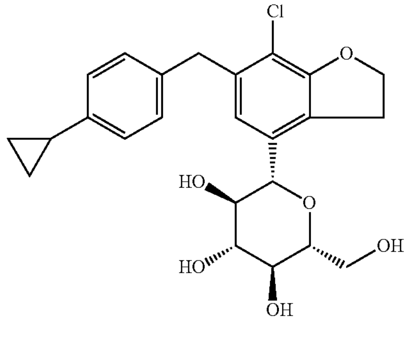 [SMILES: OC[C@H]1O[C@@H](c2cc(Cc3ccc(C4CC4)cc3)c(Cl)c3c2CCO3)[C@H](O)[C@@H](O)[C@@H]1O]

(24) TFC-039, represented by formula (24):

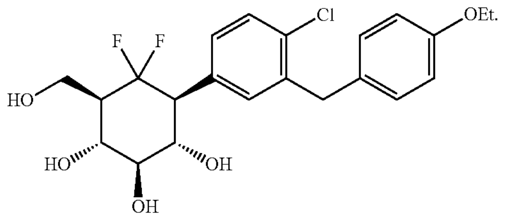 [SMILES: CCOc1ccc(Cc2cc([C@H]3[C@H](O)[C@@H](O)[C@H](O)[C@@H](CO)C3(F)F)ccc2Cl)cc1]

3. The aqueous pharmaceutical composition according to claim 1, wherein velagliflozin is the only SGLT-2 inhibitor contained in the aqueous pharmaceutical composition.

4. The aqueous pharmaceutical composition according to claim 1, wherein the aqueous pharmaceutical composition is for direct, administration to a subject, without further mandatory processing and/or purification steps, or to an animal, or to a mammal, or to a horse, cat, dog or cow.

5. The aqueous pharmaceutical composition according to claim 4, wherein the aqueous pharmaceutical composition is sterile.

6. The aqueous pharmaceutical composition according to claim 1, wherein the one or more solubilizing agents are selected from the group consisting of: surfactants, anionic surfactants, non-ionic surfactants, hydrogenated castor oils, polyoxyethylene-polyoxypropylene block copolymers, polyethylene glycols, propylene glycol derivatives, and polyvinylpyrrolidones, and the total amount of the one or more solubilizing agents is from 1 to 50 g/100 mL (1-50% w/v).

7. The aqueous pharmaceutical composition according to claim 1, wherein two or more solubilizing agents are contained in the aqueous pharmaceutical composition.

8. The aqueous pharmaceutical composition according to claim 7, wherein two solubilizing agents are contained in the aqueous pharmaceutical composition, wherein the amount of the first solubilizing agent and the amount of the second solubilizing agent are independently from each other selected from 1 to 50 g/100 mL (1-50% w/v), or from 1 to 45 g/100 mL (1-45% w/v), or from 1 to 40 g/100 mL (1-40% w/v), or from 1 to 35 g/100 mL (1-35% w/v), or from 1 to 30 g/100 mL (1-30% w/v), or from 1 to 25 g/100 mL (1-25% w/v), or from 5 to 25 g/100 mL (5-25% w/v).

9. The aqueous pharmaceutical composition according to claim 8, wherein the two solubilizing agents are independently from each other selected from the group consisting of: sodium dodecyl sulphate (SDS), Cremophor RH 40 (PEG-40 Hydrogenated Castor Oil, Macrogol glycerol hydroxystearate 40), polysorbate 20, Lutrol F 68 (Poloxamer 188), PEG 200, PEG 300, PEG 400, propylene glycol monolaurate, Kollidon 12 (povidone).

10. The aqueous pharmaceutical composition according to claim 9, wherein the two solubilizing agents are Kollidon 12 (povidone) as well as PEG 200, PEG 300 or PEG 400.

11. The aqueous pharmaceutical composition according to claim 10, wherein the two solubilizing agents are Kollidon 12 (povidone) and PEG 300.

12. The aqueous pharmaceutical composition according to claim 1, wherein the aqueous pharmaceutical composition is a solution, an emulsion or a suspension, or a solution, an emulsion or a suspension with an NTU value of equal to or less than 10.0, or equal to or less than 7.0, or equal to or less than 3.0.

13. The aqueous pharmaceutical composition according to claim 12, wherein the aqueous pharmaceutical composition is a solution with an NTU value of equal to or less than 3.0.

14. The aqueous pharmaceutical composition according to claim 1, wherein the aqueous pharmaceutical composition contains from 30 to 100 g/100 mL (30 to 100% w/v), or from 30 to 95 g/100 mL (30 to 95% w/v), or from 30 to 90 g/100 mL (30 to 90% w/v), or from 30 to 85 g/100 mL (30 to 85% w/v), or from 30 to 80 g/100 mL (30 to 80% w/v), or from 50 to 80 g/100 mL (50 to 80% w/v) water, or in the form of aqueous buffer.

15. The aqueous pharmaceutical composition according to claim 14, wherein the aqueous pharmaceutical composition has a pH value of from 2 to 7, or from 3 to 7, or from 3.0 to 6.5, or from 4.0 to 6.5, or from 4.0 to 5.0, or of 4.5.

16. The aqueous pharmaceutical composition according to claim 1, wherein the aqueous pharmaceutical composition additionally comprises one or more preservatives selected from the group consisting of: sorbic acid or salts thereof, benzoic acid or salts thereof, benzalkonium chloride; benzethonium chloride; benzyl alcohol, cetylpyridinium chloride; sodium metabisulfite; sodium acetate; and parabens and salts thereof.

17. The aqueous pharmaceutical composition according to claim 1, wherein the aqueous pharmaceutical composition additionally comprises one or more antioxidation agents selected from the group consisting of: ascorbic acid or pharmaceutically acceptable salts thereof, citric acid (anhydrous and/or monohydrate) or pharmaceutically acceptable salts thereof; erythorbic acid; fumaric acid; malic acid; monothioglycerol; phosphoric acid; sodium metabisulfite; potassium metabisulfite; propionic acid; sodium bisulfite; sodium sulfite; resveratrol; butylhydroxyanisol; butylhydroxytoluene; gallate derivatives; Vitamin E or pharmaceutically acceptable salts thereof; ascorbyl palmitate; and edetic acid or pharmaceutically acceptable salts thereof.

18. The aqueous pharmaceutical composition according to claim 1, wherein the aqueous pharmaceutical composition additionally comprises one or more viscosity-enhancing agents selected from the group consisting of: inorganic gel forming agents, organic gel forming agents, and cellulose derivatives.

19. The aqueous pharmaceutical composition according to claim 1, wherein the aqueous pharmaceutical composition additionally comprises one or more flavours and/or sweeteners selected from the group consisting of: honey flavor, lime/salvia flavor, jasmine flavor, lavender flavor, peppermint flavor, raspberry flavor, lemon flavor, herbs flavor, meat flavor, vanillin/vanilla flavor, saccharine, aspartame, sorbitol, and xylitol.

20. The aqueous pharmaceutical composition according to claim 1, comprising:

one or more preservatives selected from the group consisting of: sorbic acid or salts thereof; benzoic acid or salts thereof, benzethonium chloride; benzyl alcohol, cetylpyridinium chloride; sodium metabisulfite; sodium acetate; and parabens and salts thereof;

one or more flavors and/or sweeteners selected from the group consisting of: honey flavor, lime/salvia flavor, jasmine flavor, lavender flavor, peppermint flavor, raspberry flavor, lemon flavor, herbs flavor, meat flavor, vanillin/vanilla flavor, saccharine, aspartame, sorbitol, xylitol;

water in the form of aqueous buffer with pH 4.5;

one or more solubilizing agents selected from the group consisting of: surfactants, anionic surfactants, non-ionic surfactants, hydrogenated castor oils, polyoxyethylene-polyoxypropylene block copolymers, polyethylene glycols, propylene glycol derivatives, and polyvinylpyrrolidones;

one or more viscosity-enhancing agents selected from the group consisting of: inorganic gel forming agents, organic gel forming agents, and cellulose derivatives; and one or more antioxidation agents selected from the group consisting of: ascorbic acid or pharmaceutically acceptable salts thereof; citric acid (anhydrous and/or monohydrate) or pharmaceutically acceptable salts thereof; erythorbic acid; fumaric acid; malic acid; monothioglycerol; phosphoric acid; sodium metabisulfite; potassium metabisulfite; propionic acid; sodium bisulfite; sodium sulfite; resveratrol; butylhydroxyanisol; butylhydroxytoluene; gallate derivatives; Vitamin E or pharmaceutically acceptable salts thereof; ascorbyl palmitate; and edetic acid or pharmaceutically acceptable salts thereof.

21. The aqueous pharmaceutical composition according to claim 1, comprising:

0.5-20.0 g/100 mL (0.5-20.0% w/v), or 0.5-15.0 g/100 mL (0.5-15.0% w/v), or 1.0-1.5 g/100 mL (1.0-1.5% w/v) of velagliflozin as a single SGLT-2 inhibitor;

0-3.0 g/100 mL (0-3.0% w/v), or 0.05-3.0 g/100 mL (0.05-3.0% w/v), or 0.05-2.0 g/100 mL (0.05-2.0% w/v) of one or more preservatives selected from the group consisting of: sorbic acid or salts thereof; benzoic acid or salts thereof; benzalkonium chloride; benzethonium chloride; benzyl alcohol; cetylpyridinium chloride; sodium metabisulfite; sodium acetate; and parabens and salts thereof;

0-40 g/100 mL (0-40% w/v), or 0-30 g/100 mL (0-30% w/v), or 0-2 g/100 mL (0-2% w/v) of one or more flavors and/or sweeteners selected from the group consisting of: honey flavor, lime/salvia flavor, jasmine flavor, lavender flavor, peppermint flavor, raspberry flavor, lemon flavor, herbs flavor, meat flavor, vanillin/vanilla flavor, saccharine, aspartame, sorbitol, and xylitol;

30 to 100 g/100 mL (30 to 100% w/v), or from 30 to 95 g/100 mL (30 to 95% w/v), or from 30 to 90 g/100 mL (30 to 90% w/v), or from 30 to 85 g/100 mL (30 to 85% w/v), or from 30 to 80 g/100 mL (30 to 80% w/v), or from 50 to 80 g/100 mL (50 to 80% w/v) water in the form of aqueous buffer with pH 4.5;

1 to 50 g/100 mL (1-50% w/v), or from 1 to 45 g/100 mL (1-45% w/v), or from 1 to 40 g/100 mL (1-40% w/v), or from 1 to 35 g/100 mL (1-35% w/v), or from 1 to 30 g/100 mL (1-30% w/v), or from 1 to 25 g/100 mL (1-25% w/v), or from 5 to 25 g/100 mL (5-25% w/v) of one or more solubilizing agents selected from the group consisting of: surfactants, anionic surfactants, non-ionic surfactants, hydrogenated castor oils, polyoxyethylene-polyoxypropylene block copolymers, polyethylene glycols, propylene glycol derivatives, and polyvinylpyrrolidones;

0-40 g/100 mL (0-40% w/v), or 10-30 g/100 mL (10-30% w/v) of one or more viscosity-enhancing agents selected from the group consisting of: inorganic gel forming agents, organic gel forming agents, cellulose derivatives; and 0-1.0 g/100 mL (0-1.0% w/v), or 0-0.5 g/100 mL (0-0.5% w/v), or 0.1-0.3 g/100 mL (0.1-0.3% w/v) of one or more antioxidation agents selected from the group consisting of: ascorbic acid or pharmaceutically acceptable salts thereof, citric acid (anhydrous and/or monohydrate) or pharmaceutically acceptable salts thereof; erythorbic acid; fumaric acid; malic acid; monothioglycerol; phosphoric acid; sodium metabisulfite; potassium metabisulfite; propionic acid; sodium bisulfite; sodium sulfite; resveratrol; butylhydroxyanisol; butylhydroxytoluene; gallate derivatives; Vitamin E or pharmaceutically acceptable salts thereof; ascorbyl palmitate; and edetic acid or pharmaceutically acceptable salts thereof.

22. The aqueous pharmaceutical composition according to claim 1, consisting of: velagliflozin; sodium dodecyl sulphate (SDS), Cremophor RH 40 (PEG-40 Hydrogenated Castor Oil, Macrogol glycerol hydroxystearate 40), polysorbate 20, Lutrol F 68 (Poloxamer 188), PEG 200, PEG 300, PEG 400, propylene glycol monolaurate and/or Kollidon 12 (povidone); sodium benzoate; and water.

23. The aqueous pharmaceutical composition according to claim 1, consisting of: velagliflozin; citric acid monohydrate; NaOH; sodium dodecyl sulphate (SDS), Cremophor RH 40 (PEG-40 Hydrogenated Castor Oil, Macrogol glycerol hydroxystearate 40), polysorbate 20, Lutrol F 68 (Poloxamer 188), PEG 200, PEG 300, PEG 400, propylene glycol monolaurate and/or Kollidon 12 (povidone); sodium benzoate; and water.

24. The aqueous pharmaceutical composition according to claim 1, consisting of: velagliflozin; citric acid monohydrate; NaOH; sodium dodecyl sulphate (SDS), Cremophor RH 40 (PEG-40 Hydrogenated Castor Oil, Macrogol glycerol hydroxystearate 40), polysorbate 20, Lutrol F 68 (Poloxamer 188), PEG 200, PEG 300, PEG 400, propylene glycol monolaurate and/or Kollidon 12 (povidone); sodium benzoate; sorbitol and/or xylitol; honey flavor and/or vanillin and/or meat flavor; and water.

25. The aqueous pharmaceutical composition according to claim 1, wherein the aqueous pharmaceutical composition is for oral and/or parenteral administration.

26. A method of treating and/or preventing one or more medicinal indications in a subject in need of such treatment and/or prevention by administering the aqueous pharmaceutical composition according to claim 1, to the subject, wherein the subject is a mammal, or a horse, or a cat, or a dog, or a cow, and the one or more medicinal indications is selected from the group consisting of:

(i) a metabolic disorder and/or a clinical condition of an equine animal, wherein the metabolic disorder is one or more disorders selected from insulin resistance, hyperinsulinemia, impaired glucose tolerance, dyslipidemia, dysadipokinemia, subclinical inflammation, systemic inflammation, low grade systemic inflammation, obesity, and/or regional adiposity, and the clinical condition is one or more conditions selected from impaired glucose tolerance, dyslipidemia, dysadipokinemia, subclinical inflammation, systemic inflammation, low grade systemic inflammation, obesity, and/or regional adiposity;

(ii) a metabolic disorder of an equine animal, wherein the metabolic disorder is one or more disorders selected from laminitis, vascular dysfunction, hypertension, hepatic lipidosis, atherosclerosis, hyperadrenocorticism, Pituitary Pars Intermedia Dysfunction and/or Equine Metabolic Syndrome, or wherein the metabolic disorder is a clinical condition/sign associated with insulin resistance and/or hyperinsulinemia, wherein said clinical condition/sign is one or more conditions selected from laminitis, vascular dysfunction, hypertension, hepatic lipidosis, atherosclerosis, hyperadrenocorticism, Pituitary Pars Intermedia Dysfunction and/or Equine Metabolic Syndrome;

(iii) a metabolic disorder of a feline animal, wherein the metabolic disorder is one or more selected from the group consisting of: ketoacidosis, pre-diabetes, diabetes mellitus type 1 or type 2, insulin resistance, acromegaly, diabetes with elevated IGF-1 concentration, obesity, hyperglycemia, impaired glucose tolerance, hyperinsulinemia, dyslipidemia, dysadipokinemia, subclinical inflammation, systemic inflammation, low grade systemic inflammation, hepatic lipidosis, atherosclerosis, inflammation of the pancreas, neuropathy and/or Syndrome X (metabolic syndrome) and/or loss of pancreatic beta cell function and/or wherein the remission of the metabolic disorder is achieved and/or maintained;

(iv) a metabolic disorder of a canine animal, wherein the metabolic disorder is one or more selected from the group consisting of: ketoacidosis, pre-diabetes, insulin dependent diabetes mellitus, insulin resistance diabetes, insulin resistance, obesity, hyperglycemia, hyperglycemia induced cataract formation, impaired glucose tolerance, hyperinsulinemia, dyslipidemia, dysadipokinemia, subclinical inflammation, systemic inflammation, low grade systemic inflammation, hepatic lipidosis, inflammation of the pancreas, and metabolic disorder consequences selected from the group consisting of hypertension, renal dysfunction, and musculoskeletal disorders, and Syndrome X (metabolic syndrome), wherein the development of hyperglycemia induced cataract formation is prevented or remission is achieved and/or wherein the development of metabolic disorder consequences is prevented or progression is slowed or remission is achieved;

(v) a cardiac disease of a feline animal, wherein the cardiac disease is one or more selected from the group consisting of: heart failure, heart failure due to one or more cardiomyopathies, heart failure due to hypertrophic cardiomyopathy (HCM), heart failure due to restrictive cardiomyopathy (RCM), heart failure due to dilated cardiomyopathy (DCM), heart failure due to unclassified cardiomyopathy (UCM), heart failure due to arrhythmogenic right ventricular cardiomyopathy (ARVC), hypertrophic cardiomyopathy (HCM), restrictive cardiomyopathy (RCM), dilated cardiomyopathy (DCM), unclassified cardiomyopathy (UCM), and/or and arrhythmogenic right ventricular cardiomyopathy (ARVC);

(vi) drying-off of a non-human mammal, improving and/or facilitating the drying-off of a non-human mammal, reducing the milk production and/or secretion, in a pregnant and/or lactating non-human mammal, decreasing milk accumulation and/or engorgement in the udder and/or mammary gland, of a non-human mammal, decreasing the discomfort associated with udder engorgement of a non-human mammal, decreasing milk leakage after drying-off of a non-human mammal, and decreasing the incidence of intra-mammary infections (IMI) in a non-human mammal;

(vii) a cardiac disease of a canine, wherein the cardiac disease is one or more selected from the group consisting of: heart failure; congestive heart failure; asymptomatic/preclinical/occult heart failure; heart failure due to (myxomatous) mitral valve disease [(M)MVD]; congestive heart failure due to (myxomatous) mitral valve disease [(M)MVD]; asymptomatic/preclinical/occult heart failure due to (myxomatous) mitral valve disease [(M)MVD]; (myxomatous) mitral valve disease [(M)MVD]; clinically overt (myxomatous) mitral valve disease [(M)MVD]; asymptomatic/preclinical/occult (myxomatous) mitral valve disease [(M)MVD]; heart failure due to dilated cardiomyopathy (DCM); congestive heart failure due to dilated cardiomyopathy (DCM); asymptomatic/preclinical/occult heart failure due to dilated cardiomyopathy (DCM); dilated cardiomyopathy (DCM); clinically overt dilated cardiomyopathy (DCM); asymptomatic/preclinical/occult dilated cardiomyopathy (DCM); and aortic stenosis (valvular, supravalvular and/or subvalvular);

(viii) hypertension in a cat or a dog, wherein the hypertension is one or more selected from the group consisting of: situational hypertension, secondary hypertension and idiopathic hypertension, wherein the secondary hypertension is selected from the group consisting of hypertension associated with chronic kidney disease (CKD), diabetes, obesity, heart disease, endocrine disease, hyperthyroidism, acromegaly, and elevated blood pressure (BP) induced by medicaments; and (ix) a renal disease of a cat or a dog, wherein the renal disease is one or more selected from the group consisting of: renal dysplasia, glomerulopathy, polycystic kidney disease, amyloidosis, tubulo-nephritis/tubulointerstitial nephritis (TIN), acute kidney disease, chronic kidney disease.

27. A process for producing the aqueous pharmaceutical composition according to claim 1, comprising the steps (in any meaningful order):

(i) providing water as starting material;

(ii) adding one or more solubilizing agents to the water from step (i) to form a mixture;

(iii) dissolving the at least one SGLT-2 inhibitor comprising velagliflozin, in the mixture resulting from step (ii);

(iv) optionally, dissolving one or more preservatives in the mixture resulting from step (iii), (v) optionally, further dissolving one or more further excipients selected from the group consisting of pH modifier(s), flavor(s), sweeteners, antioxidation agents, and viscosity-enhancing agents, and in the mixture resulting from step (iii) or optionally (iv);

(vi) optionally, filtrating the mixture resulting from step (iii), optionally step (iv) or optionally step (v);

whereby, optionally, independently from each other after any of the individual process steps—be they mandatory or optional—an additional mixing step is performed.

28. A kit-of-parts comprising:

(a) an aqueous pharmaceutical composition according to claim 1; and (b) a package leaflet including the information that the aqueous pharmaceutical composition is to be used for the prevention and/or treatment of one or more medicinal indications in a subject in need of such prevention and/or treatment, which are selected from among the medicinal indications:

(i) a metabolic disorder and/or a clinical condition of an equine animal, wherein the metabolic disorder is one or more disorders selected from insulin resistance, hyperinsulinemia, impaired glucose tolerance, dyslipidemia, dysadipokinemia, subclinical inflammation, systemic inflammation, low grade systemic inflammation, obesity, and/or regional adiposity; wherein said clinical condition is one or more conditions selected from impaired glucose tolerance, dyslipidemia, dysadipokinemia, subclinical inflammation, systemic inflammation, low grade systemic inflammation, obesity, and regional adiposity;

(ii) a metabolic disorder of an equine animal, wherein the metabolic disorder is one or more disorders selected from laminitis, vascular dysfunction, hypertension, hepatic lipidosis, atherosclerosis, hyperadrenocorticism, Pituitary Pars Intermedia Dysfunction and/or Equine Metabolic Syndrome, or the metabolic disorder is a clinical condition/sign associated with insulin resistance and/or hyperinsulinaemia, wherein said clinical condition/sign is one or more conditions selected from laminitis, vascular dysfunction, hypertension, hepatic lipidosis, atherosclerosis, hyperadrenocorticism, Pituitary Pars Intermedia Dysfunction and/or Equine Metabolic Syndrome;

(iii) a metabolic disorder of a feline animal, wherein the metabolic disorder is one or more selected from the group consisting of: ketoacidosis, pre-diabetes, diabetes mellitus type 1 or type 2, insulin resistance, acromegaly, diabetes with elevated IGF-1 concentration, obesity, hyperglycemia, impaired glucose tolerance, hyperinsulinemia, dyslipidemia, dysadipokinemia, subclinical inflammation, systemic inflammation, low grade systemic inflammation, hepatic lipidosis, atherosclerosis, inflammation of the pancreas, neuropathy and/or Syndrome X (metabolic syndrome), and loss of pancreatic beta cell function, wherein the remission of the metabolic disorder is achieved and/or maintained;

(iv) a metabolic disorder of a canine animal, wherein the metabolic disorder is one or more selected from the group consisting of: ketoacidosis, pre-diabetes, insulin dependent diabetes mellitus, insulin resistance diabetes, insulin resistance, obesity, hyperglycemia, hyperglycemia induced cataract formation, impaired glucose tolerance, hyperinsulinemia, dyslipidemia, dysadipokinemia, subclinical inflammation, systemic inflammation, low grade systemic inflammation, hepatic lipidosis, inflammation of the pancreas, metabolic disorder consequences selected from the group consisting of hypertension, renal dysfunction, and musculoskeletal disorders, and Syndrome X (metabolic syndrome), wherein the development of hyperglycemia induced cataract formation is prevented or remission is achieved and/or wherein the development of metabolic disorder consequences is prevented or progression is slowed or remission is achieved;

(v) a cardiac disease of a feline animal, wherein the cardiac disease is one or more selected from the group consisting of: heart failure, heart failure due to one or more cardiomyopathies, heart failure due to hypertrophic cardiomyopathy (HCM), heart failure due to restrictive cardiomyopathy (RCM), heart failure due to dilated cardiomyopathy (DCM), heart failure due to unclassified cardiomyopathy (UCM), heart failure due to arrhythmogenic right ventricular cardiomyopathy (ARVC), hypertrophic cardiomyopathy (HCM), restrictive cardiomyopathy (RCM), dilated cardiomyopathy (DCM), unclassified cardiomyopathy (UCM), and/or arrhythmogenic right ventricular cardiomyopathy (ARVC);

(vi) drying-off of a non-human mammal, improving and/or facilitating the drying-off of a non-human mammal, reducing the milk production and/or secretion in a pregnant and/or lactating non-human mammal, decreasing milk accumulation and/or engorgement in the udder and/or mammary gland of a non-human mammal, decreasing the discomfort associated with udder engorgement of a non-human mammal, decreasing milk leakage after drying-off of a non-human mammal, and decreasing the incidence of intra-mammary infections (IMI) in a non-human mammal;

(vii) a cardiac disease of a canine, wherein the cardiac disease is one or more selected from the group consisting of: heart failure; congestive heart failure; asymptomatic/preclinical/occult heart failure; heart failure due to (myxomatous) mitral valve disease [(M)MVD]; congestive heart failure due to (myxomatous) mitral valve disease [(M)MVD]; asymptomatic/preclinical/occult heart failure due to (myxomatous) mitral valve disease [(M)MVD]; (myxomatous) mitral valve disease [(M)MVD]; clinically overt (myxomatous) mitral valve disease [(M)MVD]; asymptomatic/preclinical/occult (myxomatous) mitral valve disease [(M)MVD]; heart failure due to dilated cardiomyopathy (DCM); congestive heart failure due to dilated cardiomyopathy (DCM); asymptomatic/preclinical/occult heart failure due to dilated cardiomyopathy (DCM); dilated cardiomyopathy (DCM); clinically overt dilated cardiomyopathy (DCM); asymptomatic/preclinical/occult dilated cardiomyopathy (DCM); and aortic stenosis (valvular, supravalvular and/or subvalvular);

(viii) hypertension in a cat or a dog, wherein the hypertension is one or more selected from the group consisting of: situational hypertension, secondary hypertension and idiopathic hypertension, wherein the secondary hypertension is selected from the group consisting of hypertension associated with chronic kidney disease (CKD), diabetes, obesity, heart disease, endocrine disease, hyperthyroidism, acromegaly, and elevated blood pressure (BP) induced by medicaments;

(ix) a renal disease of a cat or a dog, wherein the renal disease is one or more selected from the group consisting of: renal dysplasia, glomerulopathy, polycystic kidney disease, amyloidosis, tubulo-nephritis/tubulointerstitial nephritis (TIN), acute kidney disease, and chronic kidney disease.

* * * * *